United States Patent
Joseph et al.

(10) Patent No.: US 10,276,809 B2
(45) Date of Patent: Apr. 30, 2019

(54) ORGANIC ELECTROLUMINESCENT MATERIALS AND DEVICES

(71) Applicant: Universal Display Corporation, Ewing, NJ (US)

(72) Inventors: Scott Joseph, Ewing, NJ (US); Pierre-Luc T. Boudreault, Ewing, NJ (US); Chuanjun Xia, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 64 days.

(21) Appl. No.: 15/477,737

(22) Filed: Apr. 3, 2017

(65) Prior Publication Data

US 2017/0288157 A1 Oct. 5, 2017

Related U.S. Application Data

(60) Provisional application No. 62/318,398, filed on Apr. 5, 2016.

(51) Int. Cl.
| | | |
|---|---|---|
| H01L 51/50 | (2006.01) |
| H01L 51/00 | (2006.01) |
| C09K 11/06 | (2006.01) |
| C09K 11/02 | (2006.01) |
| C07F 15/00 | (2006.01) |
| H05B 33/14 | (2006.01) |

(52) U.S. Cl.
CPC ...... *H01L 51/0094* (2013.01); *C07F 15/0033* (2013.01); *C09K 11/025* (2013.01); *C09K 11/06* (2013.01); *H05B 33/14* (2013.01); *C09K 2211/1007* (2013.01); *C09K 2211/1029* (2013.01); *C09K 2211/185* (2013.01); *H01L 51/5012* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |

(Continued)

FOREIGN PATENT DOCUMENTS

| | | |
|---|---|---|
| EP | 650955 | 5/1995 |
| EP | 1238981 | 9/2002 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Gregory D Clark
(74) *Attorney, Agent, or Firm* — Riverside Law LLP

(57) ABSTRACT

This invention discloses novel ligands for metal complexes. These ligands comprise a new side chain, namely silacycloalkane, which could increase the dopants efficiency, tune the emission color, and enhance the lifetime.

20 Claims, 2 Drawing Sheets

(56) References Cited

U.S. PATENT DOCUMENTS

| | | |
|---|---|---|
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,968,146 B2 | 6/2011 | Wanger et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0104472 A1 | 4/2009 | Je et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2013/0026452 A1 | 1/2013 | Kottas et al. |
| 2013/0119354 A1 | 5/2013 | Ma et al. |
| 2013/0146848 A1 | 6/2013 | Ma et al. |
| 2016/0190484 A1 | 6/2016 | Lee et al. |
| 2016/0190485 A1 | 6/2016 | Boudreault et al. |

FOREIGN PATENT DOCUMENTS

| | | |
|---|---|---|
| EP | 1725079 | 11/2006 |
| EP | 2034538 | 3/2009 |
| EP | 2182002 | 5/2010 |
| EP | 2554548 | 2/2013 |
| EP | 2594572 | 5/2013 |
| JP | 200511610 | 1/2005 |
| JP | 2007123392 | 5/2007 |
| JP | 2007254297 | 10/2007 |
| JP | 2008074939 | 10/2009 |
| JP | 2010/135467 | 6/2010 |
| KR | 20110120074 | 11/2011 |
| KR | 20130110934 | 10/2013 |
| WO | 2001039234 | 5/2001 |
| WO | 2002002714 | 1/2002 |
| WO | 215645 | 2/2002 |
| WO | 2003040257 | 5/2003 |
| WO | 2003060956 | 7/2003 |
| WO | 2004093207 | 10/2004 |
| WO | 2004/111066 | 12/2004 |
| WO | 2004107822 | 12/2004 |
| WO | 2005014551 | 2/2005 |
| WO | 5019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 6056418 | 6/2006 |
| WO | 2006/072002 | 7/2006 |
| WO | 2006082742 | 8/2006 |
| WO | 6100298 | 9/2006 |
| WO | 2006098120 | 9/2006 |
| WO | 2006103874 | 10/2006 |
| WO | 2006114966 | 11/2006 |
| WO | 2006132173 | 12/2006 |
| WO | 2007/002683 | 1/2007 |
| WO | 2007004380 | 1/2007 |
| WO | 2007063754 | 6/2007 |
| WO | 2007063796 | 6/2007 |
| WO | 2008/044723 | 4/2008 |
| WO | 2008057394 | 5/2008 |
| WO | 8101842 | 8/2008 |
| WO | 8132085 | 11/2008 |
| WO | 9000673 | 12/2008 |
| WO | 2009/003898 | 1/2009 |
| WO | 2009/008311 | 1/2009 |
| WO | 2009/018009 | 2/2009 |
| WO | 9050290 | 4/2009 |
| WO | 2008/056746 | 5/2009 |
| WO | 2009/021126 | 5/2009 |
| WO | 2009/062578 | 5/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 9100991 | 8/2009 |
| WO | 2010011390 | 1/2010 |
| WO | 2010/111175 | 9/2010 |

OTHER PUBLICATIONS

Baldo et al., "Very high-efficiency green organic light-emitting devices based on electrophosphorescence," Appl. Phys. Lett., vol. 75, No. 1, 4-6 (1999).

U.S. Appl. No. 13/193,221, filed Jul. 28, 2011.

U.S. Appl. No. 13/296,806, filed Nov. 15, 2011.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865- 867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Diodes with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NCN-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., "A Novel Class of Phosphorescent Gold(III) Alkynyl-Based Organic Light-Emitting Devices with Tunable Colour," *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2- α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylbory1)-2,2'-bithiophene and 5,5"-Bis(dimesitylbory1)-2,240 :5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on p-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15 ):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

ORGANIC ELECTROLUMINESCENT MATERIALS AND DEVICES

CROSS-REFERENCE TO RELATED APPLICATIONS

This application claims priority to U.S. Patent Application Ser. No. 62/318,398, filed Apr. 5, 2016, the entire contents of which is incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

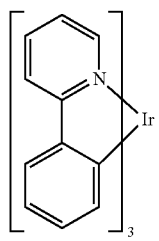

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

There is need in the art for novel emitters which can be used for electroluminescent devices. The present invention addresses this unmet need.

SUMMARY

According to an embodiment, a composition is provided that includes a first compound;
wherein the first compound is capable of functioning as an emitter in an organic light emitting device at room temperature;
wherein the first compound has at least one aromatic ring and at least one substituent R;
wherein each of the at least one substituent R is directly bonded to one of the aromatic rings;
wherein each of the at least one substituent R has the formula

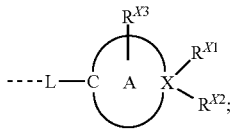

wherein L is a direct bond or an organic linker;
wherein ring A is a non-aromatic cyclic group containing X;
wherein L bonds to ring A at a carbon atom C;
wherein X is Si or Ge;
wherein $R^{X3}$ represents mono to the possible maximum number of substitution, or no substitution;
wherein $R^{X1}$, $R^{X2}$ and $R^{X3}$ are each independently selected from the group consisting of: hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substituents $R^{X2}$ and $R^{X3}$ are optionally joined or fused into a ring.

According to another embodiment, an organic light emitting diode/device (OLED) is also provided. The OLED can include an anode, a cathode, and an organic layer, disposed between the anode and the cathode. The organic layer can include a compound of the invention. According to yet another embodiment, the organic light emitting device is incorporated into a device selected from a consumer product, an electronic component module, and/or a lighting panel.

According to another embodiment, a consumer product comprising one or more organic light emitting devices is also provided. The organic light emitting device can include an anode, a cathode, and an organic layer, disposed between the anode and the cathode, wherein the organic layer can include a compound of the invention. The consumer product can be a flat panel display, a computer monitor, a medical monitors television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and/or a sign.

According to another embodiment, a formulation containing a compound of the invention is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
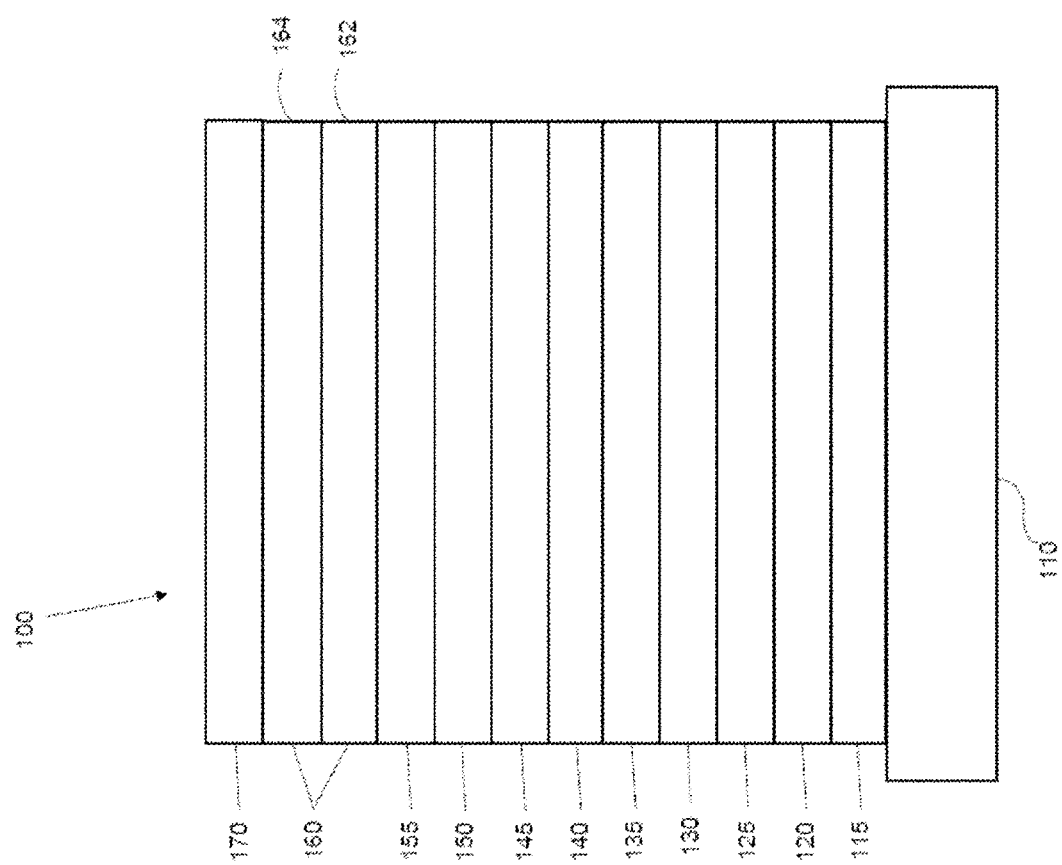
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F$_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
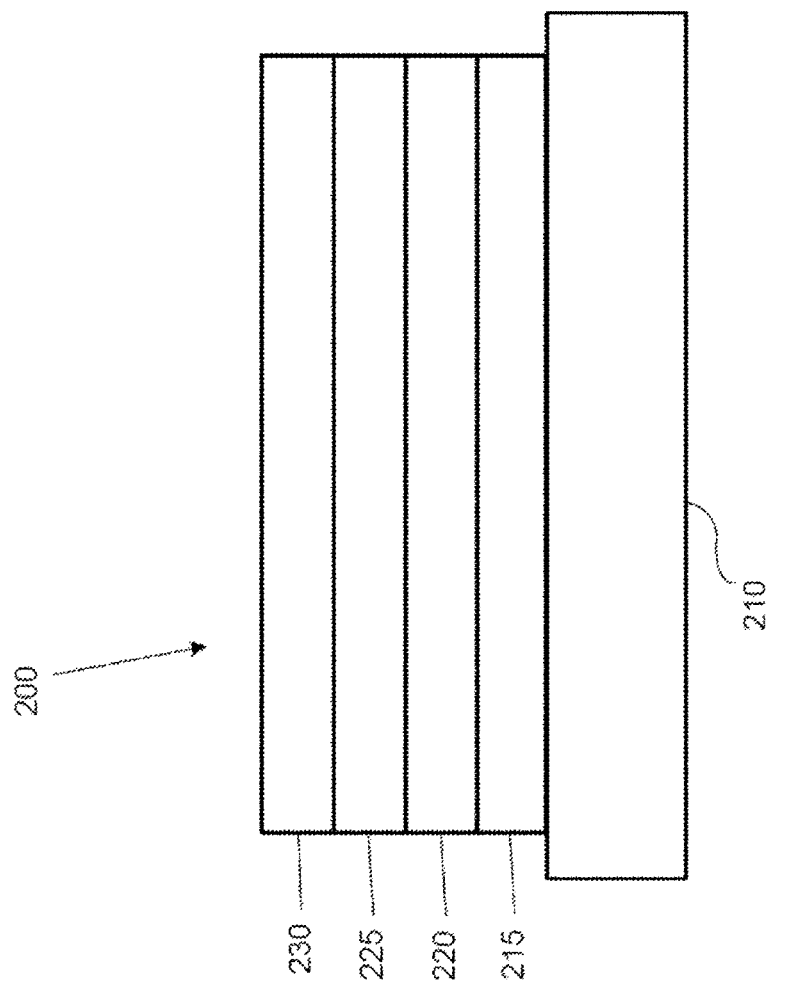
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays that are less than 2 inches diagonal, 3-D displays, virtual reality or augmented reality displays, vehicles, video walls comprising multiple displays tiled together, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In one aspect, this invention includes phosphorescent metal complexes containing substituents with the silacycloalkane moiety. This side chain can be added at different positions on a wide variety of ligands including NHC carbene, imidazole, pyridine, pyrazine, pyrimidine, quinoline, iso-quinoline, quinazoline, and quinoxaline. This substitution was found to be useful for multiple reasons. The lifetime of trimethylsilyl containing emitters may be improved by inserting a methylene spacer between the silyl group and aromatic ring. Further improvement in lifetime may be achieved by affixing the silicon atom(s) in a cycloalkyl ring. In addition, the substituent is very bulky, which may prevent packing in the solid state and increase PLQY.

Compounds of the Invention

In one aspect, the present invention includes a composition comprising a first compound;

wherein the first compound is capable of functioning as an emitter in an organic light emitting device at room temperature;

wherein the first compound has at least one aromatic ring and at least one substituent R;

wherein each of the at least one R is directly bonded to one of the aromatic rings;

wherein each of the at least one R has the formula of

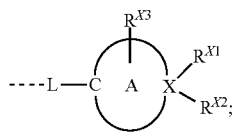

wherein L is a direct bond or an organic linker;
wherein ring A is a non-aromatic cyclic group containing X;

wherein L bonds to ring A at a carbon atom C;
wherein X is Si or Ge;
wherein $R^{X3}$ represents mono to the possible maximum number of substitution, or no substitution;
wherein $R^{X1}$, $R^{X2}$ and $R^{X3}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substitutents of $R^{X1}$, $R^{X2}$ and $R^{X3}$ are optionally joined or fused into a ring.

In one embodiment, L is a direct bond. In another embodiment, L is an organic linker selected from the group consisting of: $NR^{X4}$, $SiR^{X4}R^{X5}$, $GeR^{X4}R^{X5}$, alkyl, cycloalkyl, and combinations thereof; wherein $R^{X4}$ and $R^{X5}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substituents $R^{X1}$, $R^{X2}$ and $R^{X3}$, $R^{X4}$ and $R^{X5}$ are optionally joined or fused into a ring.

In one embodiment, X is Si. In another embodiment, X is Ge.

In one embodiment, $R^{X1}$ and $R^{X2}$ are each independently selected from the group consisting of alkyl, cycloalkyl, partially or fully deuterated variants thereof, partially or fully fluorinated variants thereof, and combinations thereof. In another embodiment, $R^{X1}$ and $R^{X2}$ are joined or fused into a ring.

In one embodiment, each $R^{X3}$ is independently selected from the group consisting of hydrogen, deuterium, halide, alkyl, cycloalkyl, and combinations thereof.

In one embodiment, ring A consists of atoms selected from the group consisting of C, Si, Ge, N, O, and S. In another embodiment, ring A consists of at least two atoms selected from the group consisting of Si, Ge, N, O, and S. In another embodiment, ring A consists of at least three atoms selected from the group consisting of Si, Ge, N, O, and S. In one embodiment, ring A is selected from the group consisting of

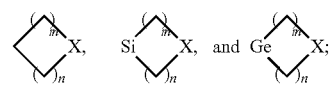

wherein m and n are each independently an integer of 1 to 5. In one embodiment, m+n is 3 or 4.

In one embodiment, in each of the at least one substituent R, ring A is monocyclic. In another embodiment, in each of the at least one substituent R, ring A is a bicyclic group. In another embodiment, each of the at least one substituent R is independently selected from the group consisting of:

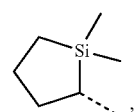

$R^{A1}$

-continued
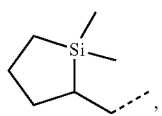,
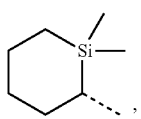,
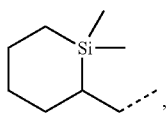,
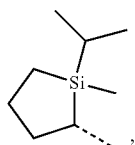,
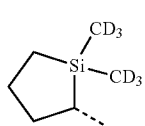,
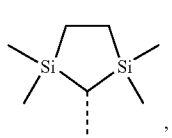,
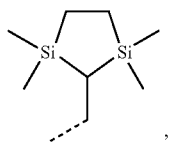,
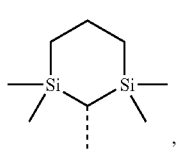,
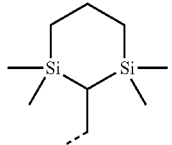,
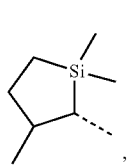,
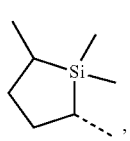,
-continued
$R^{A2}$
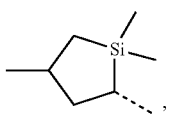,
$R^{A3}$
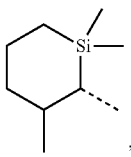,
$R^{A4}$
,
$R^{A5}$
,
$R^{A6}$
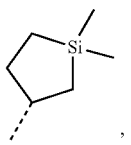,
$R^{A7}$
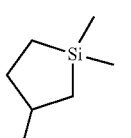,
$R^{A8}$
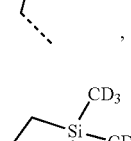,
$R^{A9}$
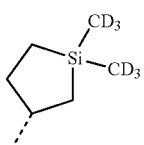,
$R^{A10}$
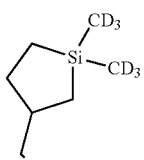,
$R^{A11}$
$R^{A12}$
,
$R^{A13}$
$R^{A14}$
$R^{A15}$
$R^{A16}$
$R^{A17}$
$R^{A18}$
$R^{A19}$
$R^{A20}$
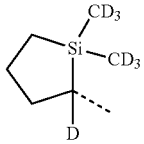,
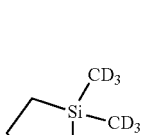,
$R^{A21}$
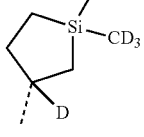,

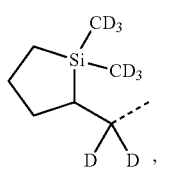
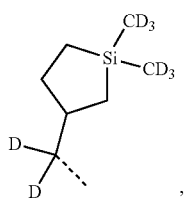
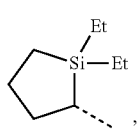
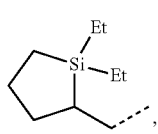
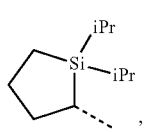
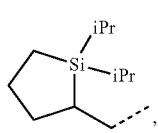
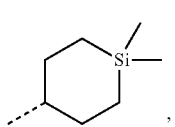
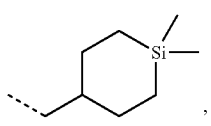
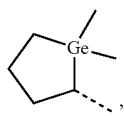
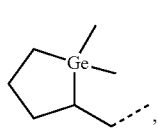
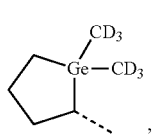
R<sup>A22</sup> 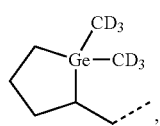,
R<sup>A23</sup> 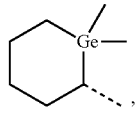,
R<sup>A24</sup> 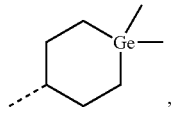,
R<sup>A25</sup> 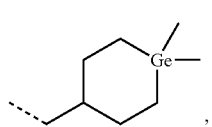,
R<sup>A26</sup> 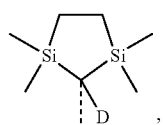,
R<sup>A27</sup> 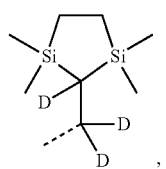,
R<sup>A28</sup> 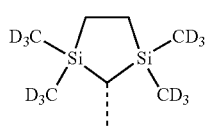,
R<sup>A29</sup> 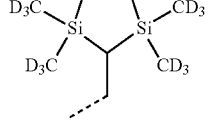,
R<sup>A30</sup>
R<sup>A31</sup> 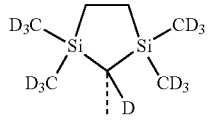,
R<sup>A32</sup> 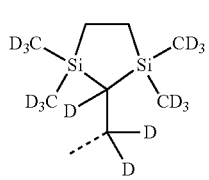,
R<sup>A33</sup>
R<sup>A34</sup>
R<sup>A35</sup>
R<sup>A36</sup>
R<sup>A37</sup>
R<sup>A38</sup>
R<sup>A39</sup>
R<sup>A40</sup>
R<sup>A41</sup>
R<sup>A42</sup>
R<sup>A43</sup>

-continued

R^A444 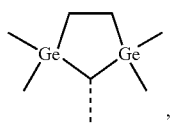,

R^A445 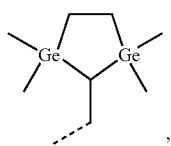,

R^A446 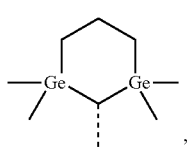,

R^A447 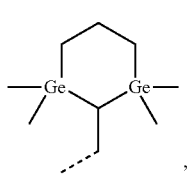,

R^A448 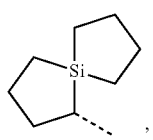,

R^A449 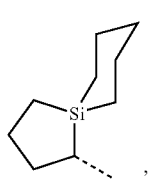,

R^A450 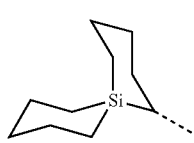,

R^A451 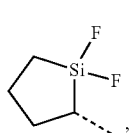,

R^A452 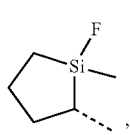,

R^A453 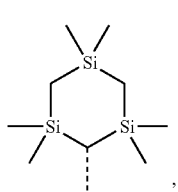,

R^A454 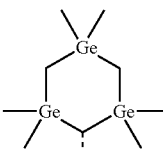,

R^A455 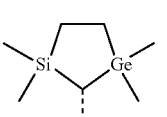,

R^A456 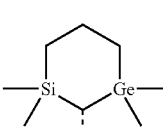,

R^A457 ,

R^A458 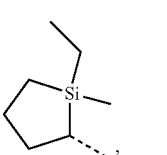,

R^A459 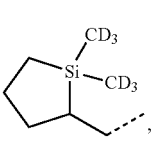, and

R^A460 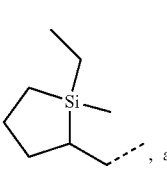.

In one embodiment, the first compound is a metal coordination complex having a metal-carbon bond. In one embodiment, the metal is selected from the group consisting of: Ir, Rh, Re, Ru, Os, Pt, Au, and Cu. In one embodiment, the metal is Ir. In another embodiment, the metal is Pt.

In one embodiment, the first compound has the formula of $M(L^1)_x(L^2)_y(L^3)_z$;

wherein $L^1$, $L^2$ and $L^3$ can be the same or different;

wherein x is 1, 2, or 3;

wherein y is 0, 1, or 2;

wherein z is 0, 1, or 2;

wherein x+y+z is the oxidation state of the metal M;

wherein $L^1$, $L^2$ and $L^3$ are each independently selected from the group consisting of:

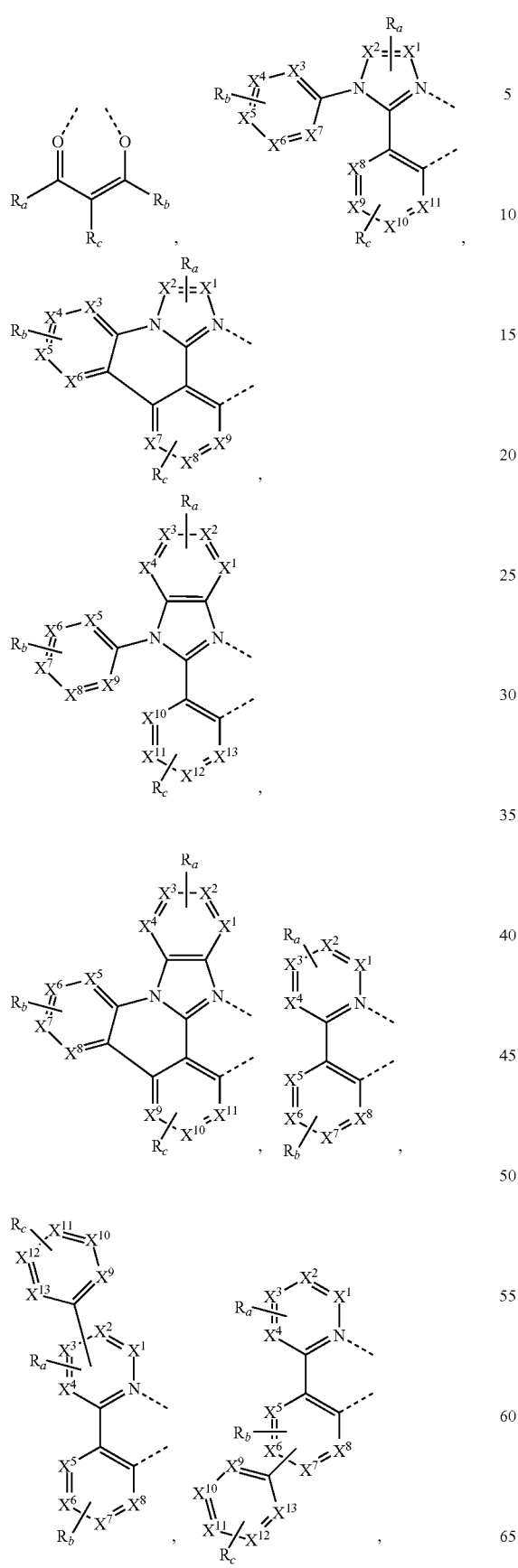
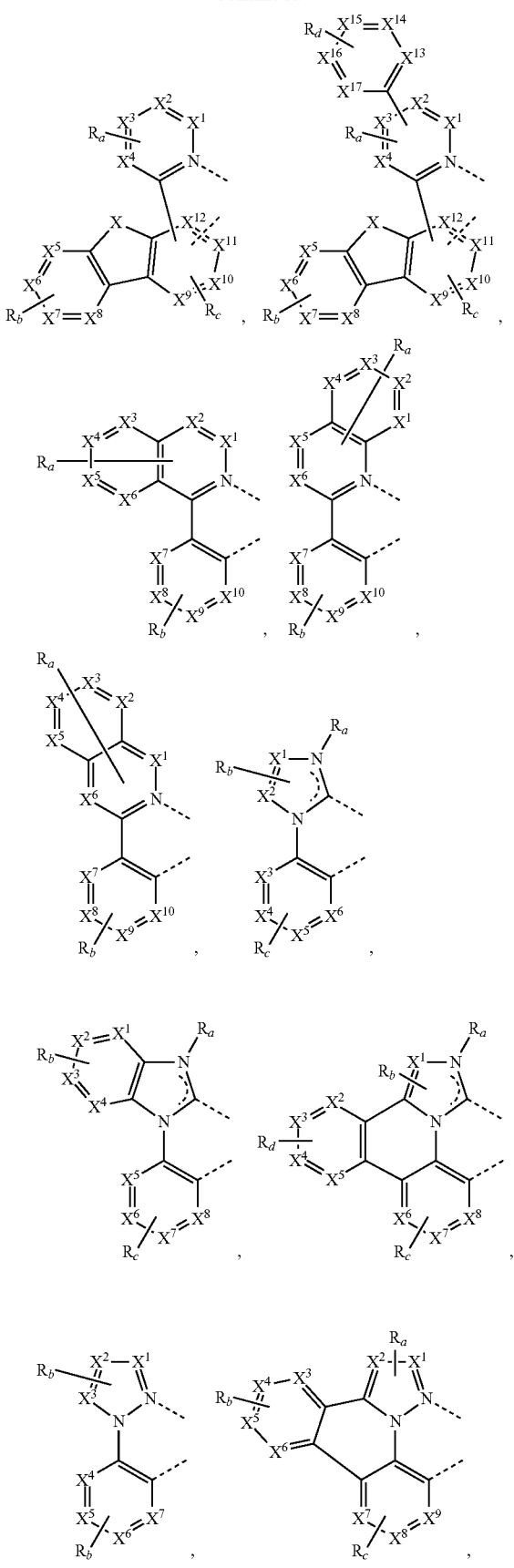

-continued

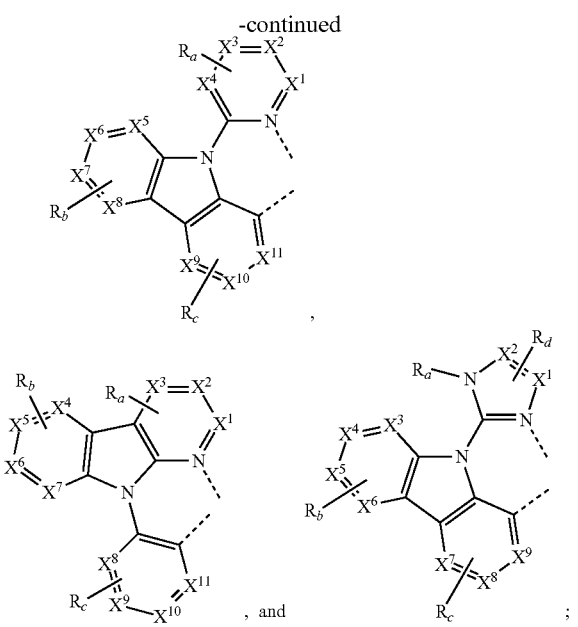

, and ;

wherein each $X^1$ to $X^{17}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any two adjacent substituents of $R_a$, $R_b$, $R_c$ and $R_d$ are optionally fused or joined to form a ring or form a multidentate ligand; and wherein at least one of the $R_a$, $R_b$, $R_c$, and $R_d$ includes at least one substituent R.

In one embodiment, the first compound has the formula of Ir(L$^1$)$_2$(L$^2$). In another embodiment, the first compound has the formula of Pt(L$^1$)$_2$ or Pt(L$^1$)(L$^2$).

In another embodiment, L$^1$ has a formula selected from the group consisting of:

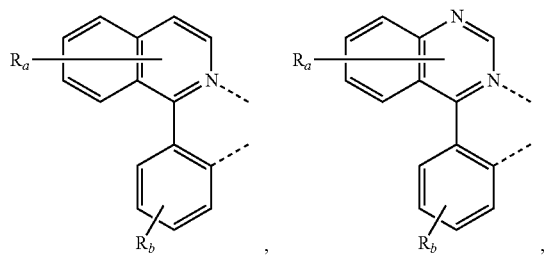

-continued

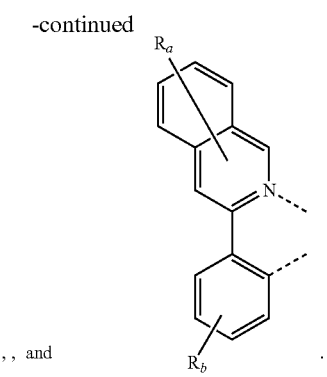

, , and .

wherein L$^2$ has the formula:

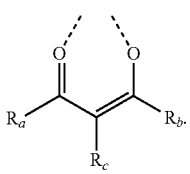

In one embodiment, L$^2$ has the formula:

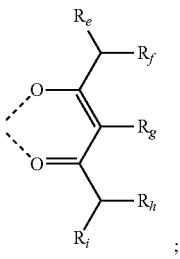

wherein $R_e$, $R_f$, $R_h$, and $R_i$ are independently selected from group consisting of alkyl, cycloalkyl, aryl, and heteroaryl;

wherein at least one of $R_e$, $R_f$, $R_h$, and $R_i$ has at least two carbon atoms;

wherein $R_g$ is selected from group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In one embodiment, L$^1$ and L$^2$ are different and are each independently selected from a group consisting of:

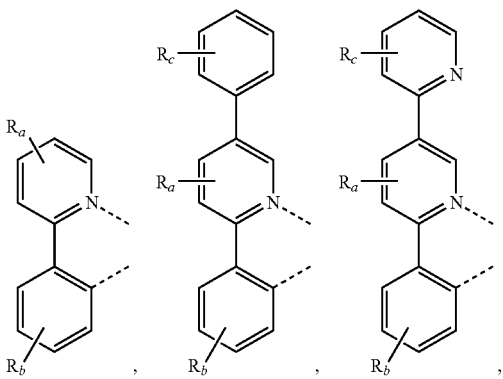

,

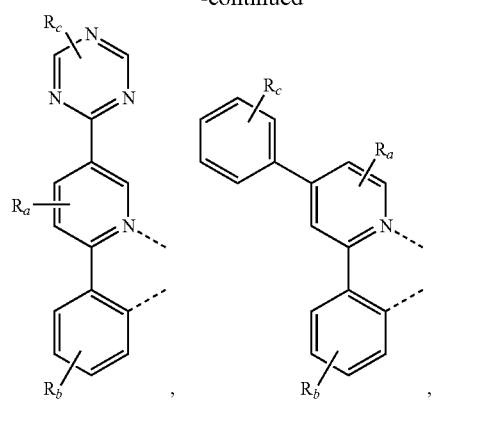
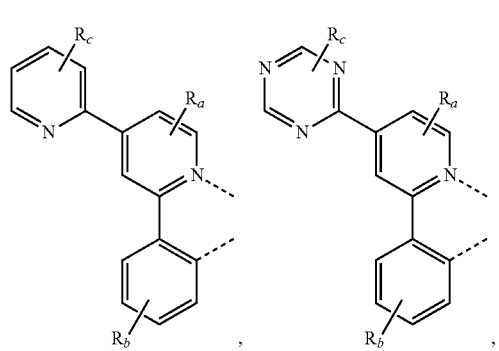
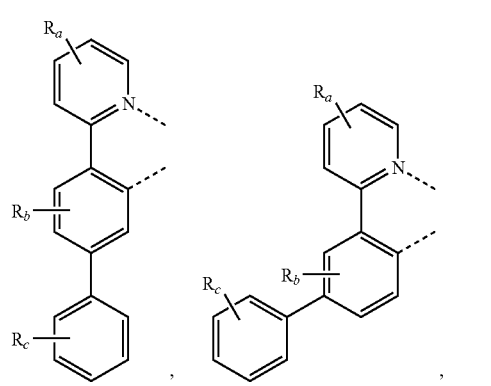
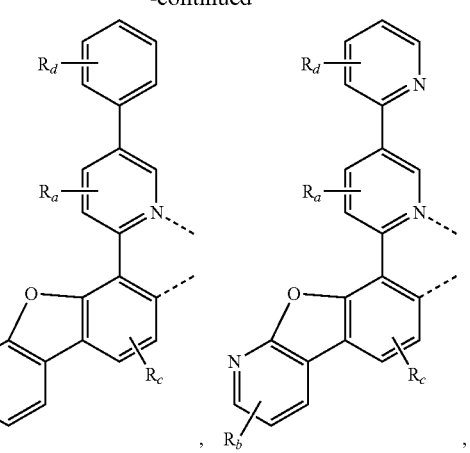
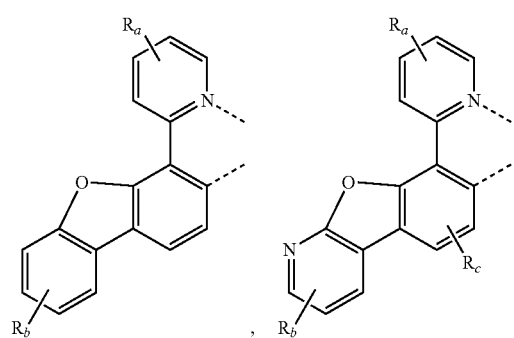
, and

-continued

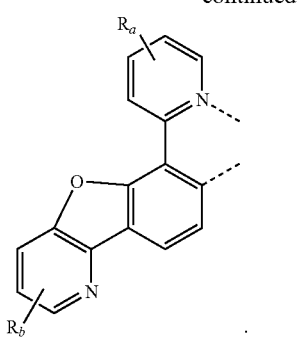

In another embodiment, $L^1$ and $L^2$ are each independently selected from the group consisting of:

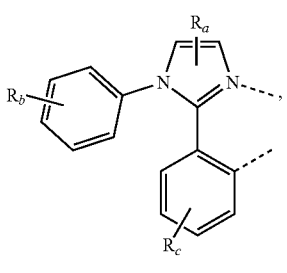

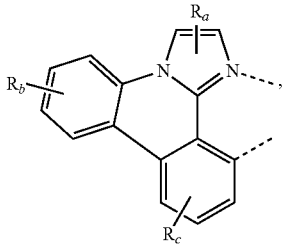

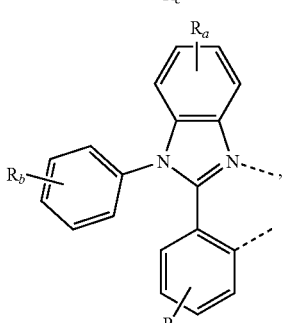

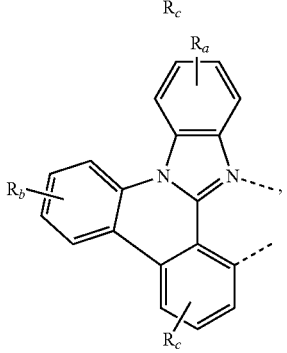

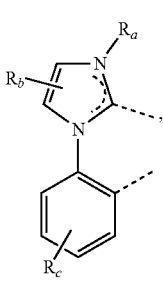

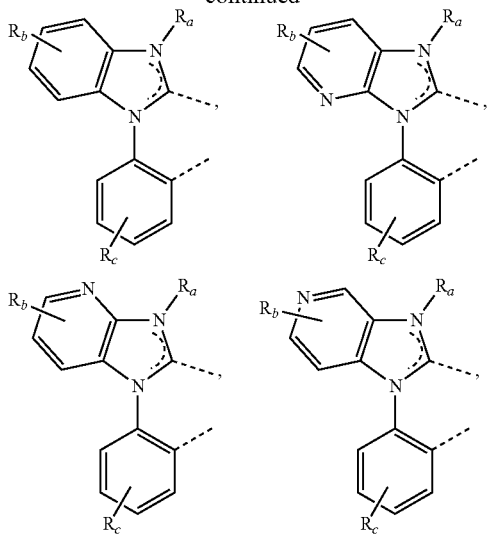

and

In one embodiment, $L^1$ is connected to the other $L^1$ or $L^2$ to form a tetradentate ligand.

In one embodiment, at least one of $R_a$, $R_b$, $R_c$ and $R_d$ includes an alkyl or cycloalkyl group that includes CD, $CD_2$, or $CD_3$, wherein D is deuterium.

In one embodiment, at least one of $L^1$, $L^2$, and $L^3$ is selected from the group consisting of:

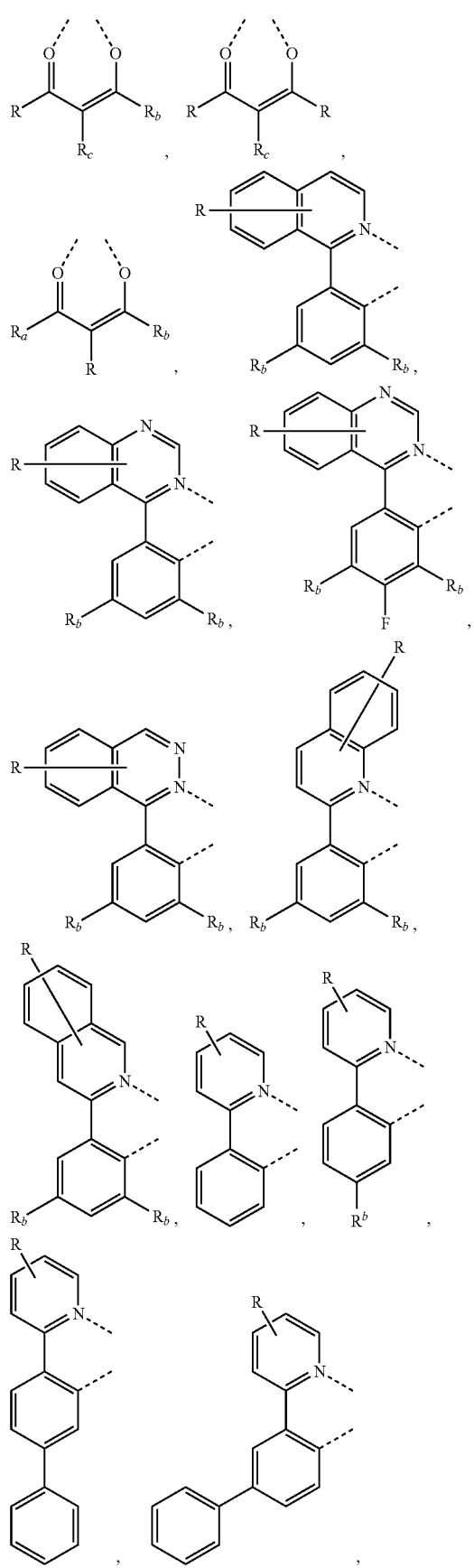
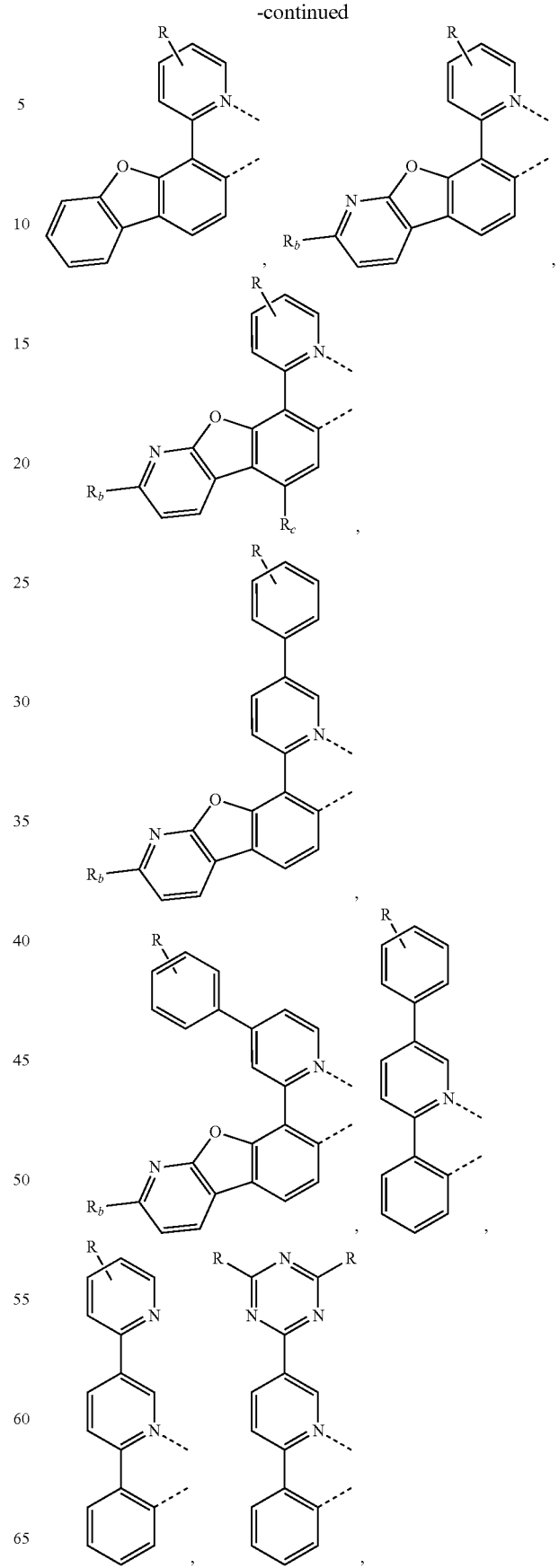

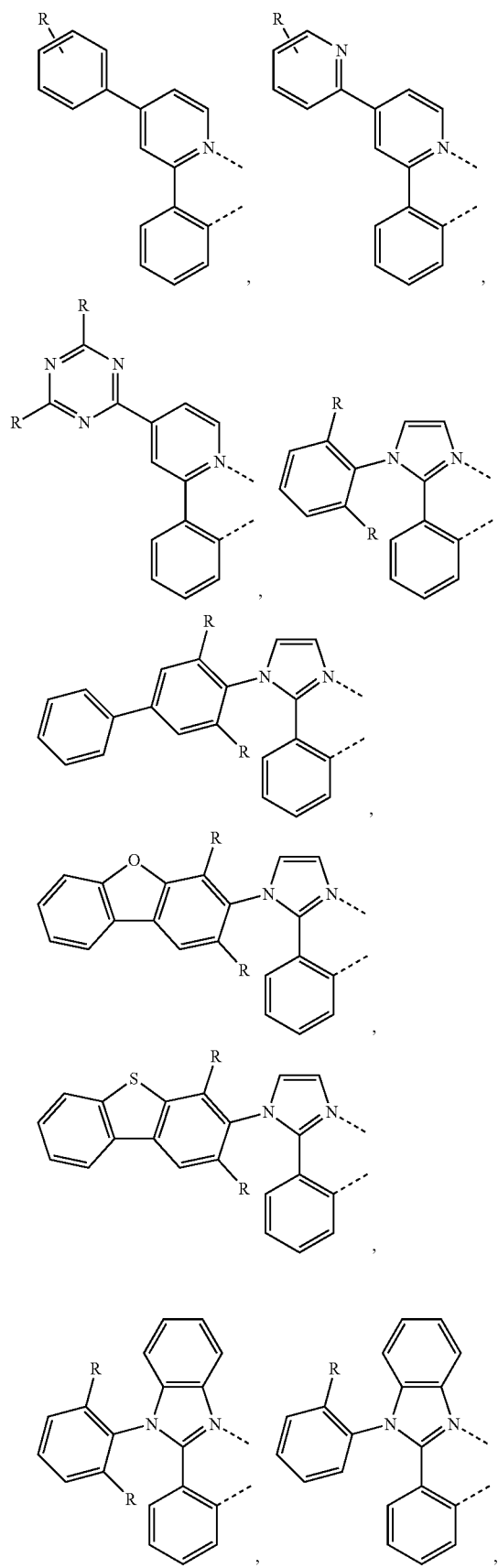
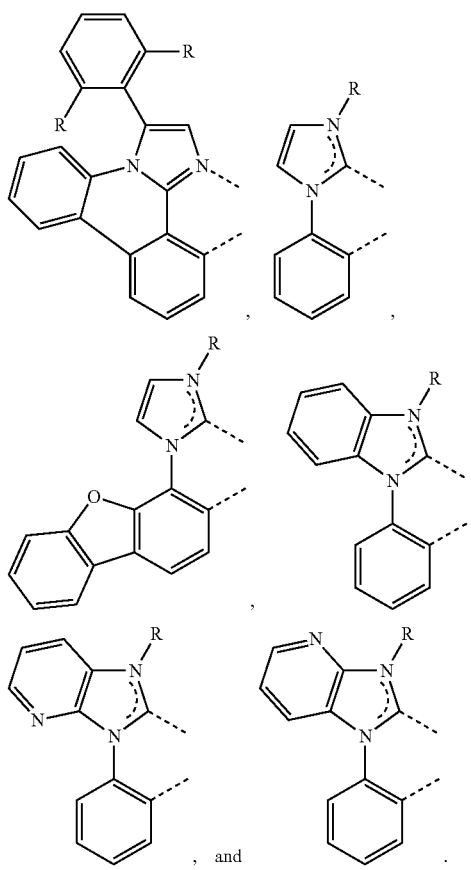
, and
In another embodiment, at least one of $L^1$, $L^2$, and $L^3$ is selected from the group consisting of:
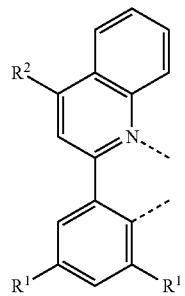
$R^2 = R^{A1}, R^1 = R^{B1}, L_{A1}$
$R^2 = R^{A2}, R^1 = R^{B1}, L_{A2}$
$R^2 = R^{A3}, R^1 = R^{B1}, L_{A3}$
$R^2 = R^{A4}, R^1 = R^{B1}, L_{A4}$
$R^2 = R^{A5}, R^1 = R^{B1}, L_{A5}$
$R^2 = R^{A1}, R^1 = R^{B2}, L_{A6}$
$R^2 = R^{A2}, R^1 = R^{B2}, L_{A7}$
$R^2 = R^{A3}, R^1 = R^{B2}, L_{A8}$
$R^2 = R^{A4}, R^1 = R^{B2}, L_{A9}$
$R^2 = R^{A5}, R^1 = R^{B2}, L_{A10}$ -continued

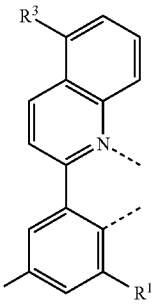

R³ = R⁴¹, R¹ = R^{B1}, $L_{A11}$
R³ = R⁴², R¹ = R^{B1}, $L_{A12}$
R³ = R⁴³, R¹ = R^{B1}, $L_{A13}$
R³ = R⁴⁴, R¹ = R^{B1}, $L_{A14}$
R³ = R⁴⁵, R¹ = R^{B1}, $L_{A15}$
R³ = R⁴¹, R¹ = R^{B2}, $L_{A16}$
R³ = R⁴², R¹ = R^{B2}, $L_{A17}$
R³ = R⁴³, R¹ = R^{B2}, $L_{A18}$
R³ = R⁴⁴, R¹ = R^{B2}, $L_{A19}$
R³ = R⁴⁵, R¹ = R^{B2}, $L_{A20}$

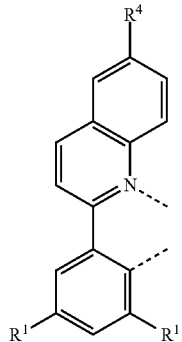

R⁴ = R⁴¹, R¹ = R^{B1}, $L_{A21}$
R⁴ = R⁴², R¹ = R^{B1}, $L_{A22}$
R⁴ = R⁴³, R¹ = R^{B1}, $L_{A23}$
R⁴ = R⁴⁴, R¹ = R^{B1}, $L_{A24}$
R⁴ = R⁴⁵, R¹ = R^{B1}, $L_{A25}$
R⁴ = R⁴¹, R¹ = R^{B2}, $L_{A26}$
R⁴ = R⁴², R¹ = R^{B2}, $L_{A27}$
R⁴ = R⁴³, R¹ = R^{B2}, $L_{A28}$
R⁴ = R⁴⁴, R¹ = R^{B2}, $L_{A29}$
R⁴ = R⁴⁵, R¹ = R^{B2}, $L_{A30}$

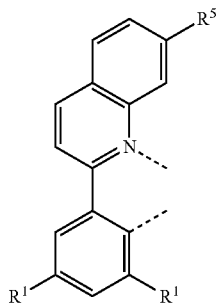

R⁵ = R⁴¹, R¹ = R^{B1}, $L_{A31}$
R⁵ = R⁴², R¹ = R^{B1}, $L_{A32}$
R⁵ = R⁴³, R¹ = R^{B1}, $L_{A33}$
R⁵ = R⁴⁴, R¹ = R^{B1}, $L_{A34}$
R⁵ = R⁴⁵, R¹ = R^{B1}, $L_{A35}$
R⁵ = R⁴¹, R¹ = R^{B2}, $L_{A36}$
R⁵ = R⁴², R¹ = R^{B2}, $L_{A37}$
R⁵ = R⁴³, R¹ = R^{B2}, $L_{A38}$
R⁵ = R⁴⁴, R¹ = R^{B2}, $L_{A39}$
R⁵ = R⁴⁵, R¹ = R^{B2}, $L_{A40}$

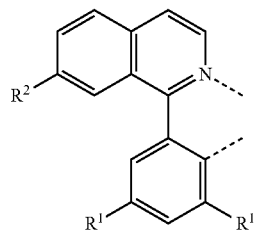

R² = R⁴¹, R¹ = R^{B1}, $L_{A41}$
R² = R⁴², R¹ = R^{B1}, $L_{A42}$
R² = R⁴³, R¹ = R^{B1}, $L_{A43}$
R² = R⁴⁴, R¹ = R^{B1}, $L_{A44}$
R² = R⁴⁵, R¹ = R^{B1}, $L_{A45}$
R² = R⁴¹, R¹ = R^{B2}, $L_{A46}$
R² = R⁴², R¹ = R^{B2}, $L_{A47}$
R² = R⁴³, R¹ = R^{B2}, $L_{A48}$
R² = R⁴⁴, R¹ = R^{B2}, $L_{A49}$
R² = R⁴⁵, R¹ = R^{B2}, $L_{A50}$

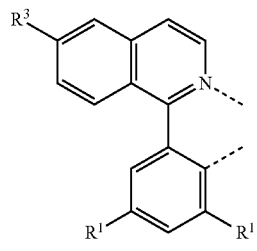

R³ = R⁴¹, R¹ = R^{B1}, $L_{A51}$
R³ = R⁴², R¹ = R^{B1}, $L_{A52}$
R³ = R⁴³, R¹ = R^{B1}, $L_{A53}$
R³ = R⁴⁴, R¹ = R^{B1}, $L_{A54}$
R³ = R⁴⁵, R¹ = R^{B1}, $L_{A55}$
R³ = R⁴¹, R¹ = R^{B2}, $L_{A56}$
R³ = R⁴², R¹ = R^{B2}, $L_{A57}$
R³ = R⁴³, R¹ = R^{B2}, $L_{A58}$
R³ = R⁴⁴, R¹ = R^{B2}, $L_{A59}$
R³ = R⁴⁵, R¹ = R^{B2}, $L_{A60}$

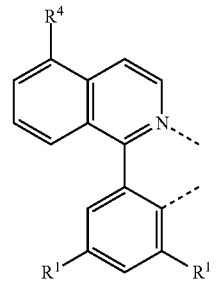

R⁴ = R⁴¹, R¹ = R^{B1}, $L_{A61}$
R⁴ = R⁴², R¹ = R^{B1}, $L_{A62}$
R⁴ = R⁴³, R¹ = R^{B1}, $L_{A63}$
R⁴ = R⁴⁴, R¹ = R^{B1}, $L_{A64}$
R⁴ = R⁴⁵, R¹ = R^{B1}, $L_{A65}$
R⁴ = R⁴¹, R¹ = R^{B2}, $L_{A66}$
R⁴ = R⁴², R¹ = R^{B2}, $L_{A67}$
R⁴ = R⁴³, R¹ = R^{B2}, $L_{A68}$
R⁴ = R⁴⁴, R¹ = R^{B2}, $L_{A69}$
R⁴ = R⁴⁵, R¹ = R^{B2}, $L_{A70}$

-continued

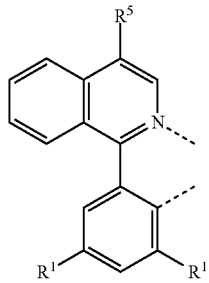

R⁵ = R^{A1}, R¹ = R^{B1}, L_{A71}
R⁵ = R^{A2}, R¹ = R^{B1}, L_{A72}
R⁵ = R^{A3}, R¹ = R^{B1}, L_{A73}
R⁵ = R^{A4}, R¹ = R^{B1}, L_{A74}
R⁵ = R^{A5}, R¹ = R^{B1}, L_{A75}
R⁵ = R^{A1}, R¹ = R^{B2}, L_{A76}
R⁵ = R^{A2}, R¹ = R^{B2}, L_{A77}
R⁵ = R^{A3}, R¹ = R^{B2}, L_{A78}
R⁵ = R^{A4}, R¹ = R^{B2}, L_{A79}
R⁵ = R^{A5}, R¹ = R^{B2}, L_{A80}

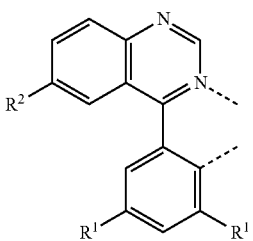

R² = R^{A1}, R¹ = R^{B1}, L_{A81}
R² = R^{A2}, R¹ = R^{B1}, L_{A82}
R² = R^{A3}, R¹ = R^{B1}, L_{A83}
R² = R^{A4}, R¹ = R^{B1}, L_{A84}
R² = R^{A5}, R¹ = R^{B1}, L_{A85}
R² = R^{A1}, R¹ = R^{B2}, L_{A86}
R² = R^{A2}, R¹ = R^{B2}, L_{A87}
R² = R^{A3}, R¹ = R^{B2}, L_{A88}
R² = R^{A4}, R¹ = R^{B2}, L_{A89}
R² = R^{A5}, R¹ = R^{B2}, L_{A90}

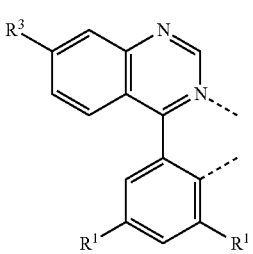

R³ = R^{A1}, R¹ = R^{B1}, L_{A91}
R³ = R^{A2}, R¹ = R^{B1}, L_{A92}
R³ = R^{A3}, R¹ = R^{B1}, L_{A93}
R³ = R^{A4}, R¹ = R^{B1}, L_{A94}
R³ = R^{A5}, R¹ = R^{B1}, L_{A95}
R³ = R^{A1}, R¹ = R^{B2}, L_{A96}
R³ = R^{A2}, R¹ = R^{B2}, L_{A97}
R³ = R^{A3}, R¹ = R^{B2}, L_{A98}
R³ = R^{A4}, R¹ = R^{B2}, L_{A99}
R³ = R^{A5}, R¹ = R^{B2}, L_{A100}

-continued

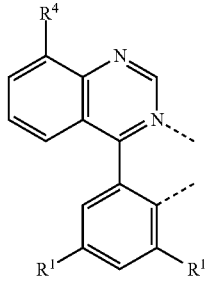

R⁴ = R^{A1}, R¹ = R^{B1}, L_{A101}
R⁴ = R^{A2}, R¹ = R^{B1}, L_{A102}
R⁴ = R^{A3}, R¹ = R^{B1}, L_{A103}
R⁴ = R^{A4}, R¹ = R^{B1}, L_{A104}
R⁴ = R^{A5}, R¹ = R^{B1}, L_{A105}
R⁴ = R^{A1}, R¹ = R^{B2}, L_{A106}
R⁴ = R^{A2}, R¹ = R^{B2}, L_{A107}
R⁴ = R^{A3}, R¹ = R^{B2}, L_{A108}
R⁴ = R^{A4}, R¹ = R^{B2}, L_{A109}
R⁴ = R^{A5}, R¹ = R^{B2}, L_{A110}

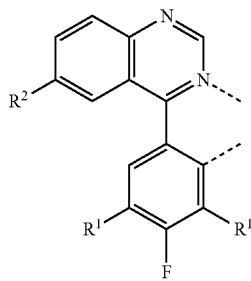

R² = R^{A1}, R¹ = R^{B1}, L_{A111}
R² = R^{A2}, R¹ = R^{B1}, L_{A112}
R² = R^{A3}, R¹ = R^{B1}, L_{A113}
R² = R^{A4}, R¹ = R^{B1}, L_{A114}
R² = R^{A5}, R¹ = R^{B1}, L_{A115}
R² = R^{A1}, R¹ = R^{B2}, L_{A116}
R² = R^{A2}, R¹ = R^{B2}, L_{A117}
R² = R^{A3}, R¹ = R^{B2}, L_{A118}
R² = R^{A4}, R¹ = R^{B2}, L_{A119}
R² = R^{A5}, R¹ = R^{B2}, L_{A120}

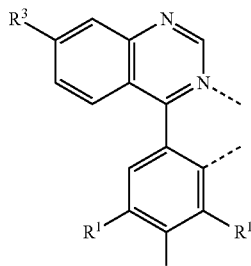

R³ = R^{A1}, R¹ = R^{B1}, L_{A121}
R³ = R^{A2}, R¹ = R^{B1}, L_{A122}
R³ = R^{A3}, R¹ = R^{B1}, L_{A123}
R³ = R^{A4}, R¹ = R^{B1}, L_{A124}
R³ = R^{A5}, R¹ = R^{B1}, L_{A125}
R³ = R^{A1}, R¹ = R^{B2}, L_{A126}
R³ = R^{A2}, R¹ = R^{B2}, L_{A127}
R³ = R^{A3}, R¹ = R^{B2}, L_{A128}
R³ = R^{A4}, R¹ = R^{B2}, L_{A129}
R³ = R^{A5}, R¹ = R^{B2}, L_{A130}

-continued

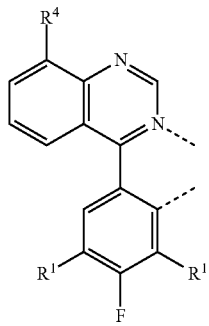

R⁴ = R^{A1}, R¹ = R^{B1}, L_{A131}
R⁴ = R^{A2}, R¹ = R^{B1}, L_{A132}
R⁴ = R^{A3}, R¹ = R^{B1}, L_{A133}
R⁴ = R^{A4}, R¹ = R^{B1}, L_{A134}
R⁴ = R^{A5}, R¹ = R^{B1}, L_{A135}
R⁴ = R^{A1}, R¹ = R^{B2}, L_{A136}
R⁴ = R^{A2}, R¹ = R^{B2}, L_{A137}
R⁴ = R^{A3}, R¹ = R^{B2}, L_{A138}
R⁴ = R^{A4}, R¹ = R^{B2}, L_{A139}
R⁴ = R^{A5}, R¹ = R^{B2}, L_{A140}

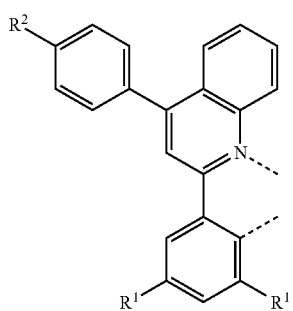

R² = R^{A1}, R¹ = R^{B1}, L_{A141}
R² = R^{A2}, R¹ = R^{B1}, L_{A142}
R² = R^{A3}, R¹ = R^{B1}, L_{A143}
R² = R^{A4}, R¹ = R^{B1}, L_{A144}
R² = R^{A5}, R¹ = R^{B1}, L_{A145}
R² = R^{A1}, R¹ = R^{B2}, L_{A146}
R² = R^{A2}, R¹ = R^{B2}, L_{A147}
R² = R^{A3}, R¹ = R^{B2}, L_{A148}
R² = R^{A4}, R¹ = R^{B2}, L_{A149}
R² = R^{A5}, R¹ = R^{B2}, L_{A150}

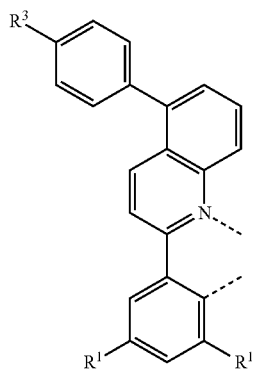

R³ = R^{A1}, R¹ = R^{B1}, L_{A151}
R³ = R^{A2}, R¹ = R^{B1}, L_{A152}
R³ = R^{A3}, R¹ = R^{B1}, L_{A153}
R³ = R^{A4}, R¹ = R^{B1}, L_{A154}
R³ = R^{A5}, R¹ = R^{B1}, L_{A155}
R³ = R^{A1}, R¹ = R^{B2}, L_{A156}
R³ = R^{A2}, R¹ = R^{B2}, L_{A157}
R³ = R^{A3}, R¹ = R^{B2}, L_{A158}

-continued

R³ = R^{A4}, R¹ = R^{B2}, L_{A159}
R³ = R^{A5}, R¹ = R^{B2}, L_{A160}

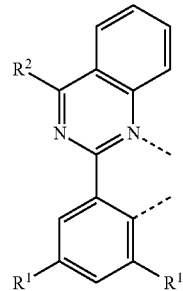

R² = R^{A1}, R¹ = R^{B1}, L_{A161}
R² = R^{A2}, R¹ = R^{B1}, L_{A162}
R² = R^{A3}, R¹ = R^{B1}, L_{A163}
R² = R^{A4}, R¹ = R^{B1}, L_{A164}
R² = R^{A5}, R¹ = R^{B1}, L_{A165}
R² = R^{A1}, R¹ = R^{B2}, L_{A166}
R² = R^{A2}, R¹ = R^{B2}, L_{A167}
R² = R^{A3}, R¹ = R^{B2}, L_{A168}
R² = R^{A4}, R¹ = R^{B2}, L_{A169}
R² = R^{A5}, R¹ = R^{B2}, L_{A170}

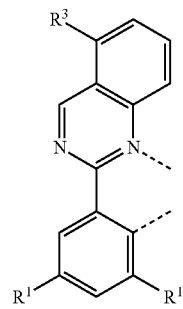

R³ = R^{A1}, R¹ = R^{B1}, L_{A171}
R³ = R^{A2}, R¹ = R^{B1}, L_{A172}
R³ = R^{A3}, R¹ = R^{B1}, L_{A173}
R³ = R^{A4}, R¹ = R^{B1}, L_{A174}
R³ = R^{A5}, R¹ = R^{B1}, L_{A175}
R³ = R^{A1}, R¹ = R^{B2}, L_{A176}
R³ = R^{A2}, R¹ = R^{B2}, L_{A177}
R³ = R^{A3}, R¹ = R^{B2}, L_{A178}
R³ = R^{A4}, R¹ = R^{B2}, L_{A179}
R³ = R^{A5}, R¹ = R^{B2}, L_{A180}

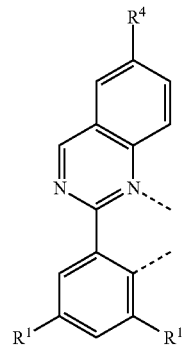

R⁴ = R^{A1}, R¹ = R^{B1}, L_{A181}
R⁴ = R^{A2}, R¹ = R^{B1}, L_{A182}
R⁴ = R^{A3}, R¹ = R^{B1}, L_{A183}
R⁴ = R^{A4}, R¹ = R^{B1}, L_{A184}
R⁴ = R^{A5}, R¹ = R^{B1}, L_{A185}
R⁴ = R^{A1}, R¹ = R^{B2}, L_{A186}
R⁴ = R^{A2}, R¹ = R^{B2}, L_{A187}

R⁴ = R^A3, R¹ = R^B2, L_A188
R⁴ = R^A4, R¹ = R^B2, L_A189
R⁴ = R^A5, R¹ = R^B2, L_A190

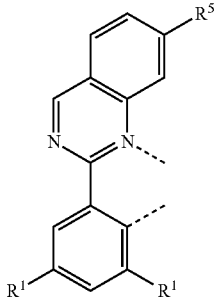

R⁵ = R^A1, R¹ = R^B1, L_A191
R⁵ = R^A2, R¹ = R^B1, L_A192
R⁵ = R^A3, R¹ = R^B1, L_A193
R⁵ = R^A4, R¹ = R^B1, L_A194
R⁵ = R^A5, R¹ = R^B1, L_A195
R⁵ = R^A1, R¹ = R^B2, L_A196
R⁵ = R^A2, R¹ = R^B2, L_A197
R⁵ = R^A3, R¹ = R^B2, L_A198
R⁵ = R^A4, R¹ = R^B2, L_A199
R⁵ = R^A5, R¹ = R^B2, L_A200

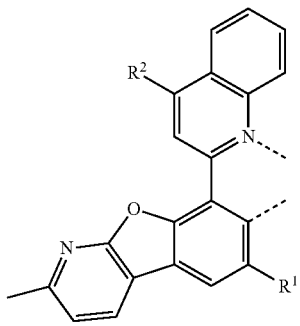

R² = R^A1, R¹ = R^B1, L_A201
R² = R^A2, R¹ = R^B1, L_A202
R² = R^A3, R¹ = R^B1, L_A203
R² = R^A4, R¹ = R^B1, L_A204
R² = R^A5, R¹ = R^B1, L_A205
R² = R^A1, R¹ = R^B2, L_A206
R² = R^A2, R¹ = R^B2, L_A207
R² = R^A3, R¹ = R^B2, L_A208
R² = R^A4, R¹ = R^B2, L_A209
R² = R^A5, R¹ = R^B2, L_A210

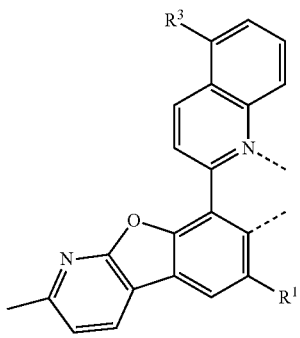

R³ = R^A1, R¹ = R^B1, L_A211
R³ = R^A2, R¹ = R^B1, L_A212
R³ = R^A3, R¹ = R^B1, L_A213
R³ = R^A4, R¹ = R^B1, L_A214
R³ = R^A5, R¹ = R^B1, L_A215
R³ = R^A1, R¹ = R^B2, L_A216
R³ = R^A2, R¹ = R^B2, L_A217
R³ = R^A3, R¹ = R^B2, L_A218
R³ = R^A4, R¹ = R^B2, L_A219
R³ = R^A5, R¹ = R^B2, L_A220

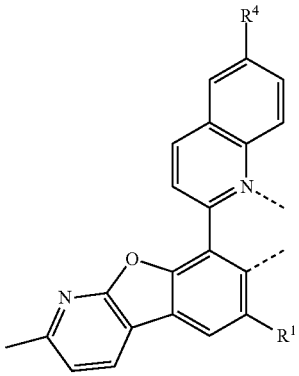

R⁴ = R^A1, R¹ = R^B1, L_A221
R⁴ = R^A2, R¹ = R^B1, L_A222
R⁴ = R^A3, R¹ = R^B1, L_A223
R⁴ = R^A4, R¹ = R^B1, L_A224
R⁴ = R^A5, R¹ = R^B1, L_A225
R⁴ = R^A1, R¹ = R^B2, L_A226
R⁴ = R^A2, R¹ = R^B2, L_A227
R⁴ = R^A3, R¹ = R^B2, L_A228
R⁴ = R^A4, R¹ = R^B2, L_A229
R⁴ = R^A5, R¹ = R^B2, L_A230

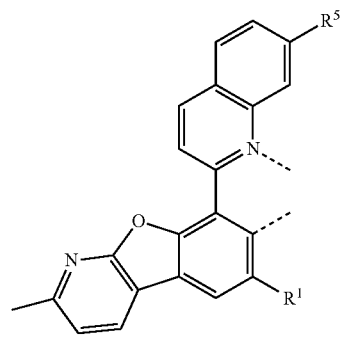

R⁵ = R^A1, R¹ = R^B1, L_A231
R⁵ = R^A2, R¹ = R^B1, L_A232
R⁵ = R^A3, R¹ = R^B1, L_A233
R⁵ = R^A4, R¹ = R^B1, L_A234
R⁵ = R^A5, R¹ = R^B1, L_A235
R⁵ = R^A1, R¹ = R^B2, L_A236
R⁵ = R^A2, R¹ = R^B2, L_A237
R⁵ = R^A3, R¹ = R^B2, L_A238
R⁵ = R^A4, R¹ = R^B2, L_A239
R⁵ = R^A5, R¹ = R^B2, L_A240

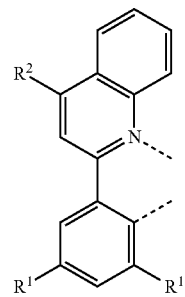

R² = R^A1, R¹ = R^B3, L_A241
R² = R^A2, R¹ = R^B3, L_A242
R² = R^A3, R¹ = R^B3, L_A243

R² = R⁴⁴, R¹ = R^B3, L_A244
R² = R⁴⁵, R¹ = R^B3, L_A245
R² = R⁴¹, R¹ = R^B4, L_A246
R² = R⁴², R¹ = R^B4, L_A247
R² = R⁴³, R¹ = R^B4, L_A248
R² = R⁴⁴, R¹ = R^B4, L_A249
R² = R⁴⁵, R¹ = R^B4, L_A250

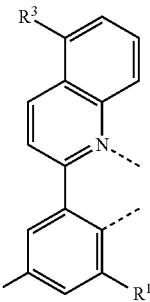

R³ = R⁴¹, R¹ = R^B3, L_A251
R³ = R⁴², R¹ = R^B3, L_A252
R³ = R⁴³, R¹ = R^B3, L_A253
R³ = R⁴⁴, R¹ = R^B3, L_A254
R³ = R⁴⁵, R¹ = R^B3, L_A255
R³ = R⁴¹, R¹ = R^B4, L_A256
R³ = R⁴², R¹ = R^B4, L_A257
R³ = R⁴³, R¹ = R^B4, L_A258
R³ = R⁴⁴, R¹ = R^B4, L_A259
R³ = R⁴⁵, R¹ = R^B4, L_A260

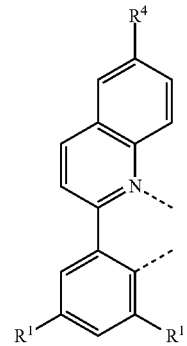

R⁴ = R⁴¹, R¹ = R^B3, L_A261
R⁴ = R⁴², R¹ = R^B3, L_A262
R⁴ = R⁴³, R¹ = R^B3, L_A263
R⁴ = R⁴⁴, R¹ = R^B3, L_A264
R⁴ = R⁴⁵, R¹ = R^B3, L_A265
R⁴ = R⁴¹, R¹ = R^B4, L_A266
R⁴ = R⁴², R¹ = R^B4, L_A267
R⁴ = R⁴³, R¹ = R^B4, L_A268
R⁴ = R⁴⁴, R¹ = R^B4, L_A269
R⁴ = R⁴⁵, R¹ = R^B4, L_A270

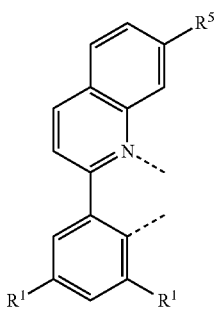

R⁵ = R⁴¹, R¹ = R^B3, L_A271
R⁵ = R⁴², R¹ = R^B3, L_A272
R⁵ = R⁴³, R¹ = R^B3, L_A273
R⁵ = R⁴⁴, R¹ = R^B3, L_A274
R⁵ = R⁴⁵, R¹ = R^B3, L_A275
R⁵ = R⁴¹, R¹ = R^B4, L_A276
R⁵ = R⁴², R¹ = R^B4, L_A277
R⁵ = R⁴³, R¹ = R^B4, L_A278
R⁵ = R⁴⁴, R¹ = R^B4, L_A279
R⁵ = R⁴⁵, R¹ = R^B4, L_A280

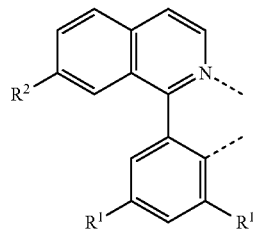

R² = R⁴¹, R¹ = R^B3, L_A281
R² = R⁴², R¹ = R^B3, L_A282
R² = R⁴³, R¹ = R^B3, L_A283
R² = R⁴⁴, R¹ = R^B3, L_A284
R² = R⁴⁵, R¹ = R^B3, L_A285
R² = R⁴¹, R¹ = R^B4, L_A286
R² = R⁴², R¹ = R^B4, L_A287
R² = R⁴³, R¹ = R^B4, L_A288
R² = R⁴⁴, R¹ = R^B4, L_A289
R² = R⁴⁵, R¹ = R^B4, L_A290

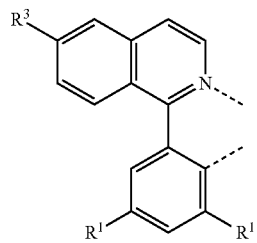

R³ = R⁴¹, R¹ = R^B3, L_A291
R³ = R⁴², R¹ = R^B3, L_A292
R³ = R⁴³, R¹ = R^B3, L_A293
R³ = R⁴⁴, R¹ = R^B3, L_A294
R³ = R⁴⁵, R¹ = R^B3, L_A295
R³ = R⁴¹, R¹ = R^B4, L_A296
R³ = R⁴², R¹ = R^B4, L_A297
R³ = R⁴³, R¹ = R^B4, L_A298
R³ = R⁴⁴, R¹ = R^B4, L_A299
R³ = R⁴⁵, R¹ = R^B4, L_A300

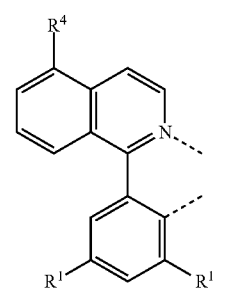

R⁴ = R⁴¹, R¹ = R^B3, L_A301
R⁴ = R⁴², R¹ = R^B3, L_A302
R⁴ = R⁴³, R¹ = R^B3, L_A303
R⁴ = R⁴⁴, R¹ = R^B3, L_A304
R⁴ = R⁴⁵, R¹ = R^B3, L_A305
R⁴ = R⁴¹, R¹ = R^B4, L_A306
R⁴ = R⁴², R¹ = R^B4, L_A307
R⁴ = R⁴³, R¹ = R^B4, L_A308
R⁴ = R⁴⁴, R¹ = R^B4, L_A309
R⁴ = R⁴⁵, R¹ = R^B4, L_A310

-continued

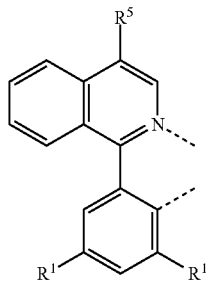

R⁵ = R^A1, R¹ = R^B3, L_A311
R⁵ = R^A2, R¹ = R^B3, L_A312
R⁵ = R^A3, R¹ = R^B3, L_A313
R⁵ = R^A4, R¹ = R^B3, L_A314
R⁵ = R^A5, R¹ = R^B3, L_A315
R⁵ = R^A1, R¹ = R^B4, L_A316
R⁵ = R^A2, R¹ = R^B4, L_A317
R⁵ = R^A3, R¹ = R^B4, L_A318
R⁵ = R^A4, R¹ = R^B4, L_A319
R⁵ = R^A5, R¹ = R^B4, L_A320

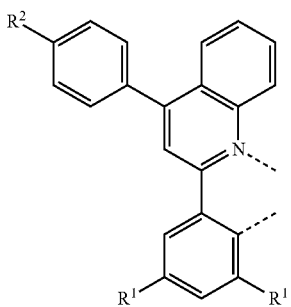

R² = R^A1, R¹ = R^B3, L_A321
R² = R^A2, R¹ = R^B3, L_A322
R² = R^A3, R¹ = R^B3, L_A323
R² = R^A4, R¹ = R^B3, L_A324
R² = R^A5, R¹ = R^B3, L_A325
R² = R^A1, R¹ = R^B4, L_A326
R² = R^A2, R¹ = R^B4, L_A327
R² = R^A3, R¹ = R^B4, L_A328
R² = R^A4, R¹ = R^B4, L_A329
R² = R^A5, R¹ = R^B4, L_A330

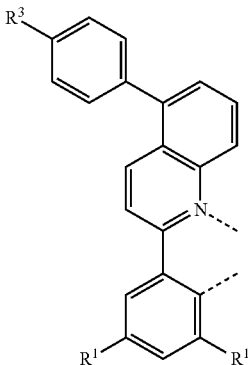

R³ = R^A1, R¹ = R^B3, L_A331
R³ = R^A2, R¹ = R^B3, L_A332
R³ = R^A3, R¹ = R^B3, L_A333
R³ = R^A4, R¹ = R^B3, L_A334
R³ = R^A5, R¹ = R^B3, L_A335
R³ = R^A1, R¹ = R^B4, L_A336
R³ = R^A2, R¹ = R^B4, L_A337
R³ = R^A3, R¹ = R^B4, L_A338

R³ = R^A4, R¹ = R^B4, L_A339
R³ = R^A5, R¹ = R^B4, L_A340

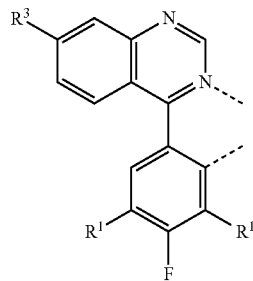

R⁴ = R^A1, R¹ = R^B3, L_A341
R⁴ = R^A2, R¹ = R^B3, L_A342
R⁴ = R^A3, R¹ = R^B3, L_A343
R⁴ = R^A4, R¹ = R^B3, L_A344
R⁴ = R^A5, R¹ = R^B3, L_A345
R⁴ = R^A1, R¹ = R^B4, L_A346
R⁴ = R^A2, R¹ = R^B4, L_A347
R⁴ = R^A3, R¹ = R^B4, L_A348
R⁴ = R^A4, R¹ = R^B4, L_A349
R⁴ = R^A5, R¹ = R^B4, L_A350

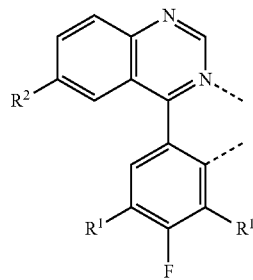

R⁵ = R^A1, R¹ = R^B3, L_A351
R⁵ = R^A2, R¹ = R^B3, L_A352
R⁵ = R^A3, R¹ = R^B3, L_A353
R⁵ = R^A4, R¹ = R^B3, L_A354
R⁵ = R^A5, R¹ = R^B3, L_A355
R⁵ = R^A1, R¹ = R^B4, L_A356
R⁵ = R^A2, R¹ = R^B4, L_A357
R⁵ = R^A3, R¹ = R^B4, L_A358
R⁵ = R^A4, R¹ = R^B4, L_A359
R⁵ = R^A5, R¹ = R^B4, L_A360

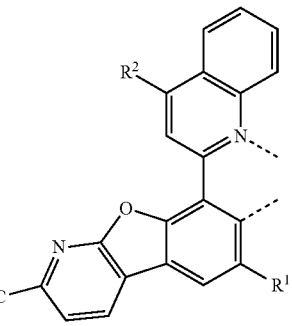

R² = R^A1, R¹ = R^B3, L_A361
R² = R^A2, R¹ = R^B3, L_A362
R² = R^A3, R¹ = R^B3, L_A363
R² = R^A4, R¹ = R^B3, L_A364
R² = R^A5, R¹ = R^B3, L_A365
R² = R^A1, R¹ = R^B4, L_A366
R² = R^A2, R¹ = R^B4, L_A367
R² = R^A3, R¹ = R^B4, L_A368
R² = R^A4, R¹ = R^B4, L_A369
R² = R^A5, R¹ = R^B4, L_A370

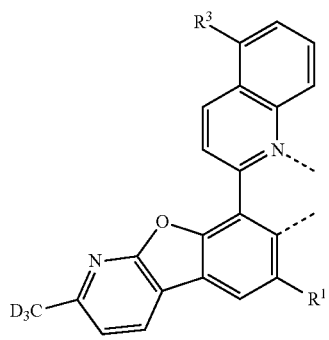

R³ = R⁴¹, R¹ = R^B³, L_{A371}
R³ = R⁴², R¹ = R^B³, L_{A372}
R³ = R⁴³, R¹ = R^B³, L_{A373}
R³ = R⁴⁴, R¹ = R^B³, L_{A374}
R³ = R⁴⁵, R¹ = R^B³, L_{A375}
R³ = R⁴¹, R¹ = R^B⁴, L_{A376}
R³ = R⁴², R¹ = R^B⁴, L_{A377}
R³ = R⁴³, R¹ = R^B⁴, L_{A378}
R³ = R⁴⁴, R¹ = R^B⁴, L_{A379}
R³ = R⁴⁵, R¹ = R^B⁴, L_{A380};

wherein $R^{41}$ to $R^{45}$, and $R^{B1}$ to $R^{B4}$ have the following structures:

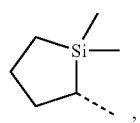 $R^{41}$

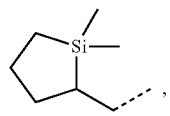 $R^{42}$

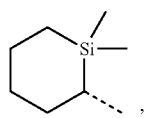 $R^{43}$

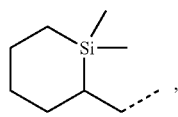 $R^{44}$

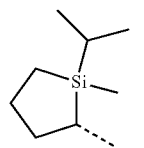 $R^{45}$

 $R^{B1}$

 $R^{B2}$

 $R^{B3}$

 $R^{B4}$

In another embodiment, the compound is selected from the group consisting of Compound 1 through Compound 4940; wherein Compound x has the formula $M(L_{Ai})_2(L_{Cj})$;

wherein x=380j+i−380, i is an integer from 1 to 380, and j is an integer from 1 to 13; and wherein $L_{Cj}$ has the following formula:

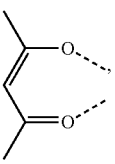 $L_{C1}$

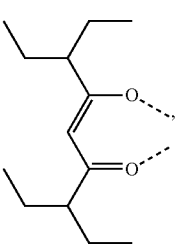 $L_{C2}$

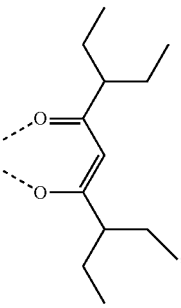 $L_{C3}$

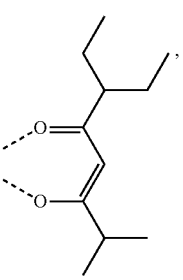 $L_{C4}$

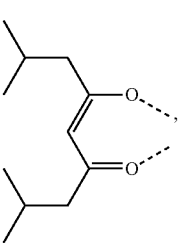 $L_{C5}$

L<sub>C6</sub> 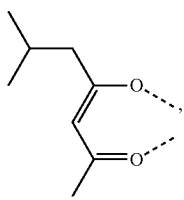

L<sub>C7</sub> 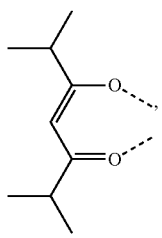

L<sub>C8</sub> 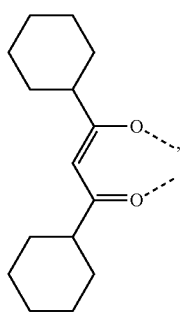

L<sub>C9</sub> 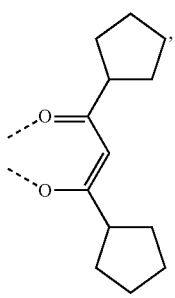

L<sub>C10</sub> 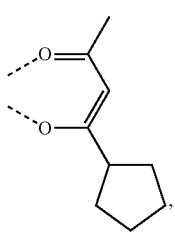

L<sub>C11</sub> 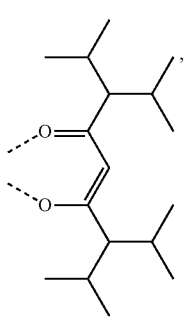

L<sub>C12</sub> 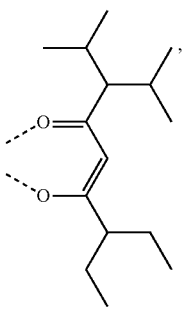 or

L<sub>C13</sub> 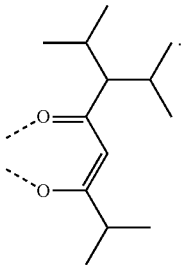

In one embodiment, the compound is capable of functioning as a phosphorescent emitter in an organic light emitting device at room temperature. In one embodiment, the compound is capable of functioning as a fluorescent emitter in an organic light emitting device at room temperature. In one embodiment, the compound is capable of functioning as a delayed fluorescent emitter in an organic light emitting device at room temperature. In one embodiment, the first compound is capable of emitting light from a triplet excited state to a ground singlet state at room temperature.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

According to another aspect of the present disclosure, an OLED is also provided. The OLED includes an anode, a cathode, and an organic layer disposed between the anode and the cathode. The organic layer may include a host and a phosphorescent dopant. The organic layer can include a compound of the invention and its variations as described herein.

The OLED can be incorporated into one or more of a consumer product, an electronic component module, and a lighting panel. The organic layer can be an emissive layer and the first compound can be an emissive dopant in some embodiments, while the first compound can be a non-emissive dopant in other embodiments.

According to another aspect of the present disclosure, a consumer product comprising an OLED is provided. The OLED may include an anode, a cathode, and an organic layer disposed between the anode and the cathode. The organic layer may include a host and one or more emitter dopants. In one embodiment, the organic layer includes a first compound.

Non-limiting examples of consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays that are less than 2 inches diagonal, 3-D displays, virtual reality or augmented reality displays, vehicles, video walls comprising multiple displays tiled together, theater or stadium screens, and/or signs.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

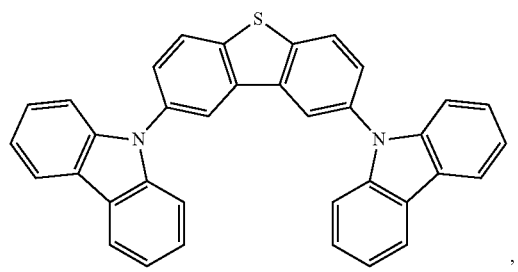

,

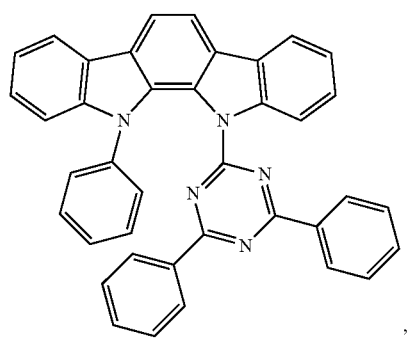

,

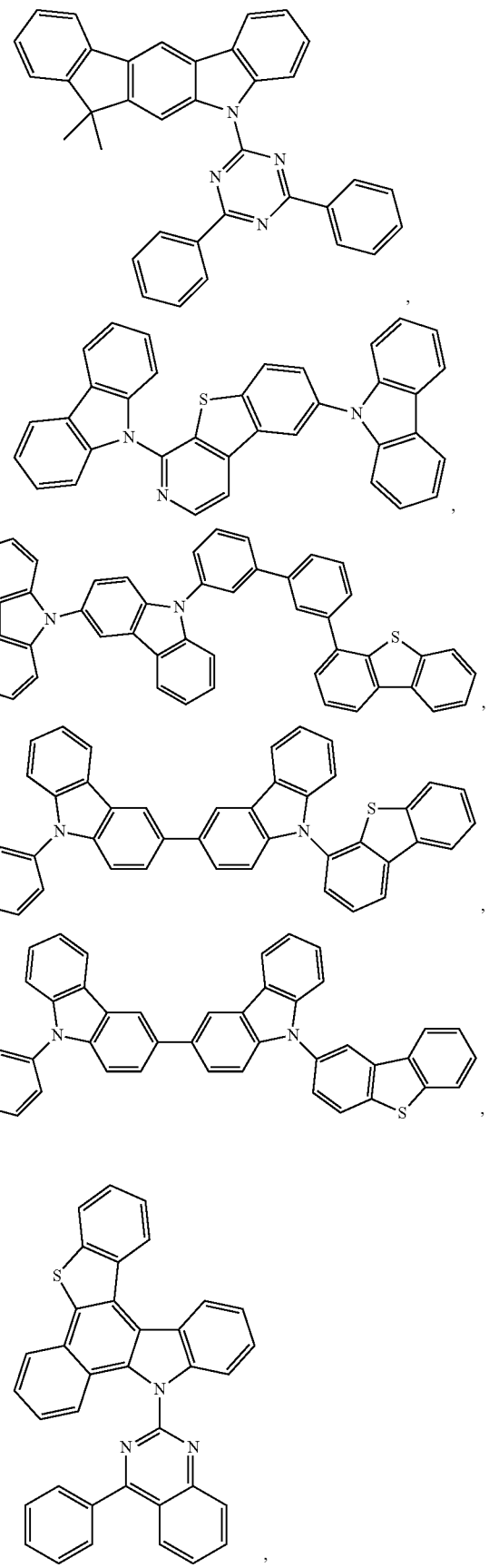

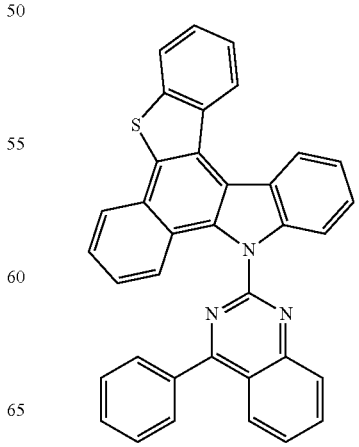

,

-continued
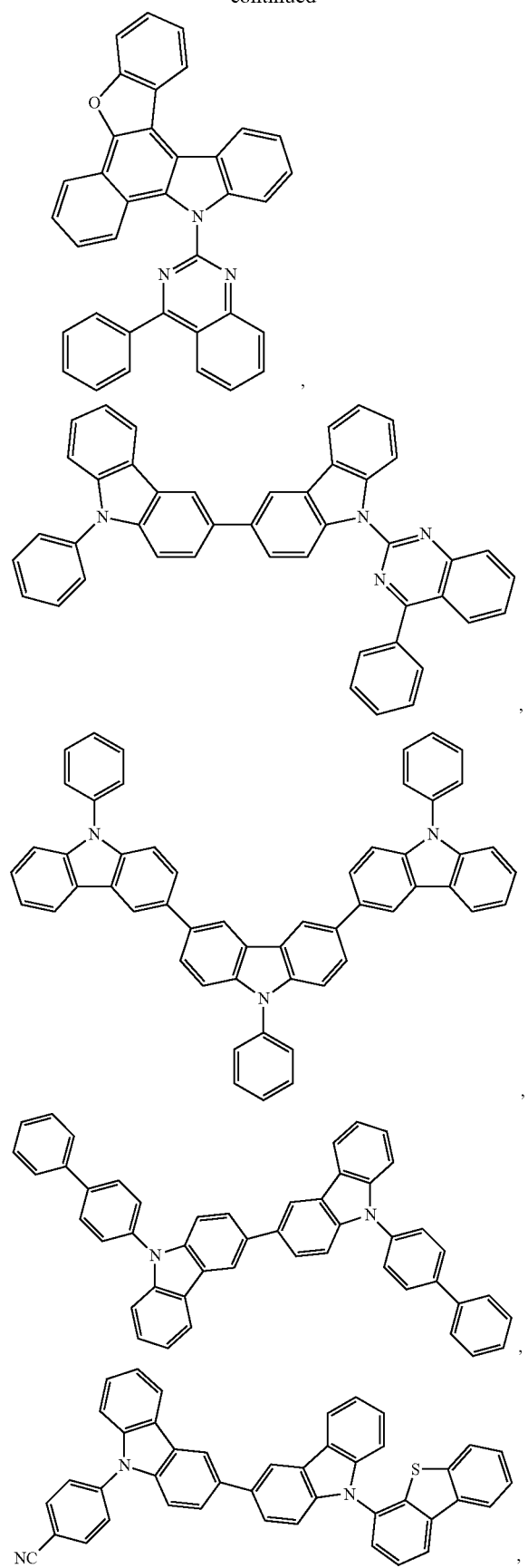
-continued
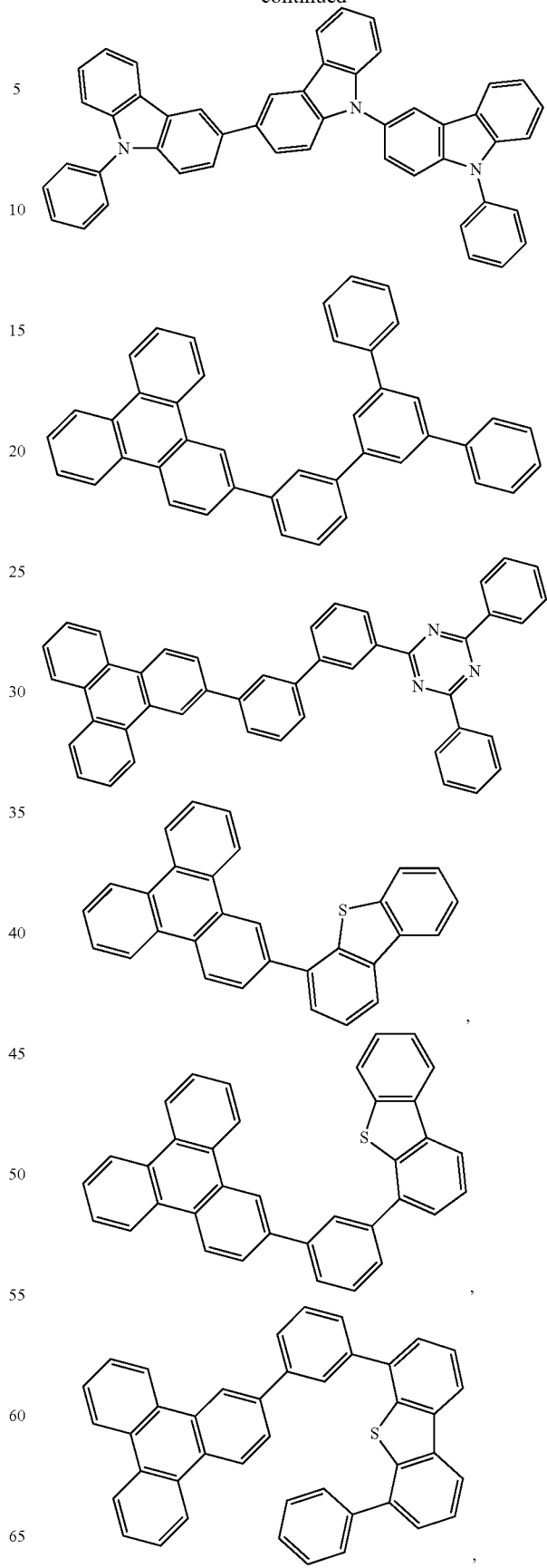

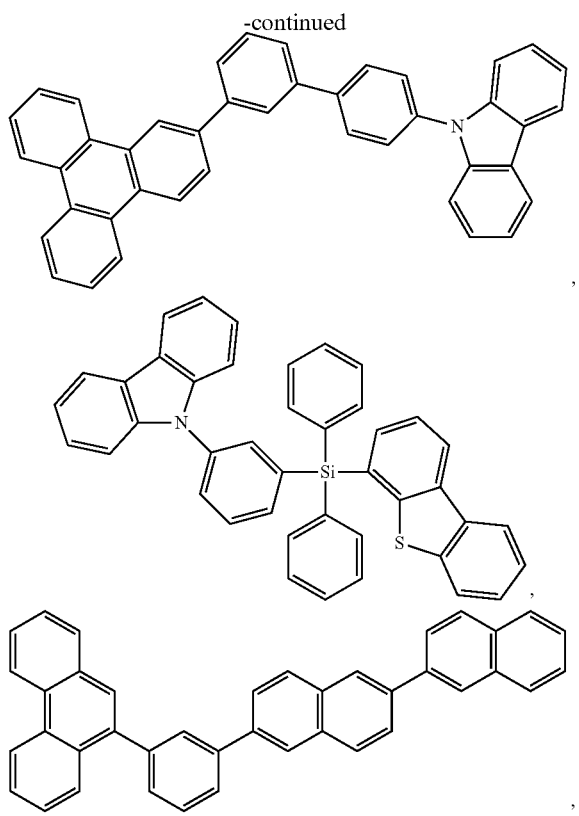

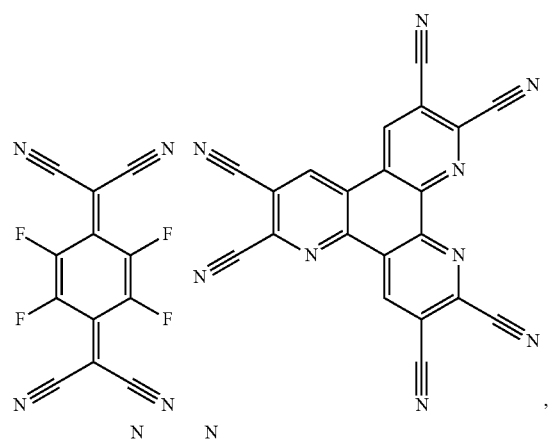

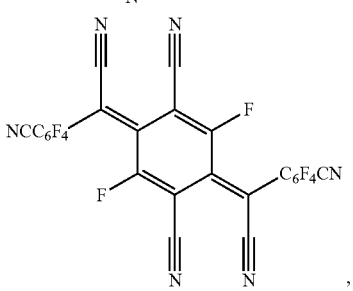

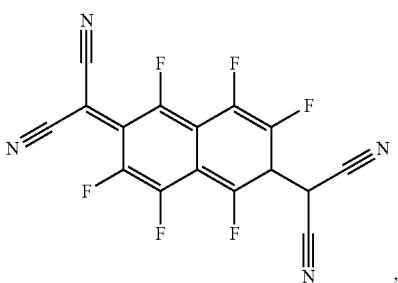

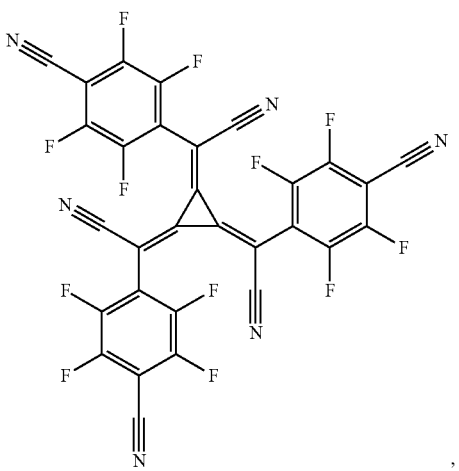

EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

and combinations thereof.
Additional information on possible hosts is provided below.

In yet another aspect of the present disclosure, a formulation that comprises a compound of the invention is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, -continued

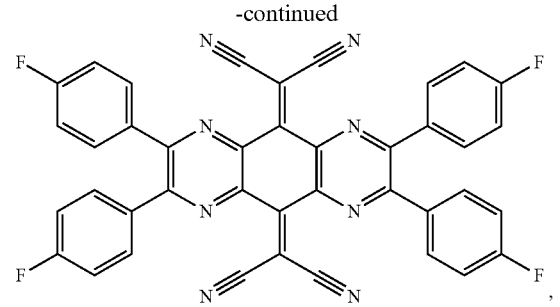,

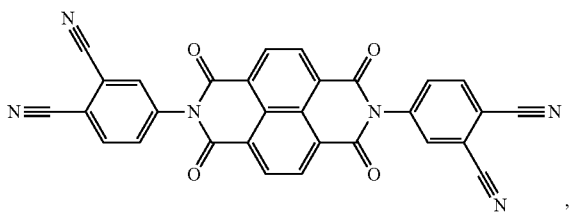,

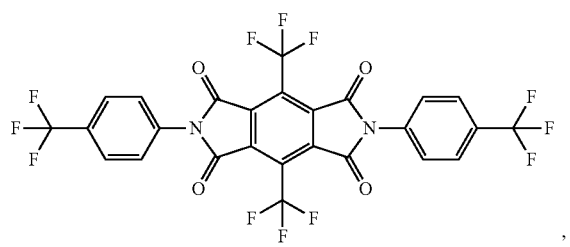,

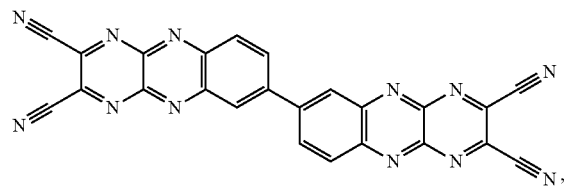,

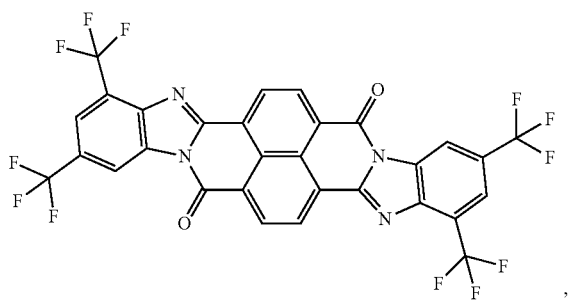,

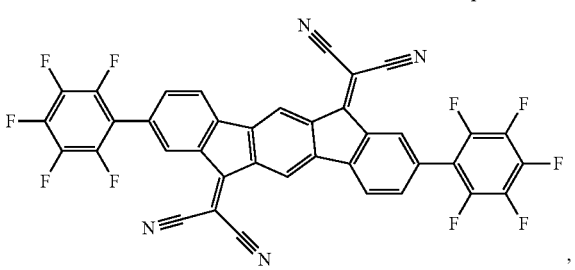,

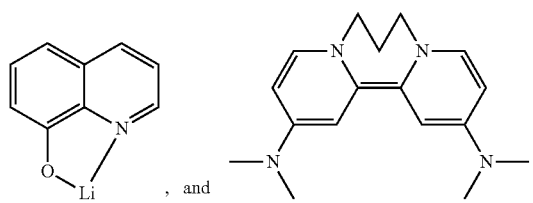, and

-continued

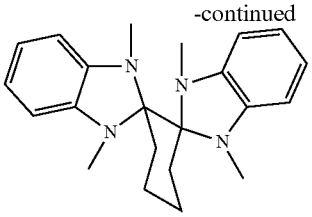

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

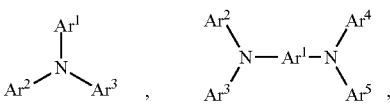

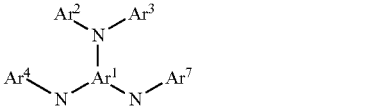

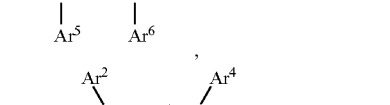

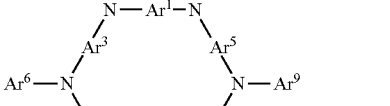, and

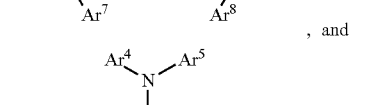

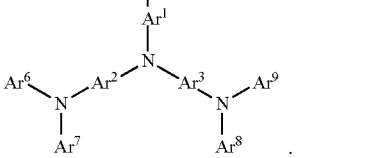

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $A^9$ is independently selected from the group consisting of:

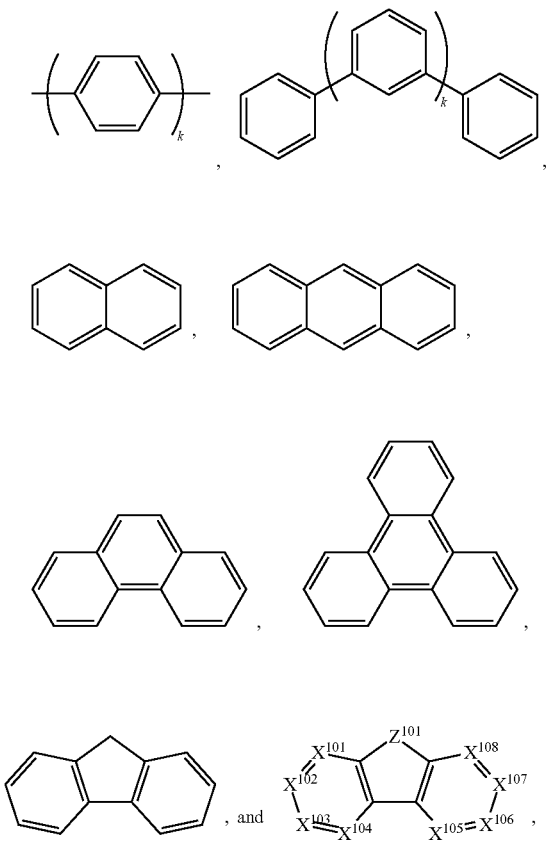

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

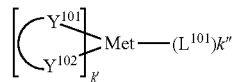

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+$/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

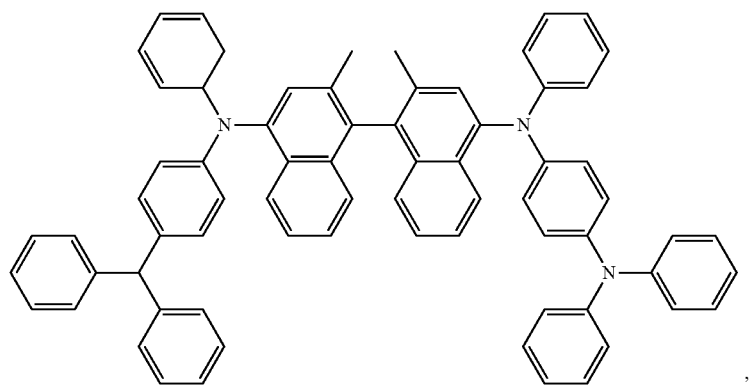
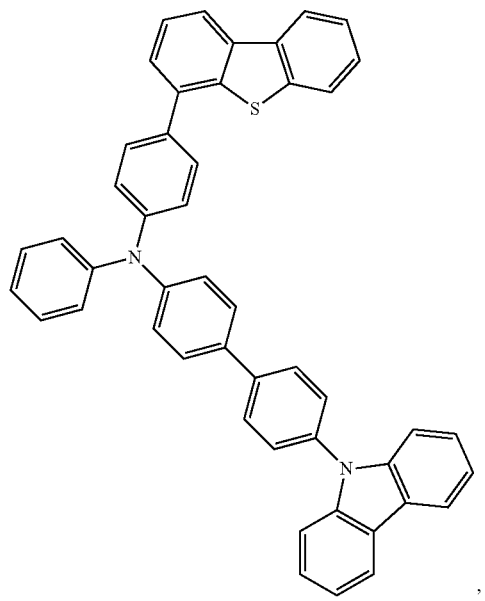
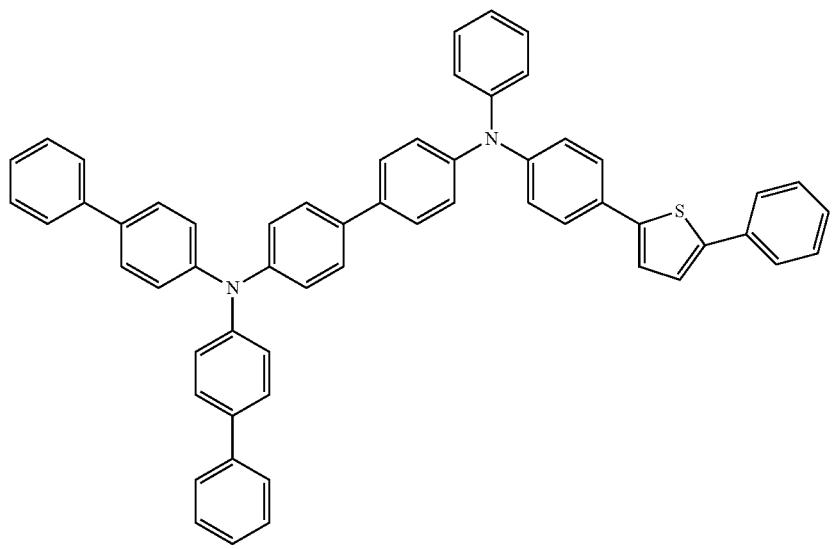

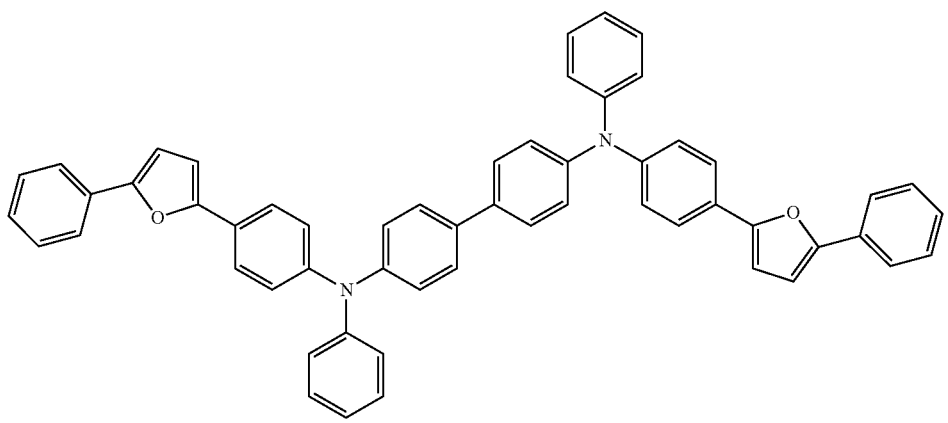
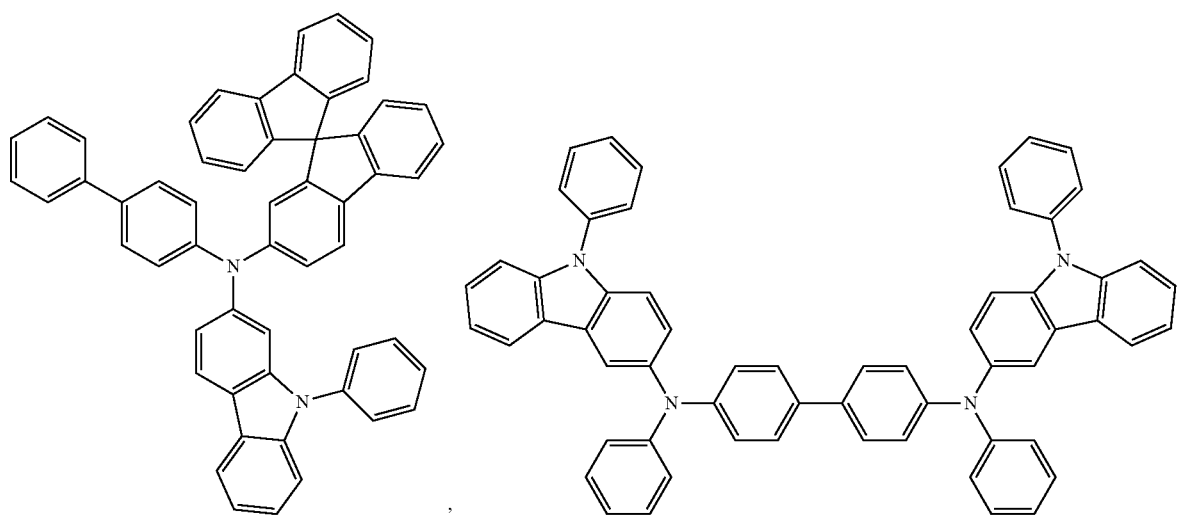
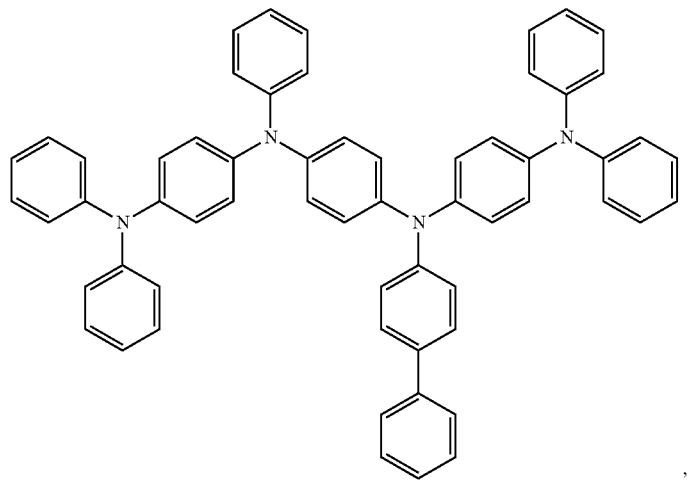

-continued
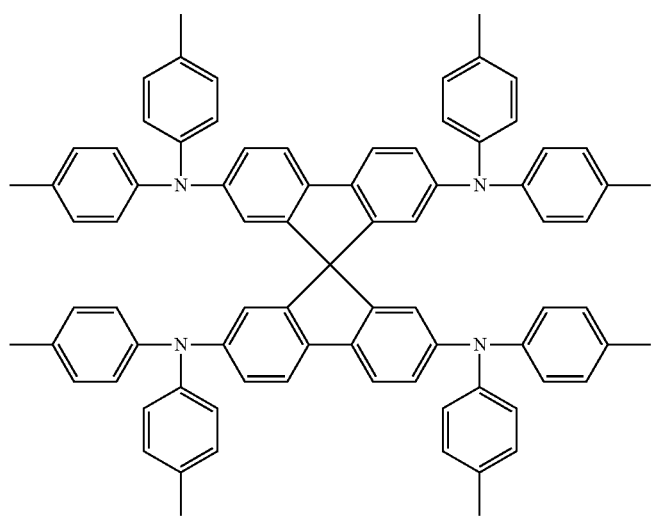
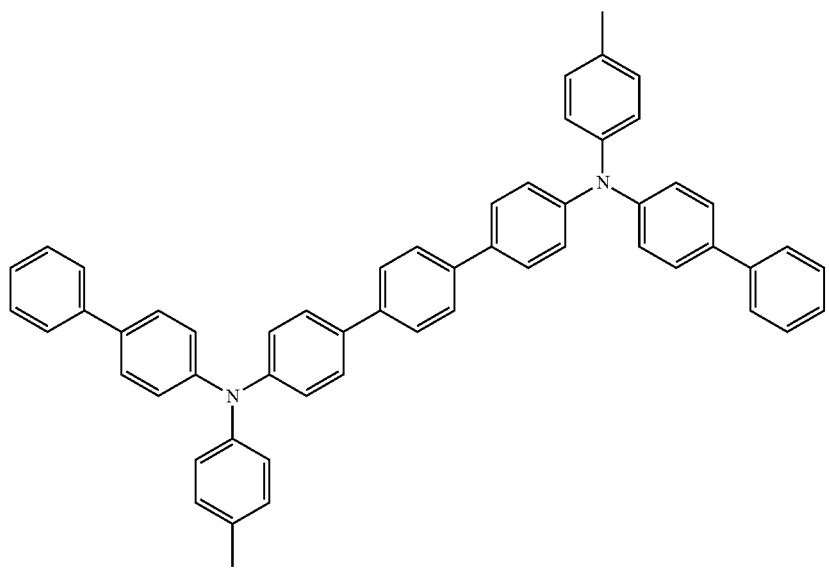

-continued
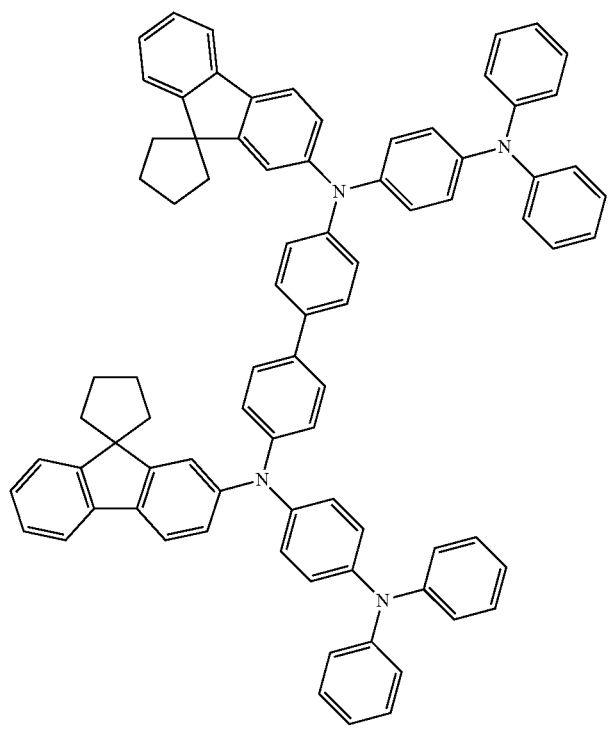
,
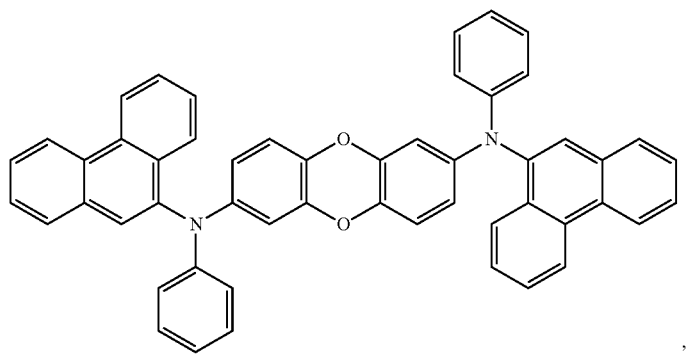
,
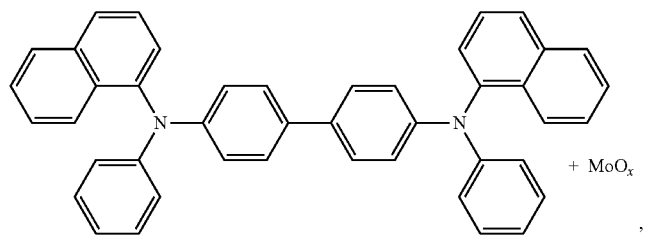 + MoO$_x$
,

-continued
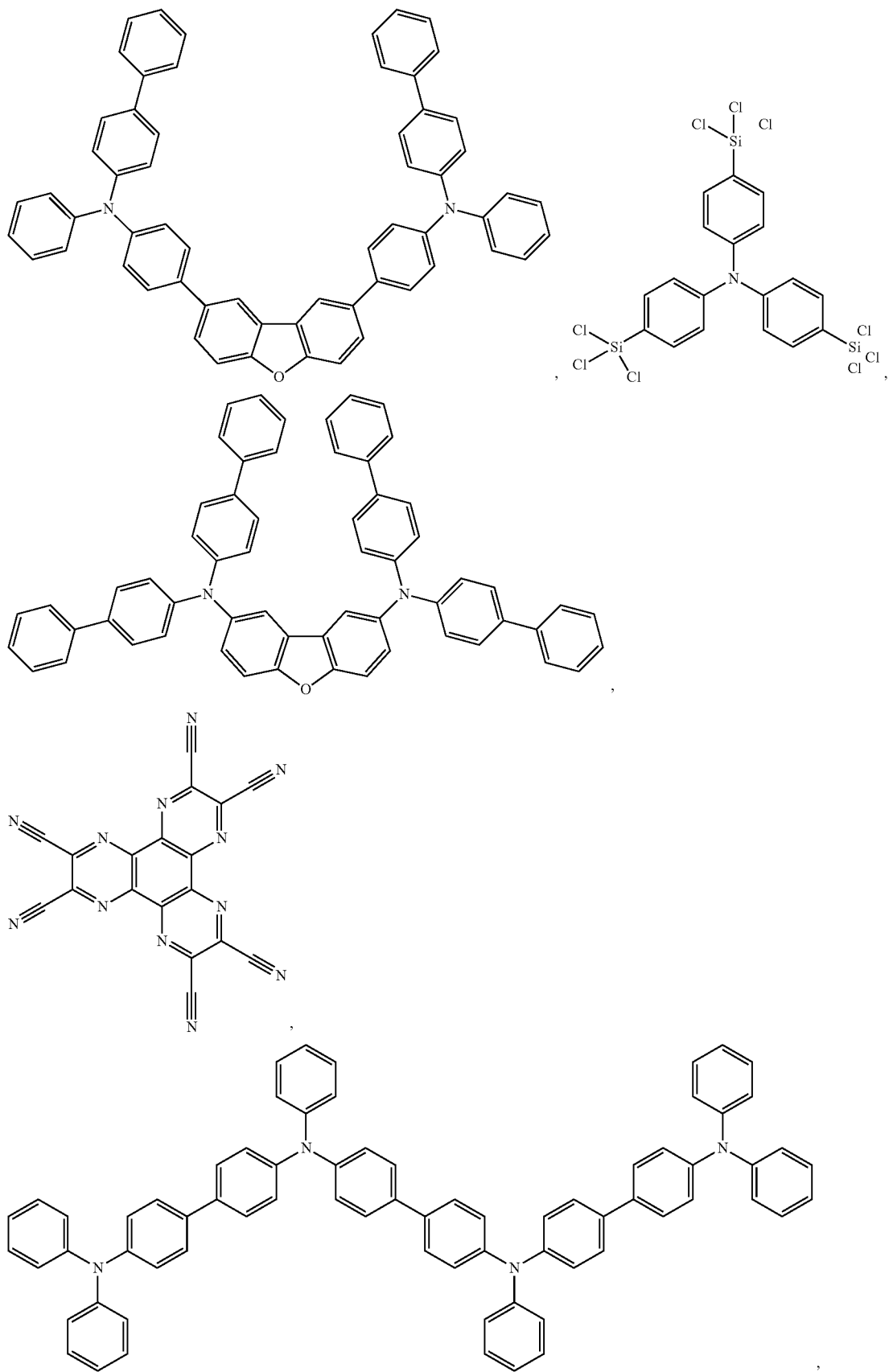

-continued
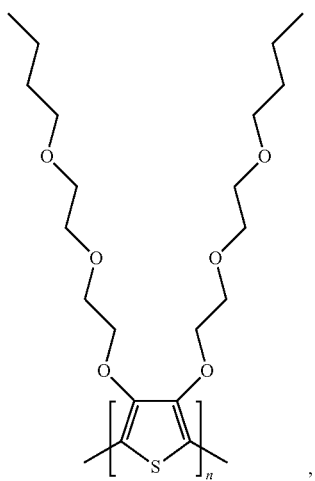
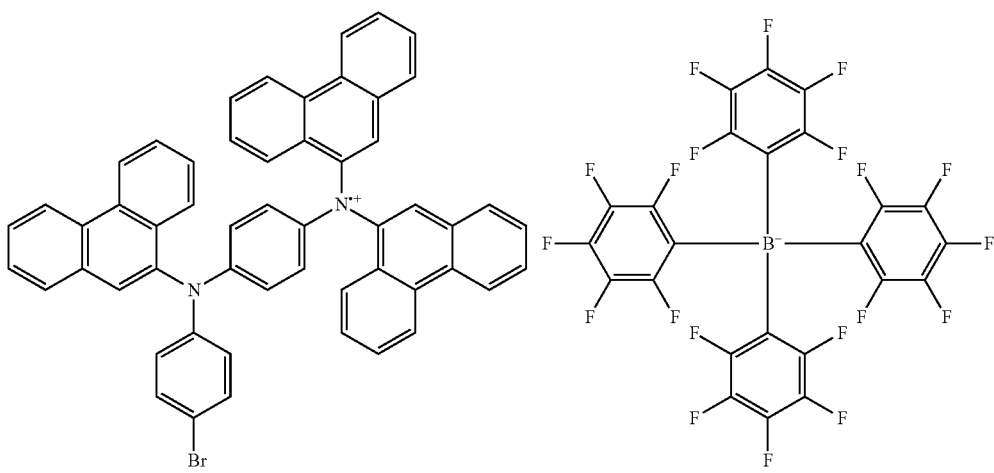
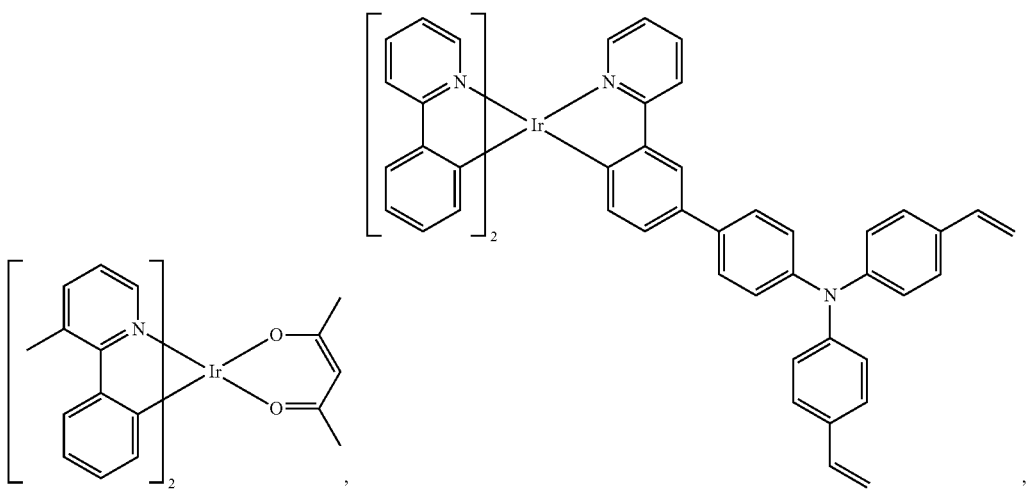

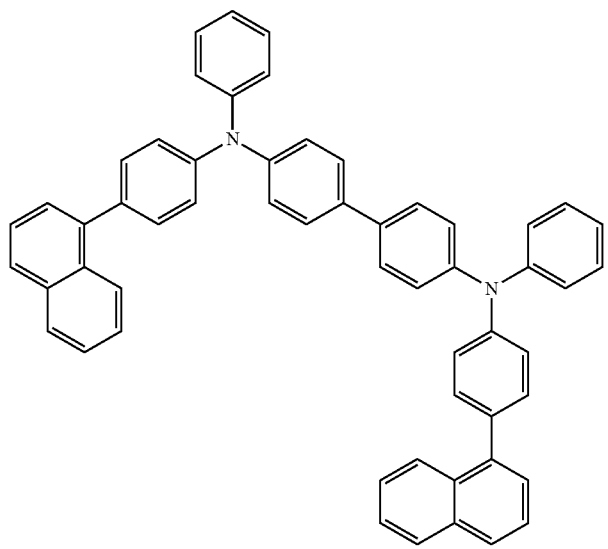
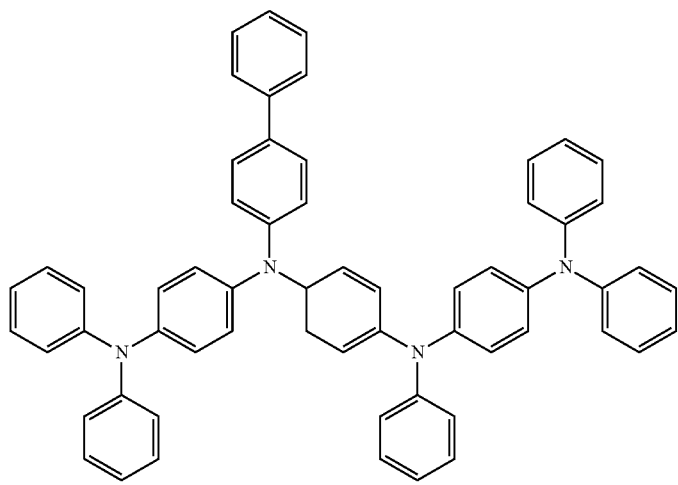
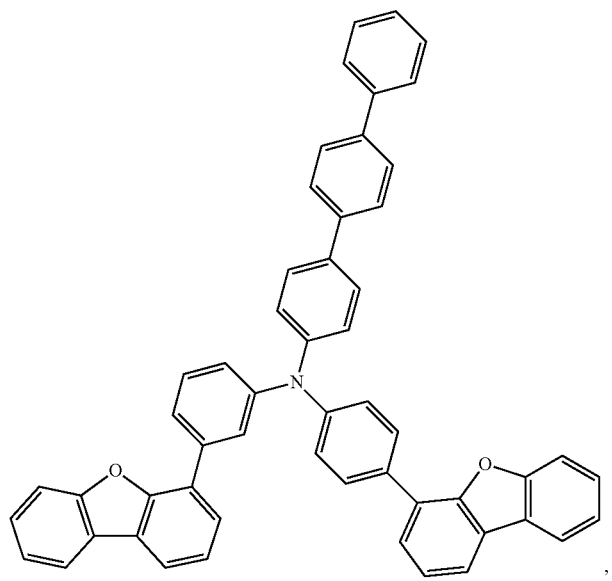

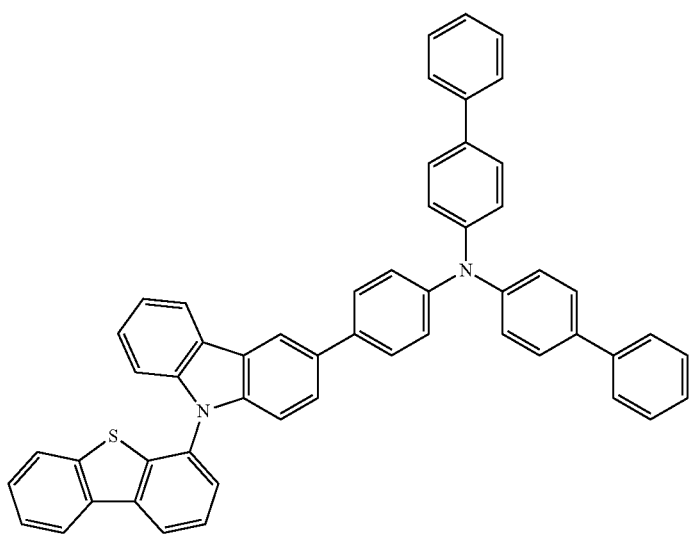
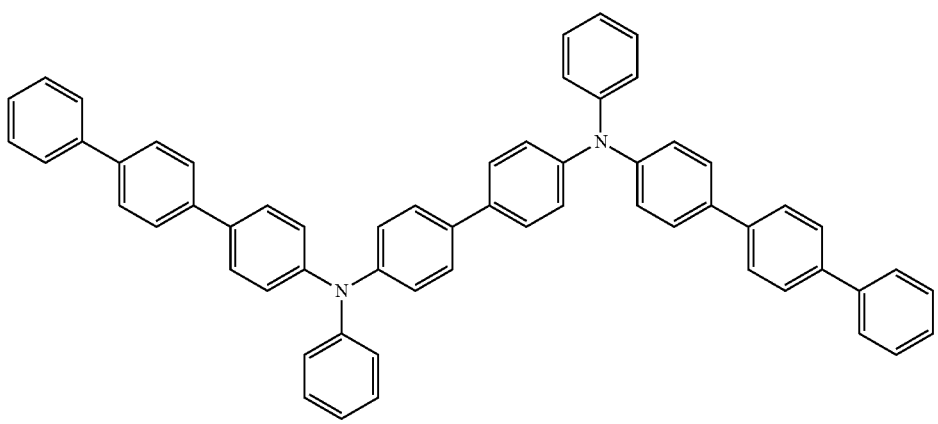
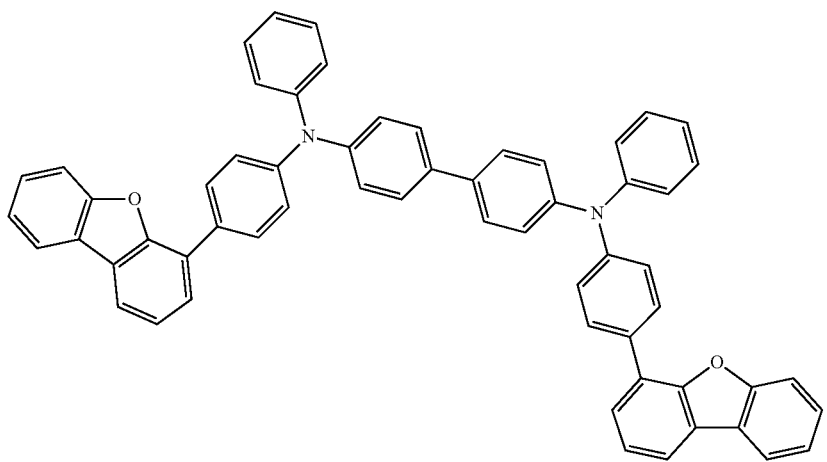

-continued
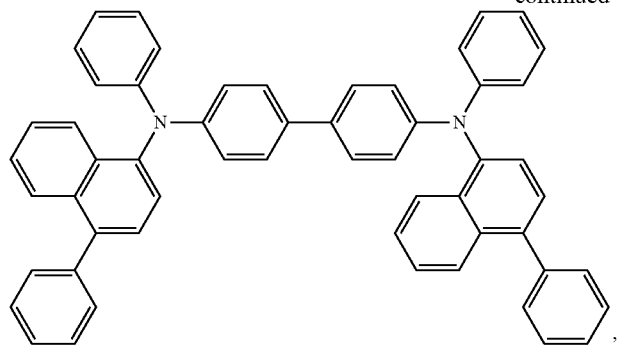
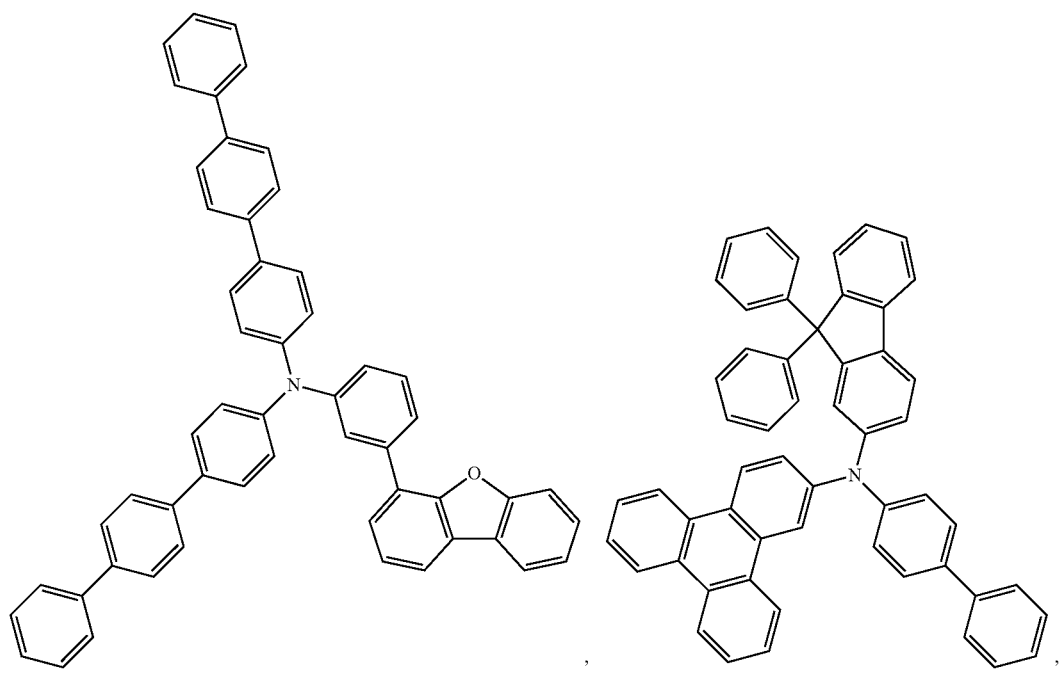
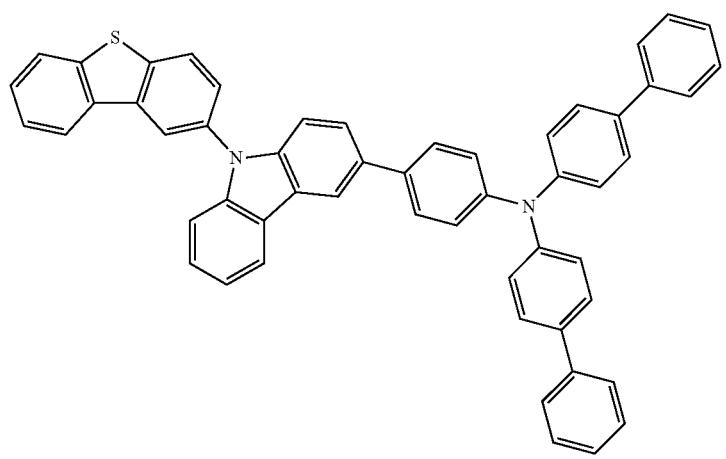

73
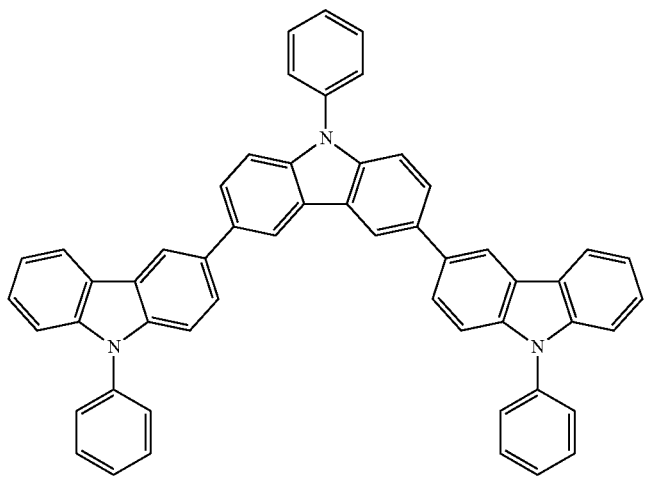
74
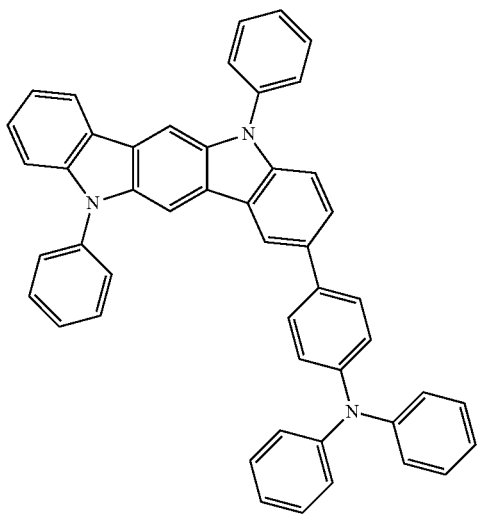
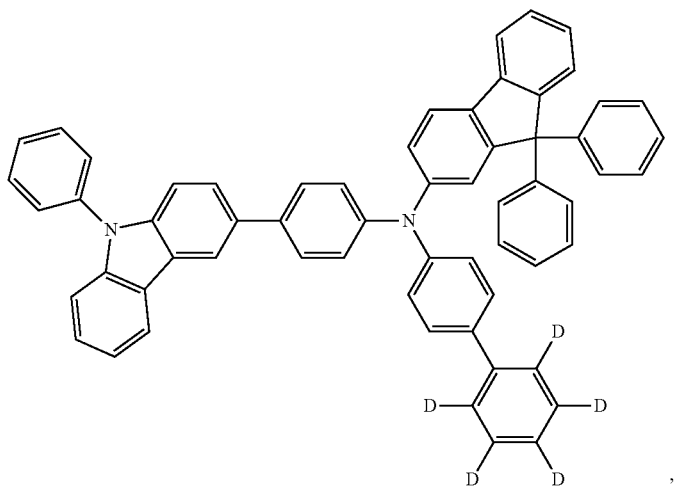
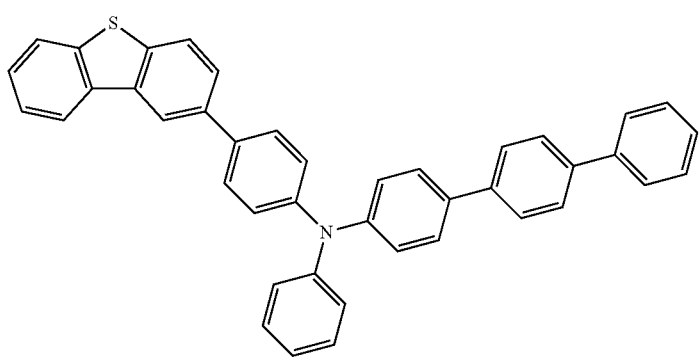

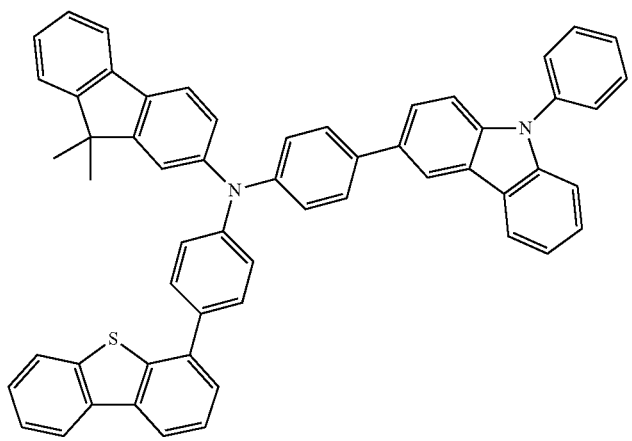
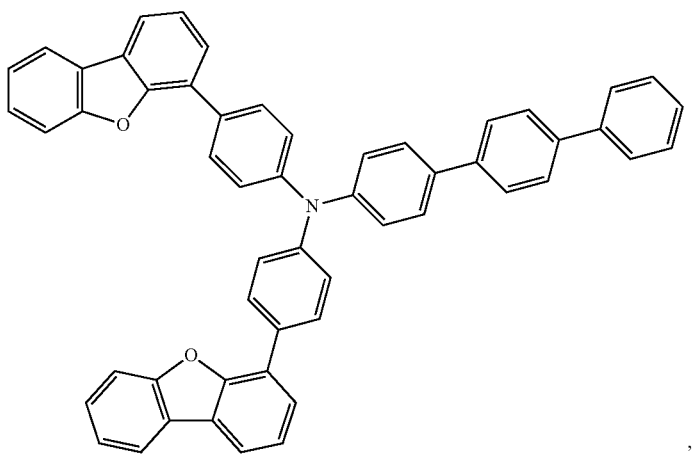
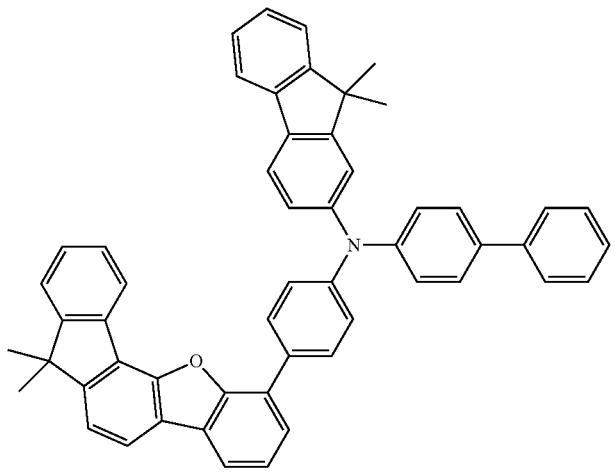

-continued
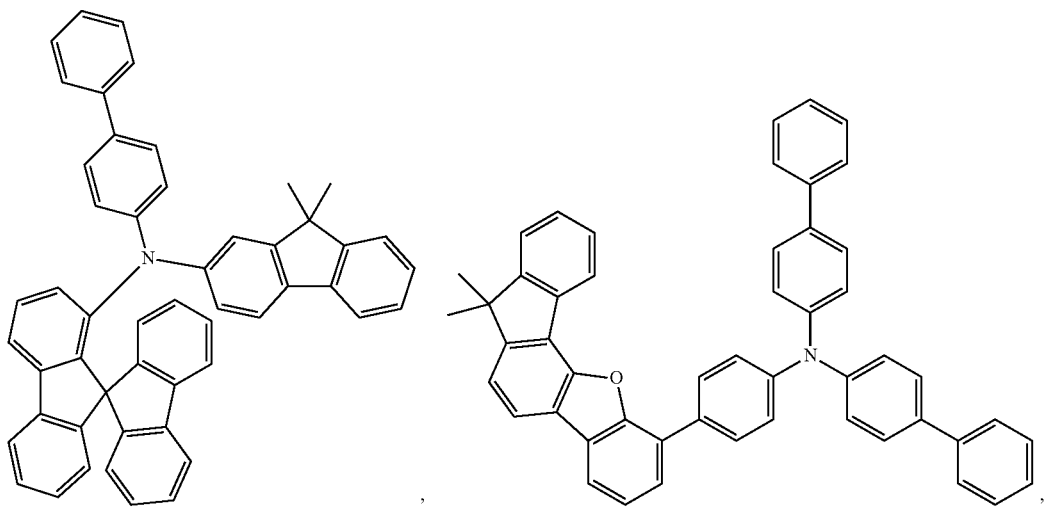
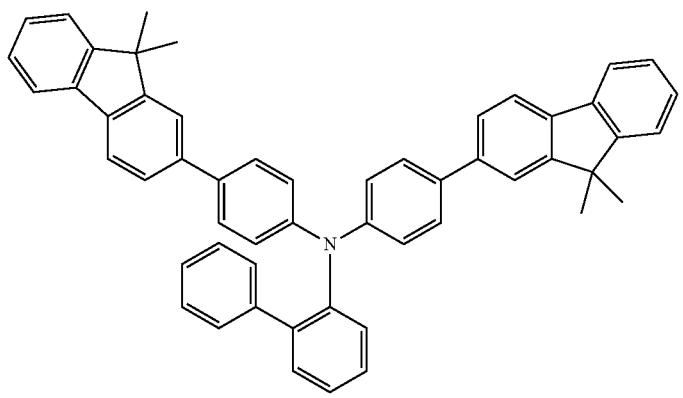
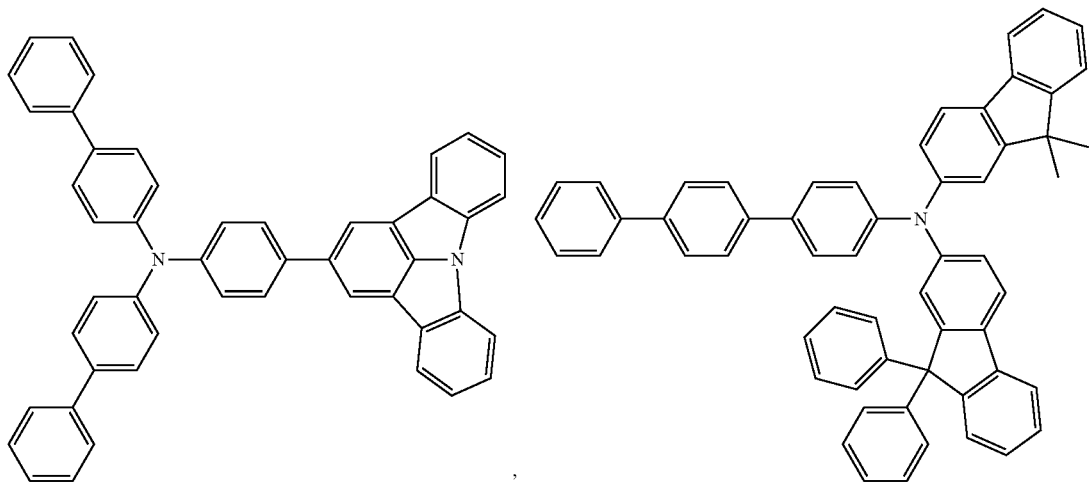

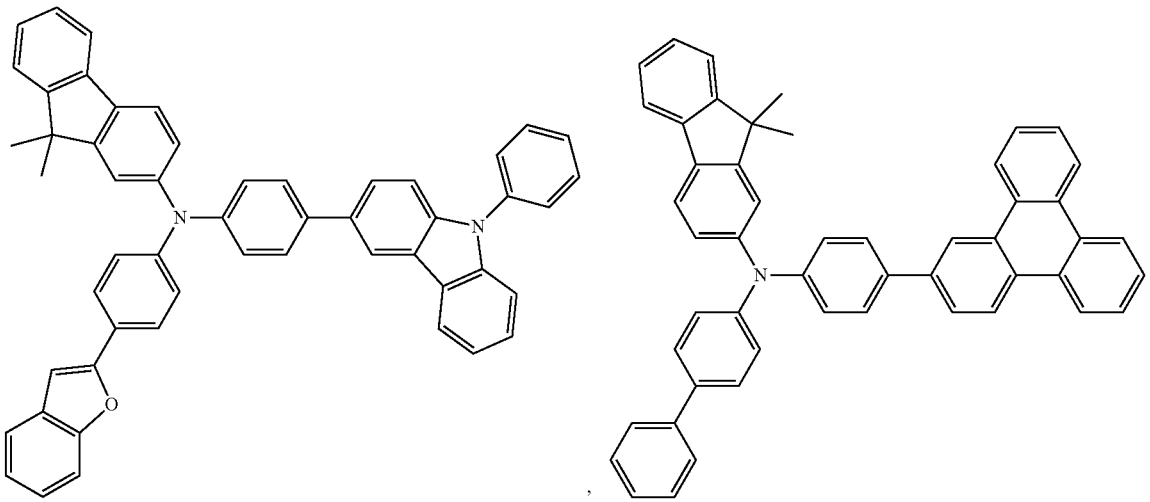
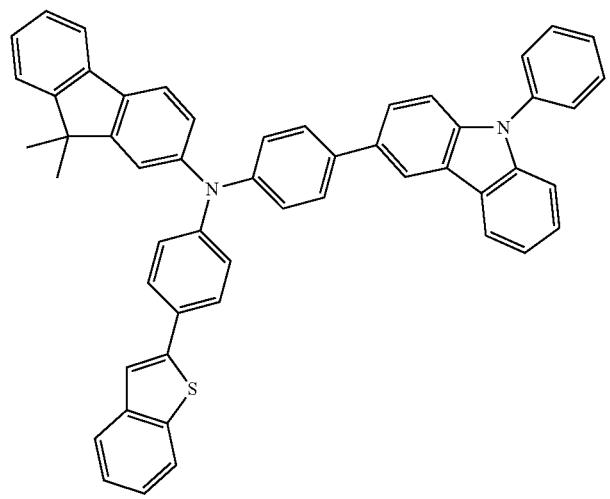
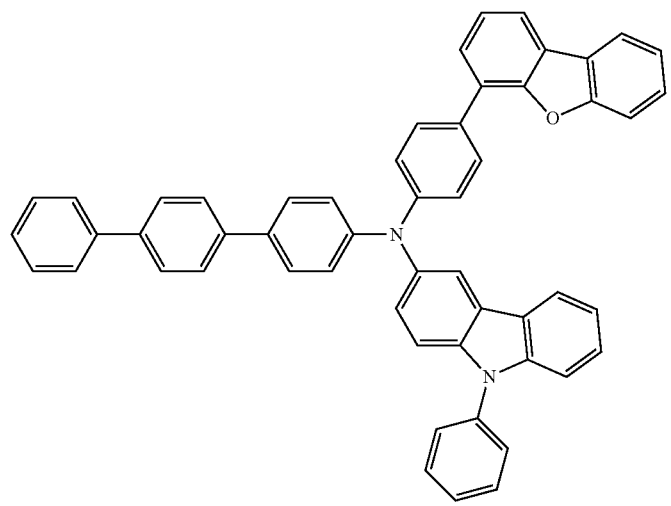

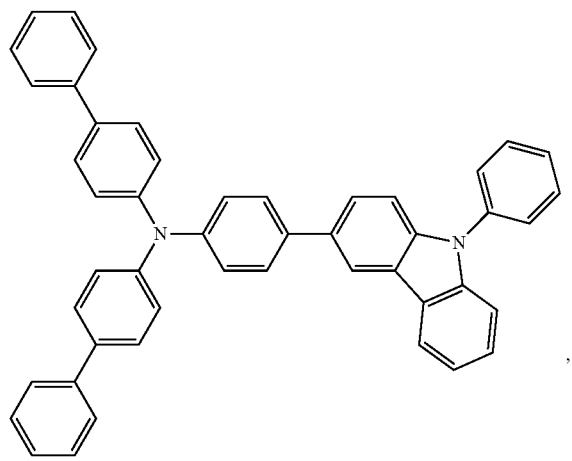
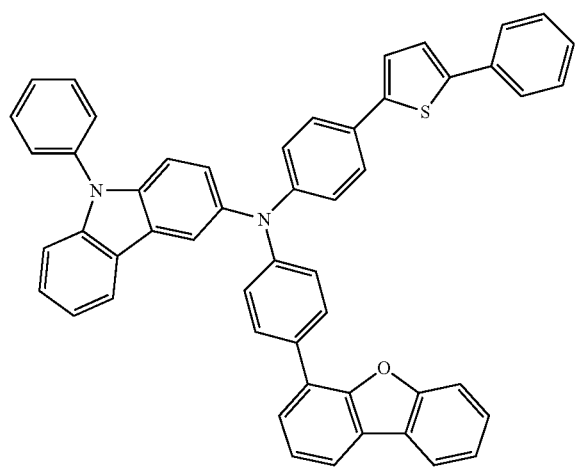
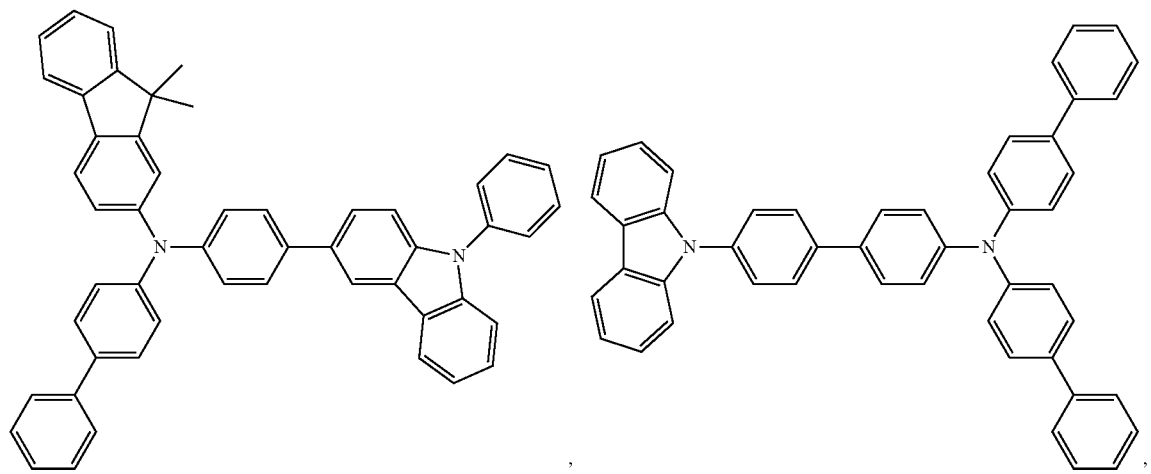

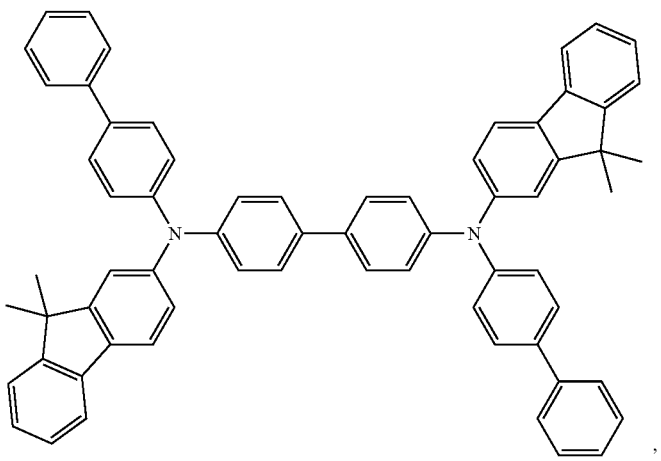
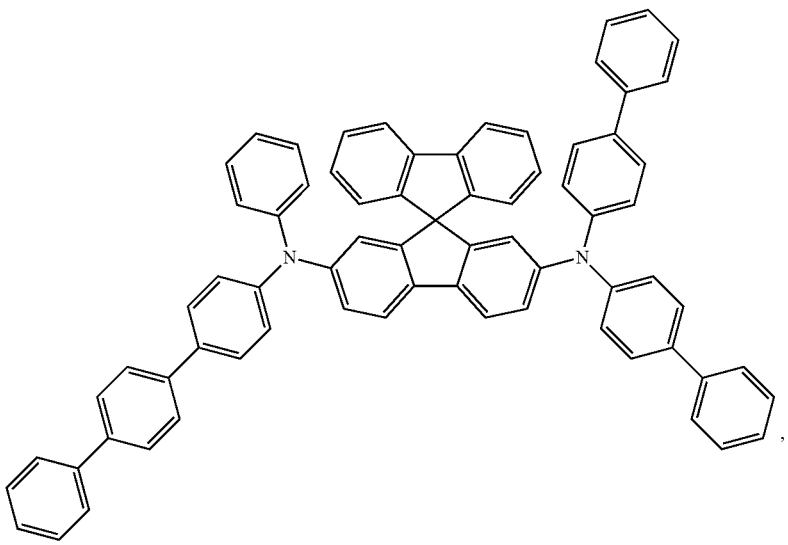
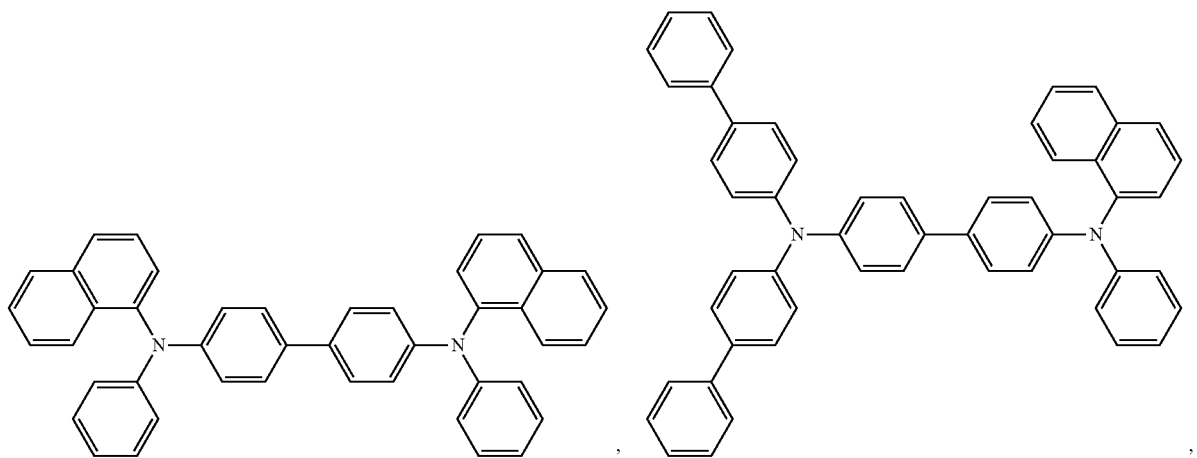

-continued
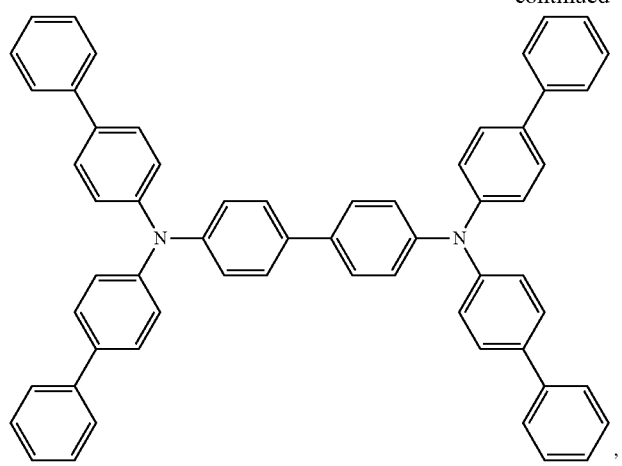
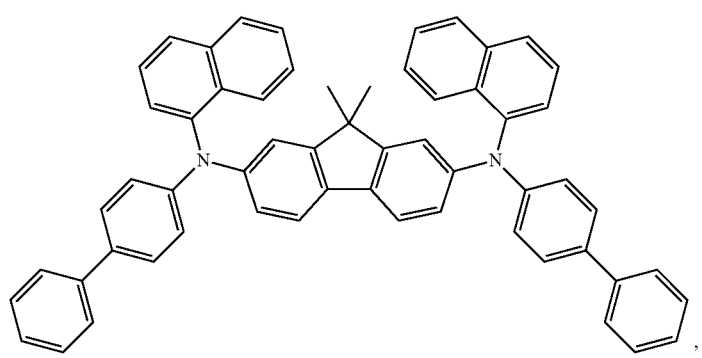
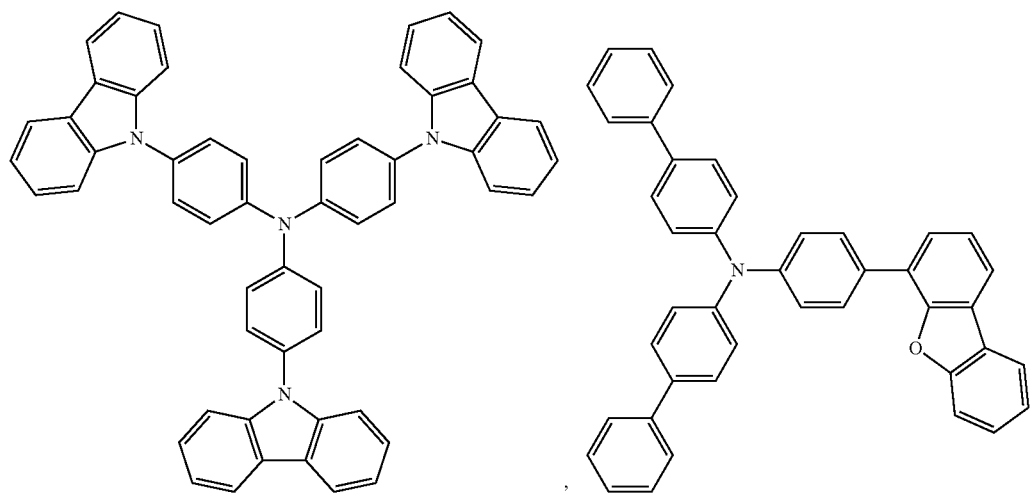

-continued
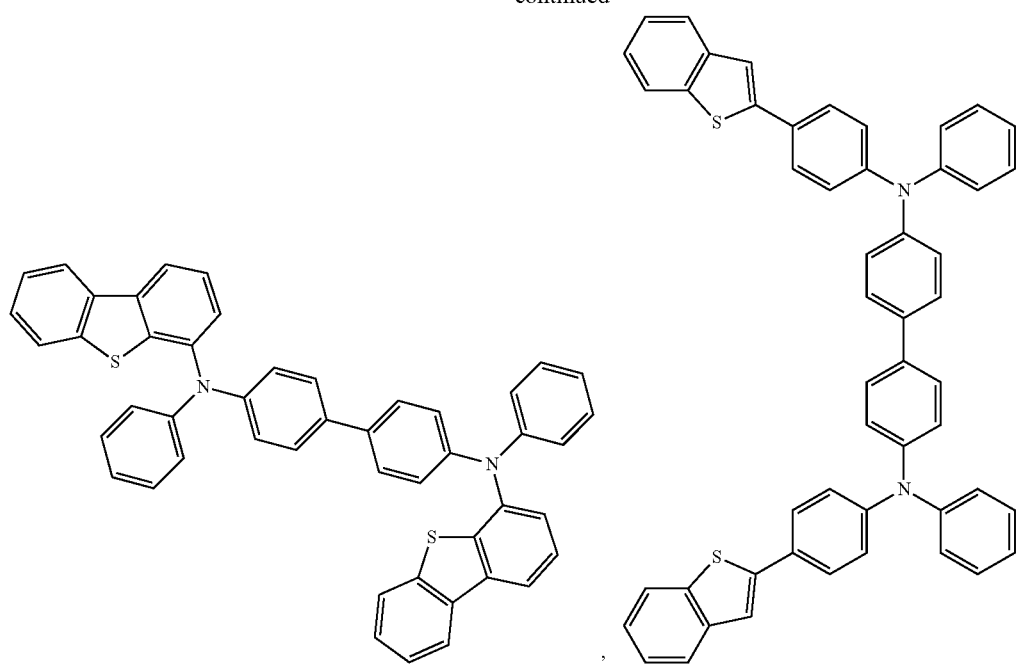
, and
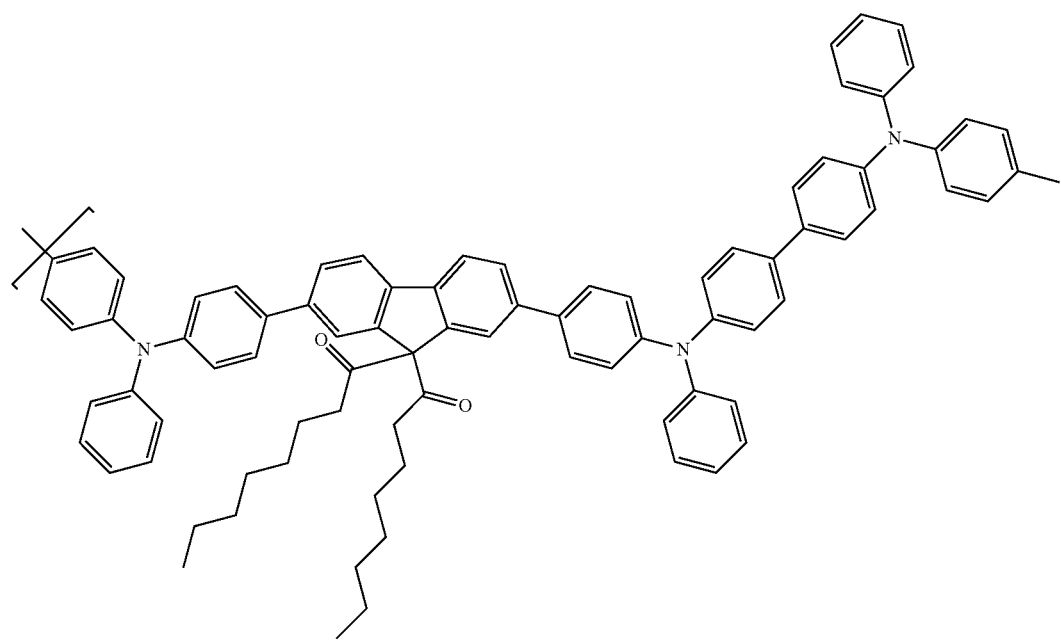

-continued

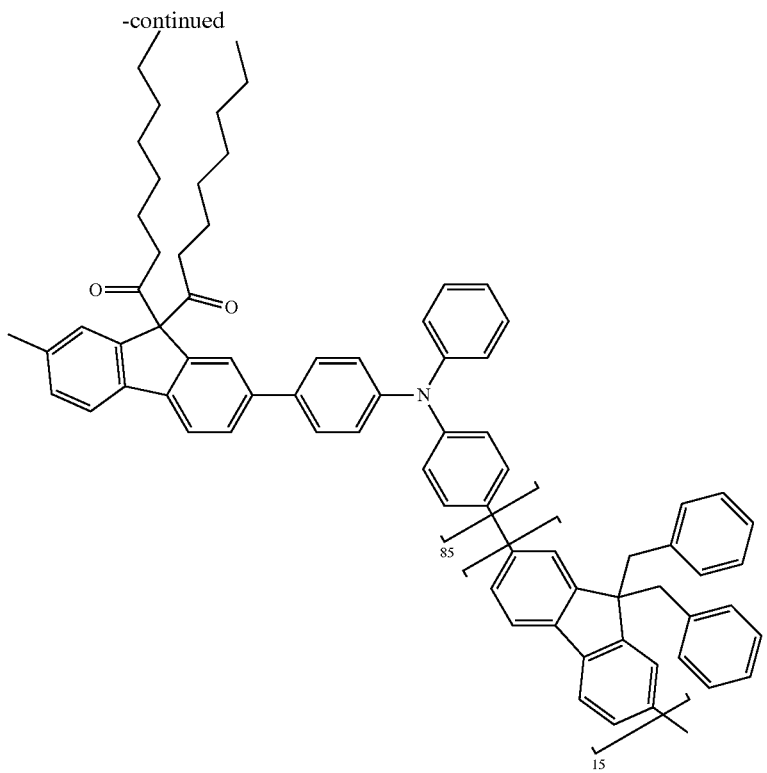

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

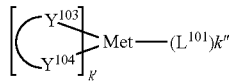

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

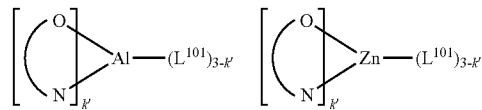

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of other organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

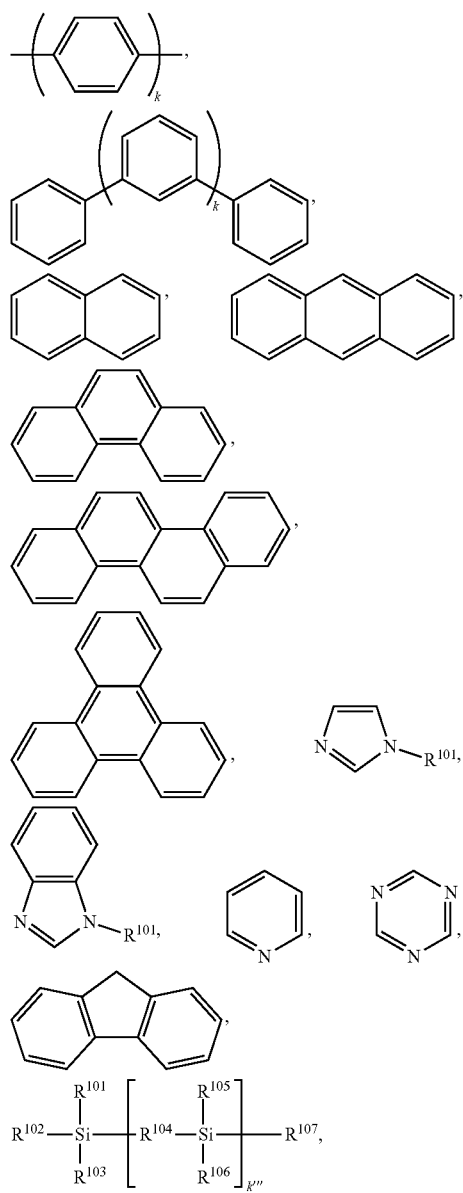

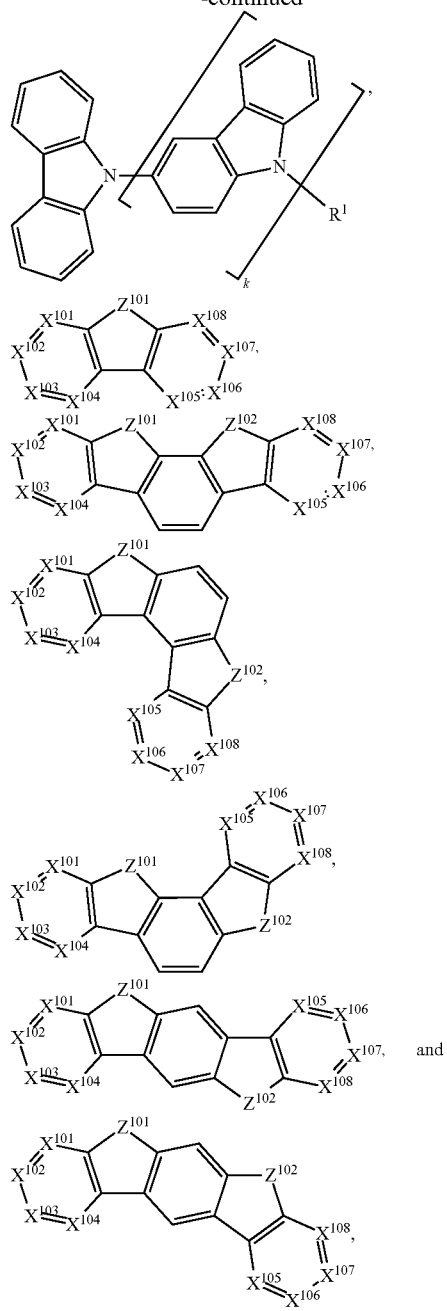

wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k'' is an integer from 0 to 20. $X^{101}$ to $X^{108}$ is selected from C (including CH) or N. $Z^{101}$ and $Z^{102}$ is selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472,
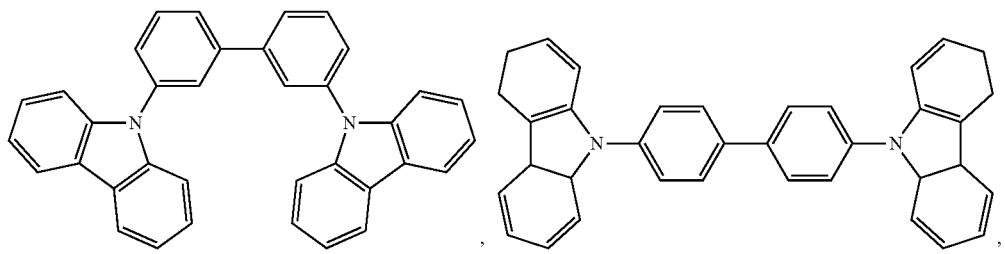
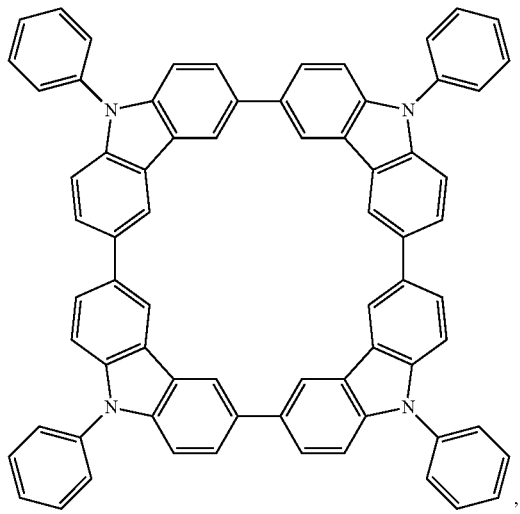
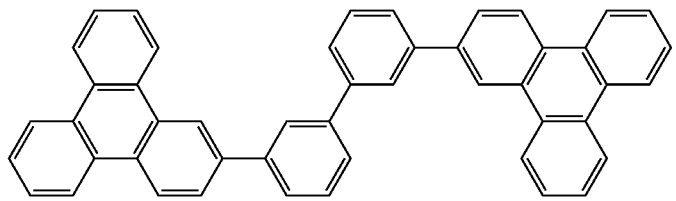
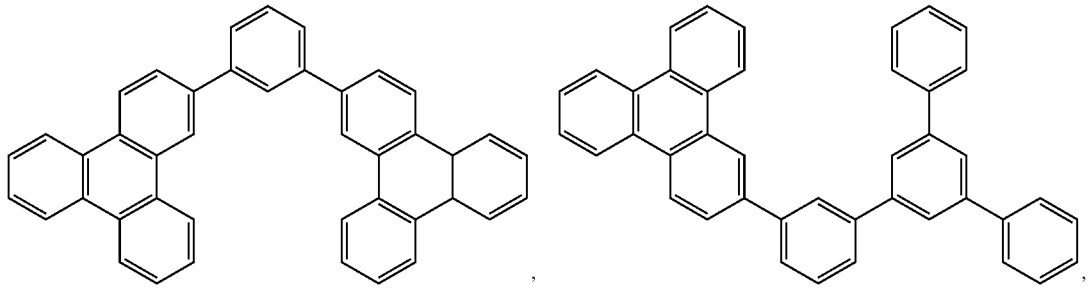

-continued
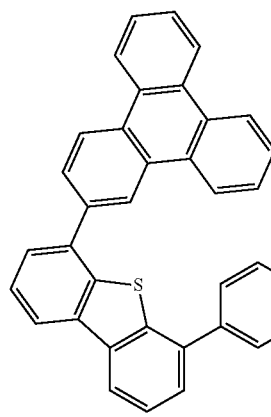 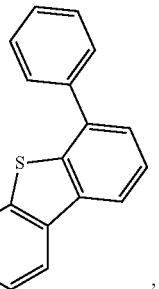 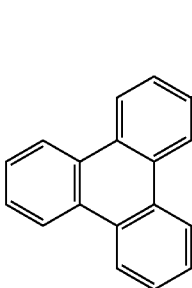
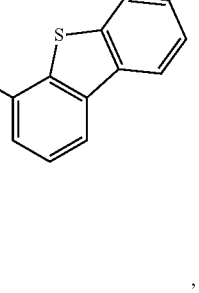
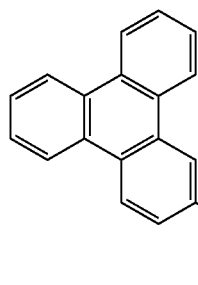 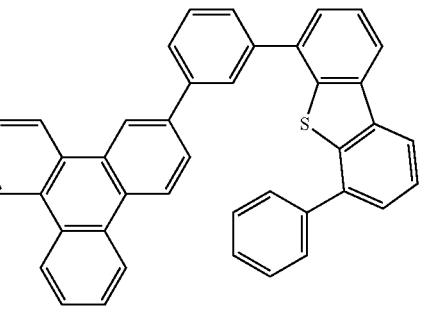
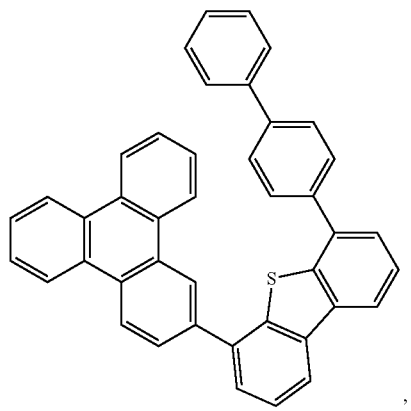 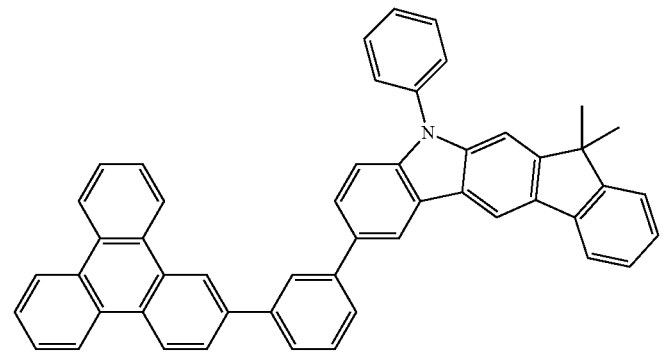
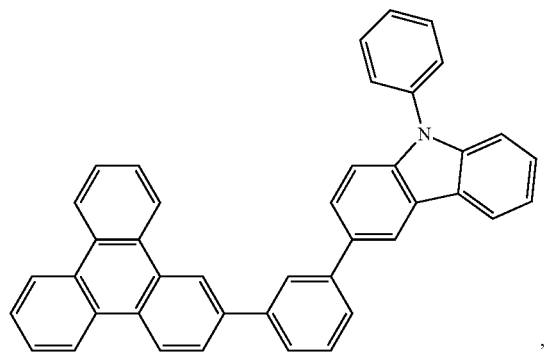 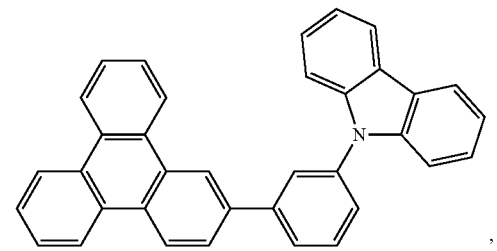

-continued
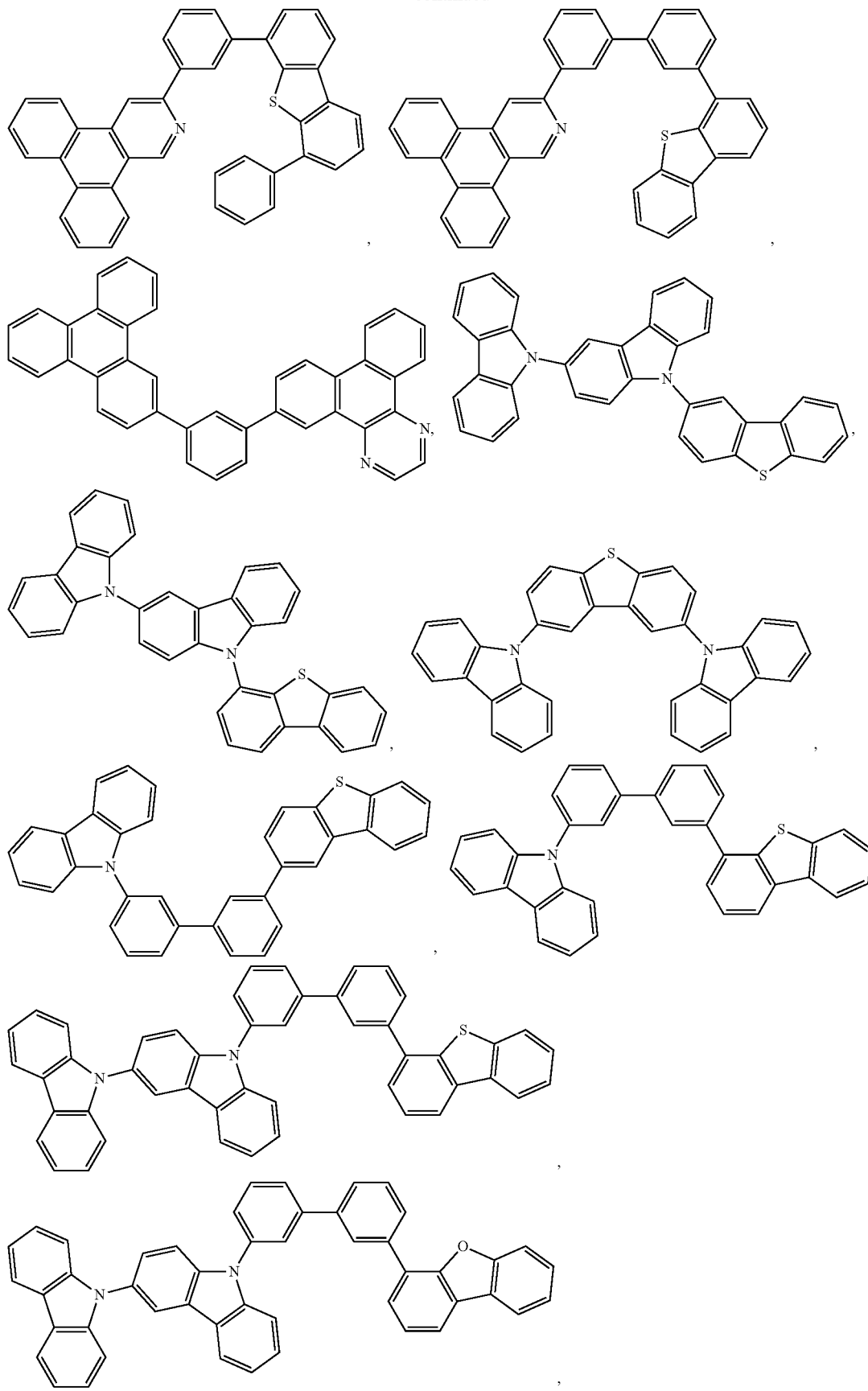

-continued
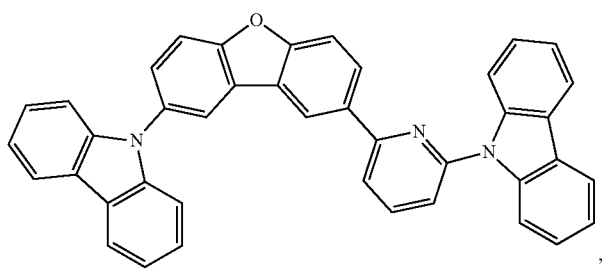
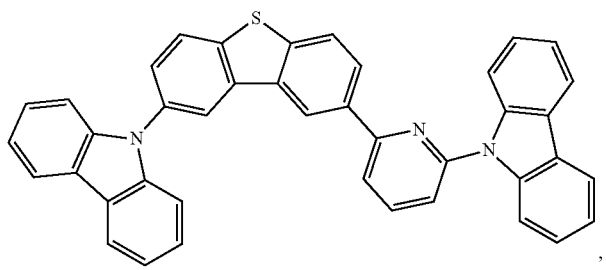
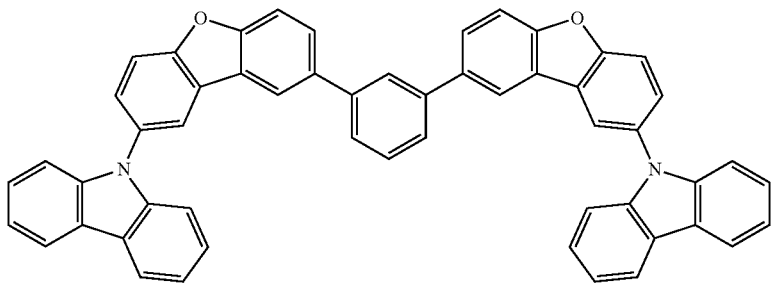
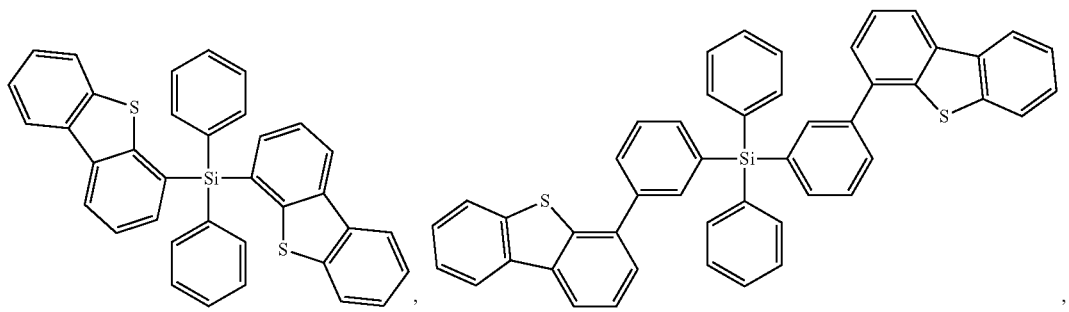
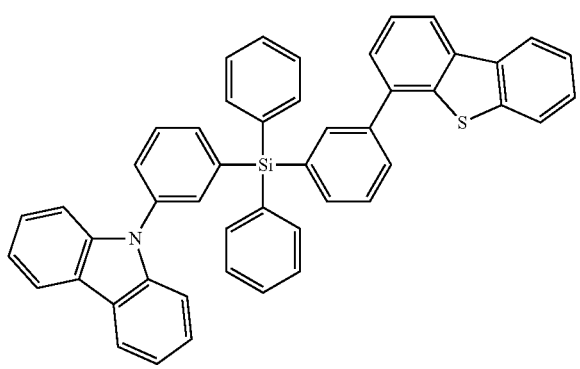

-continued
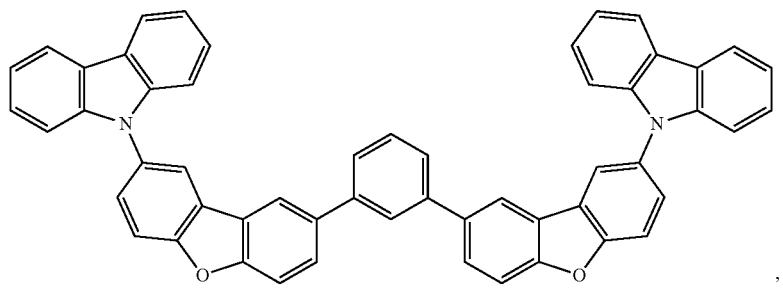
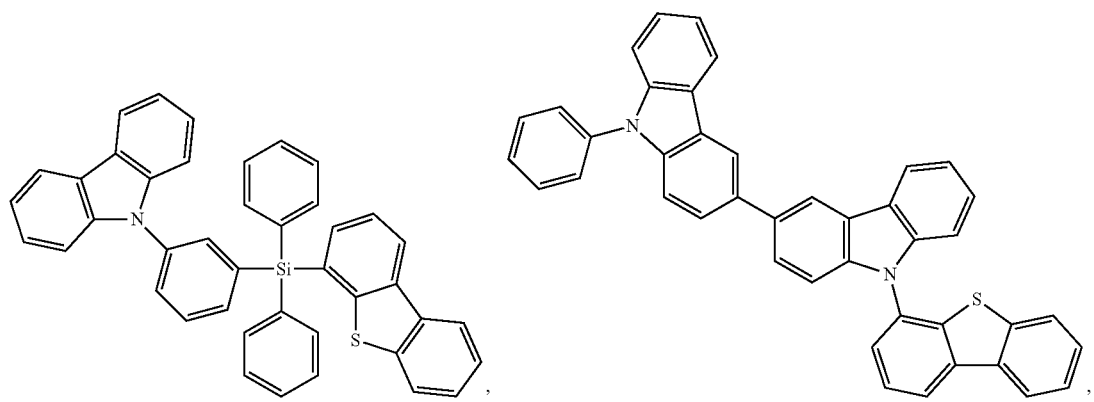
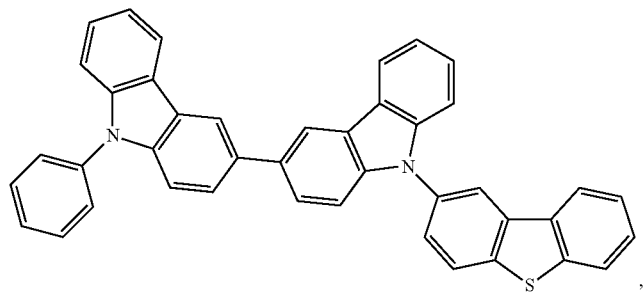
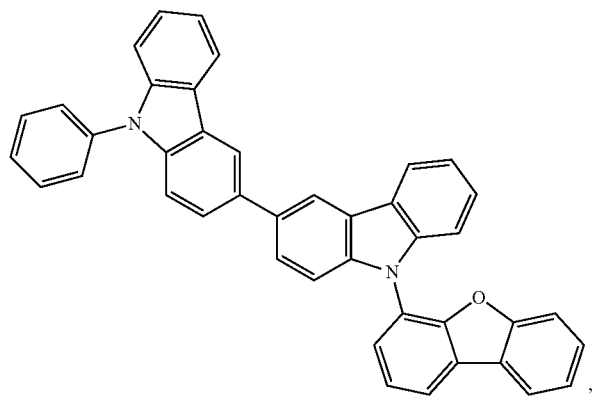

-continued
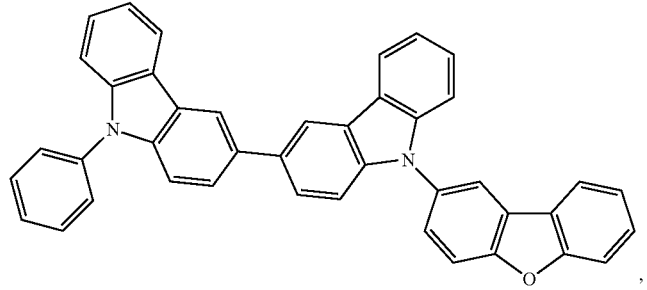
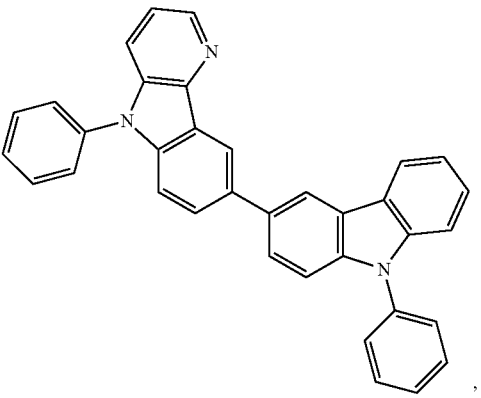
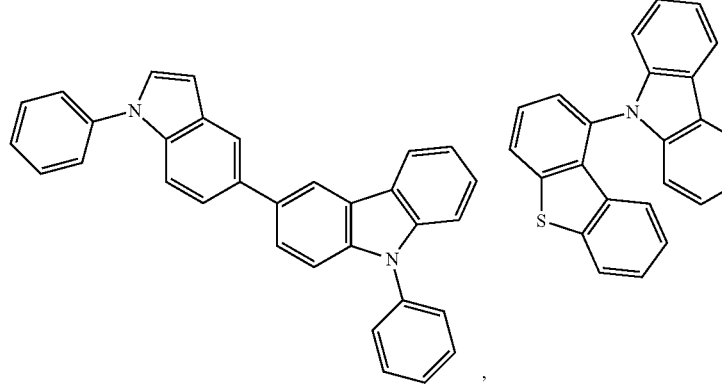
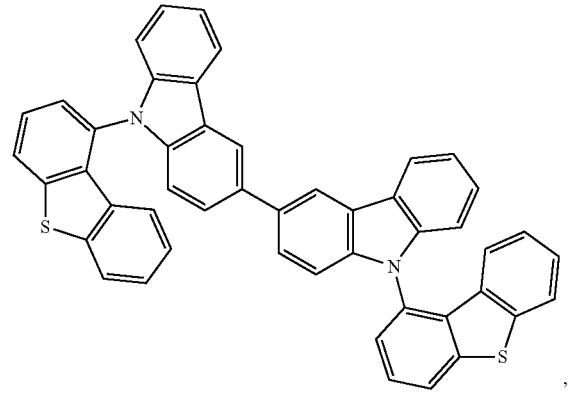
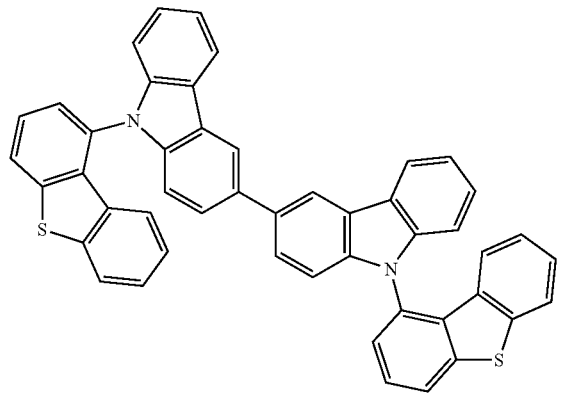
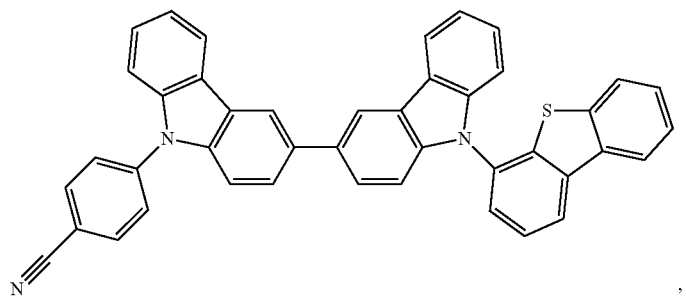

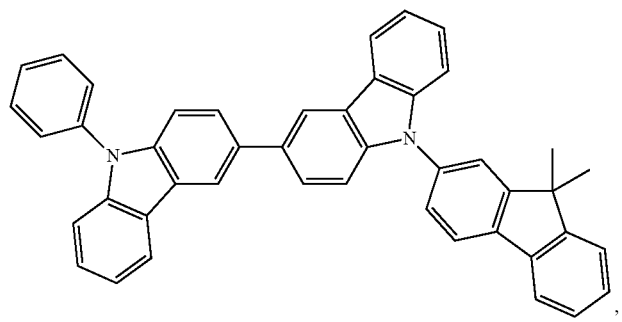
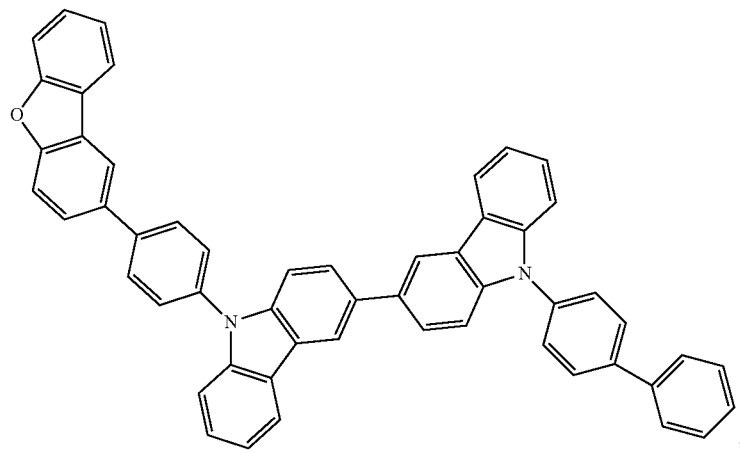
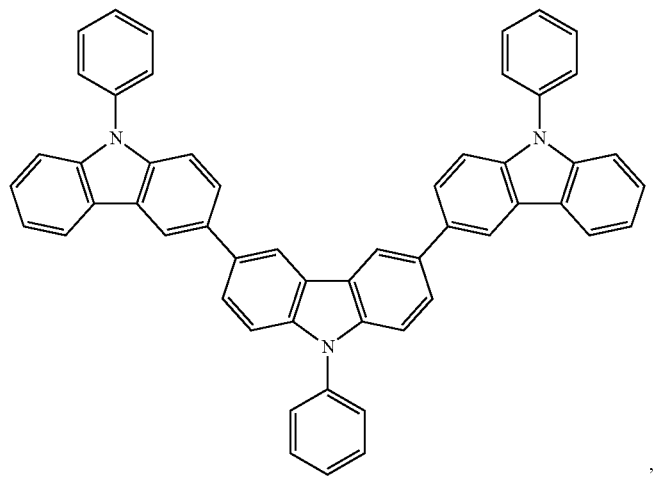
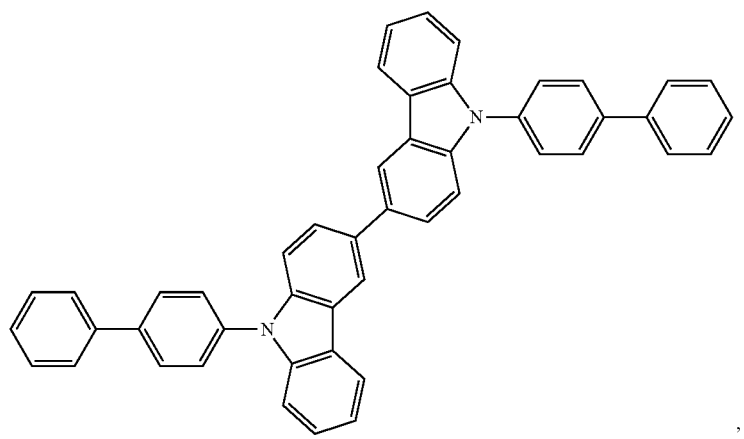

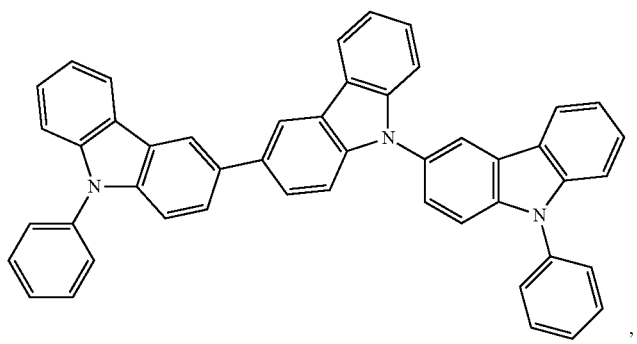
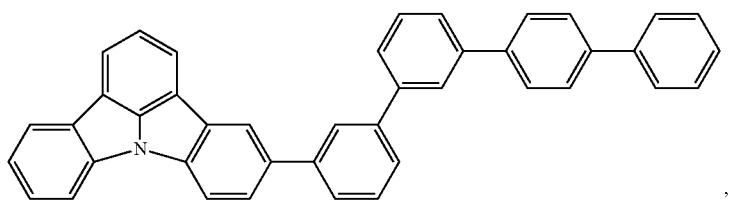
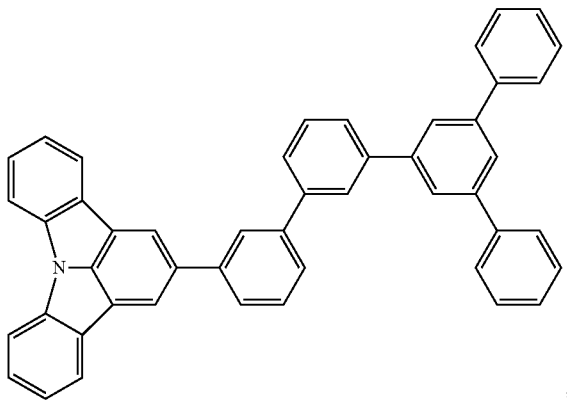
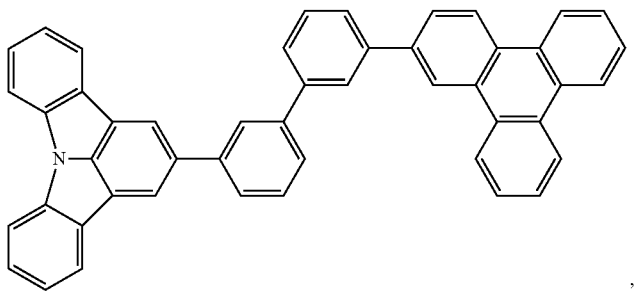
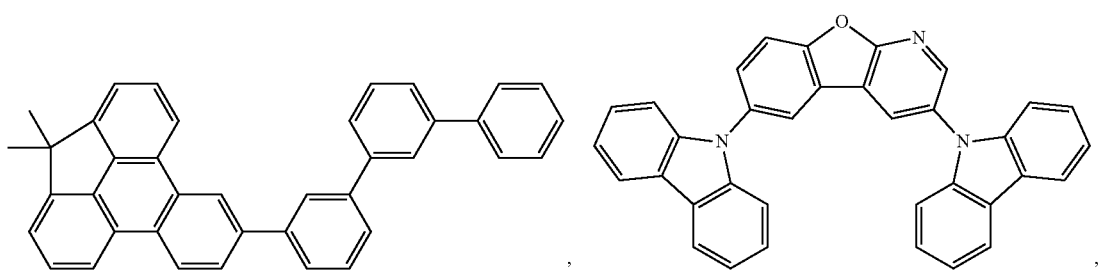

-continued
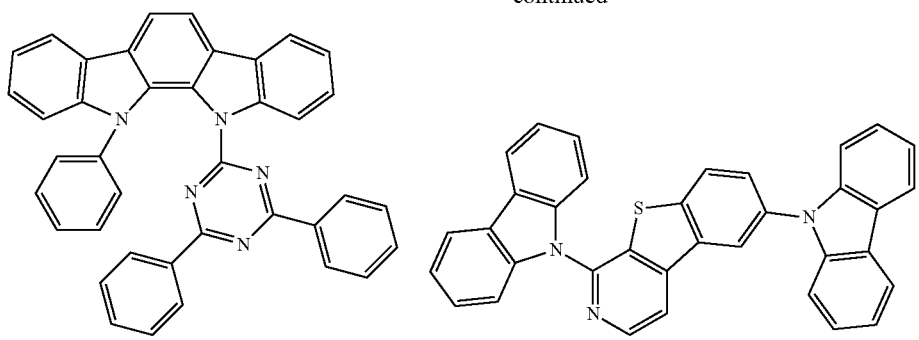
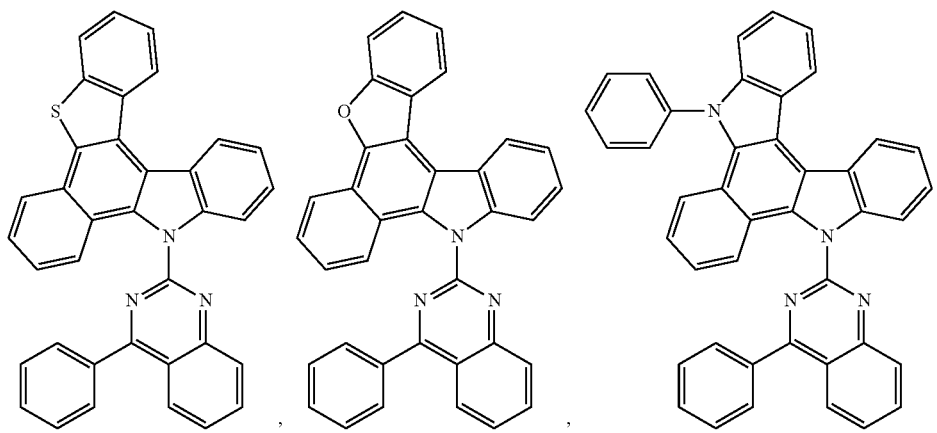
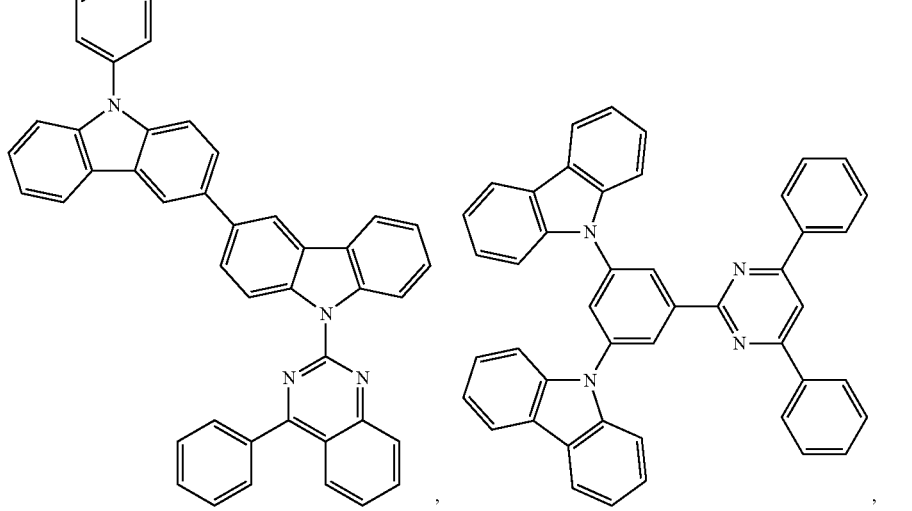
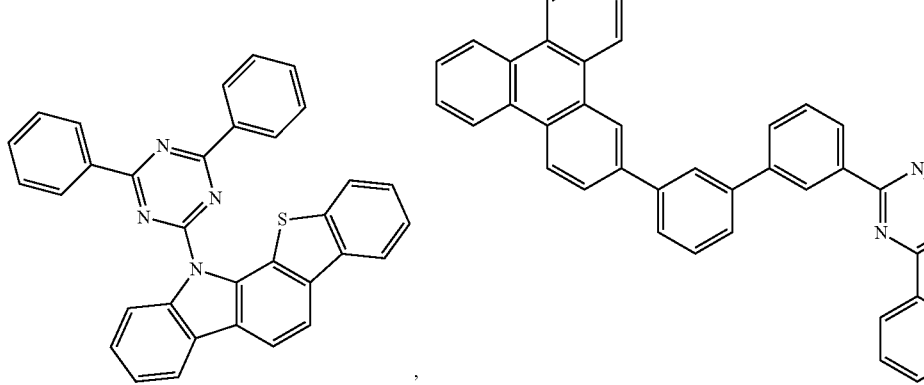

-continued
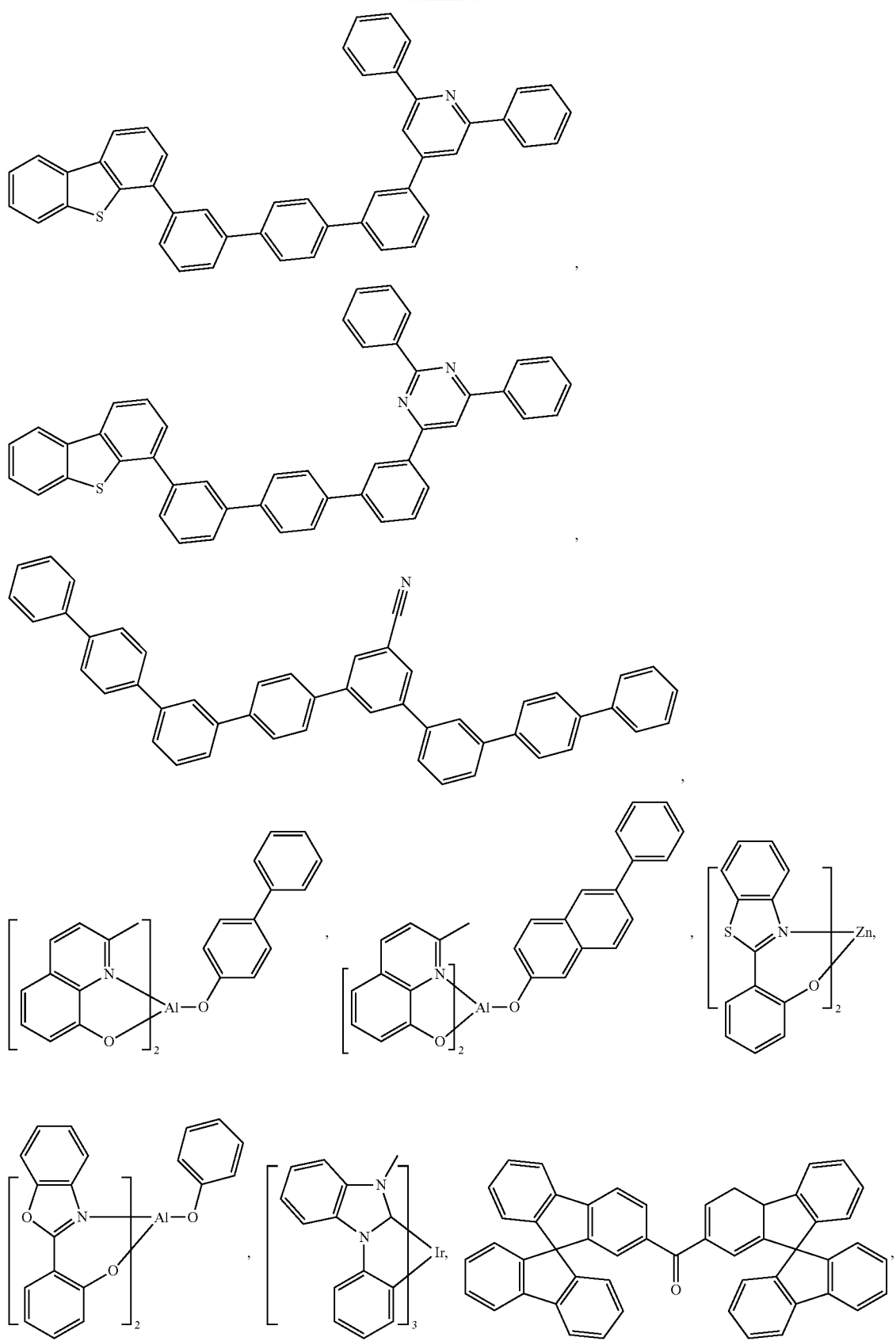

-continued

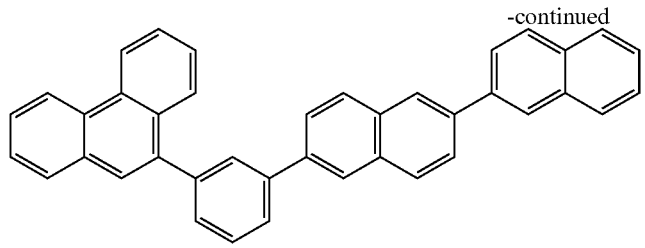

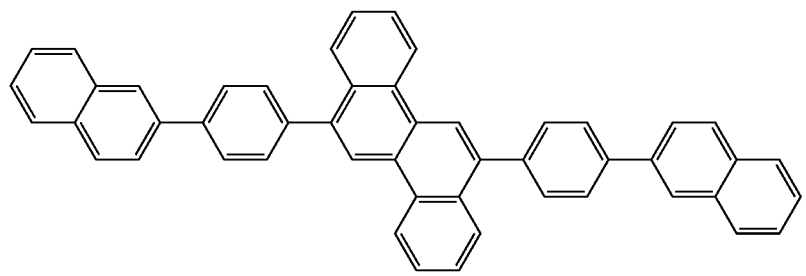
, and

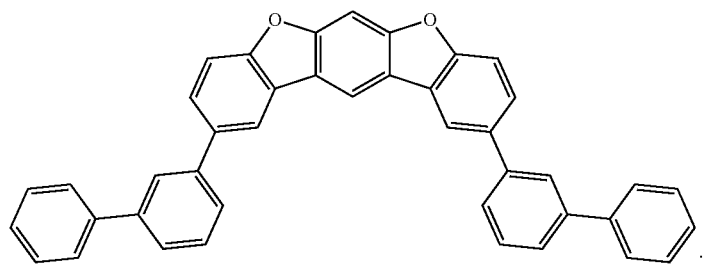
.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

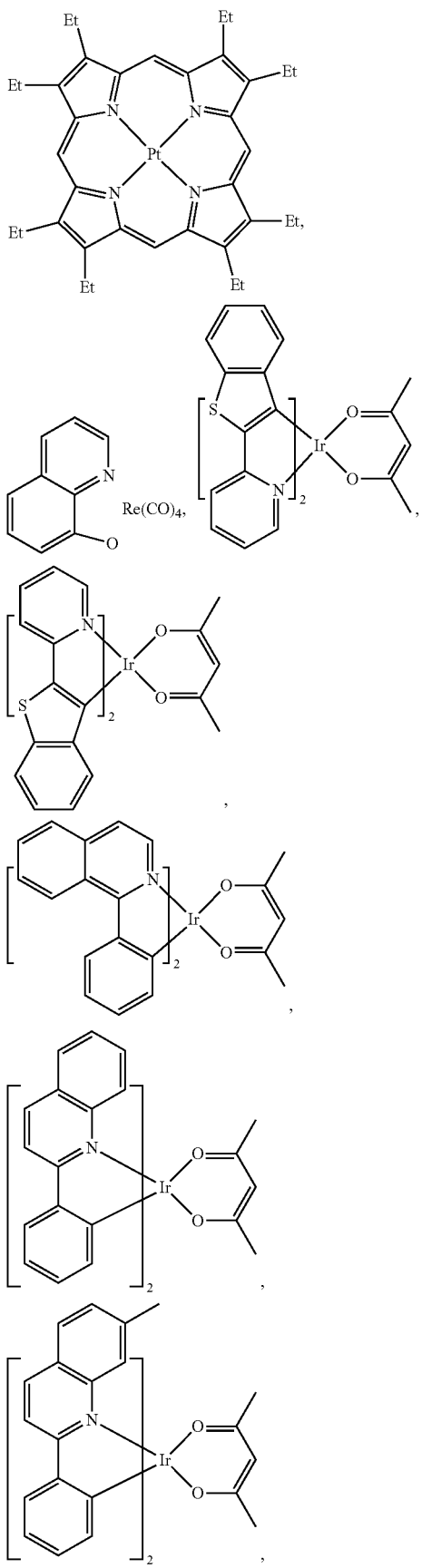
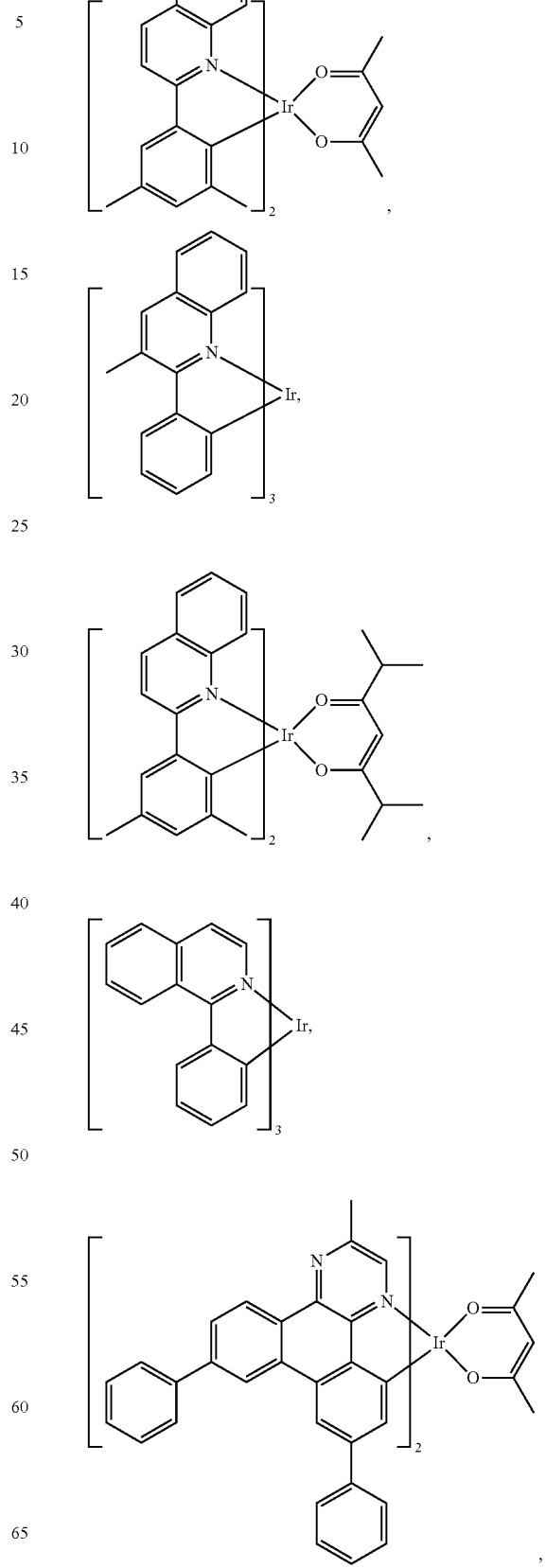

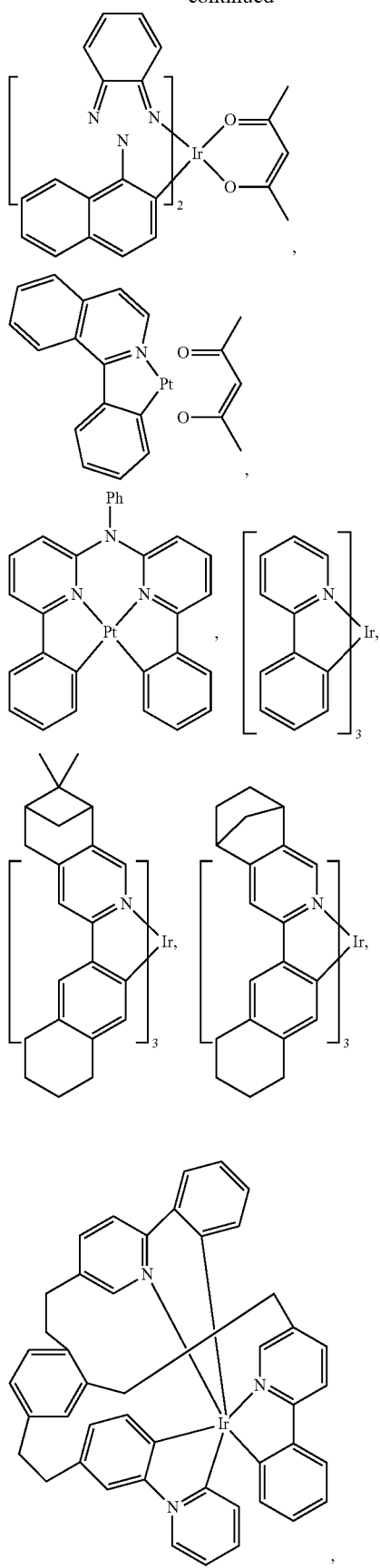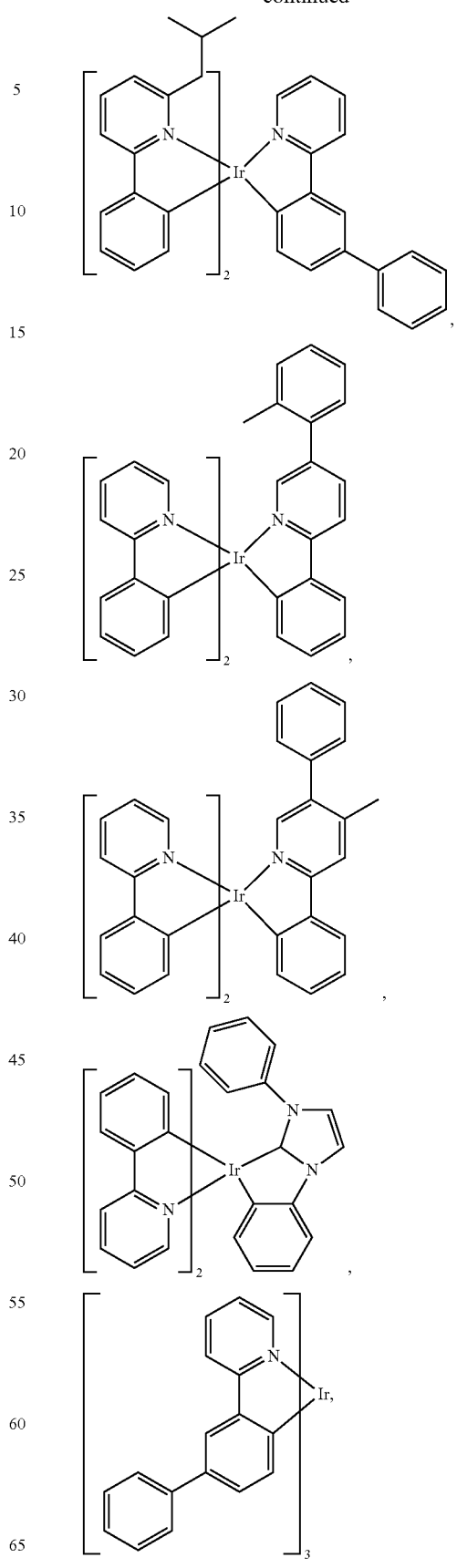

-continued
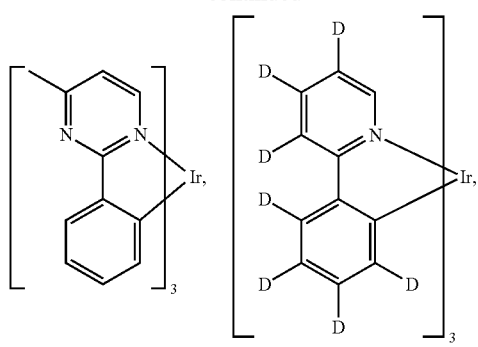
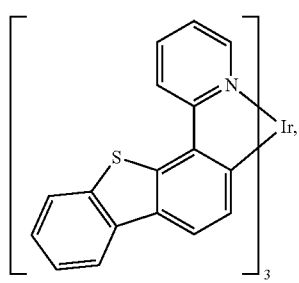
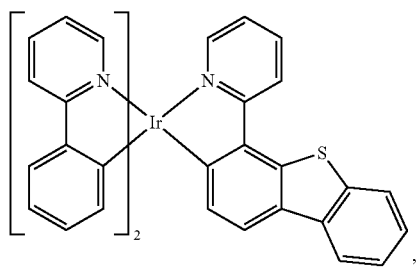
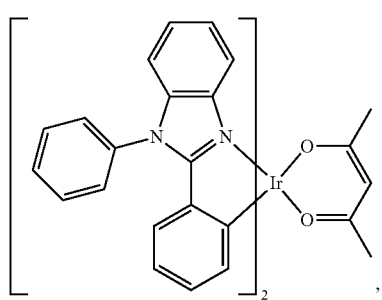
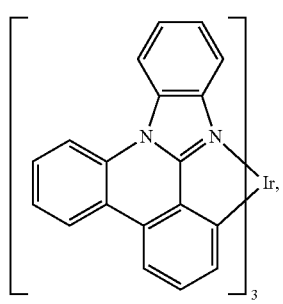
-continued
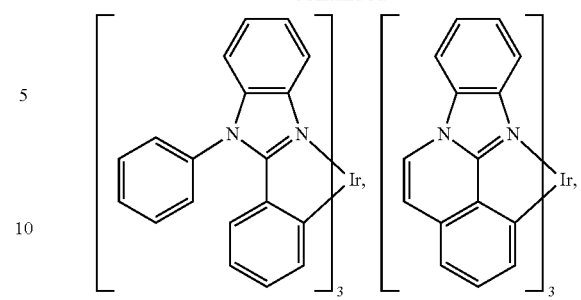
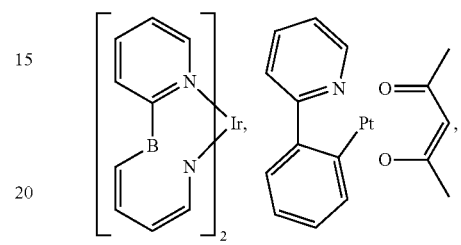
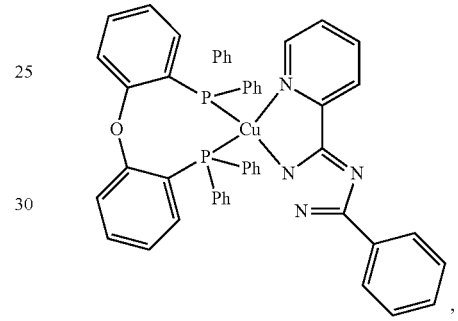
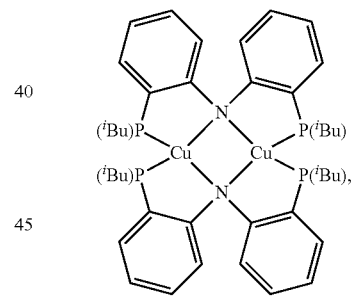
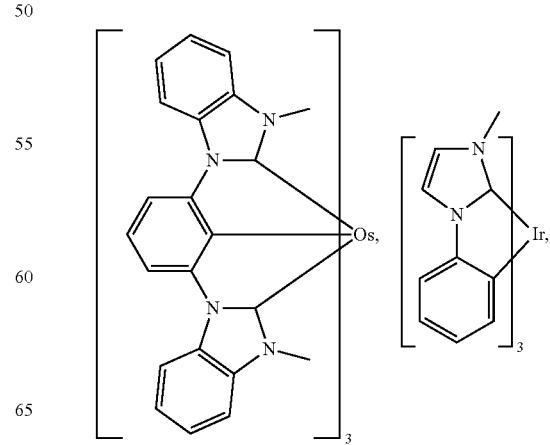

121
-continued
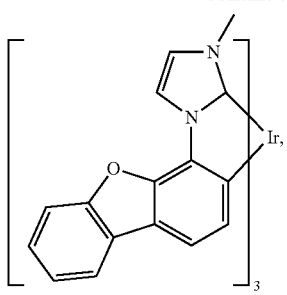
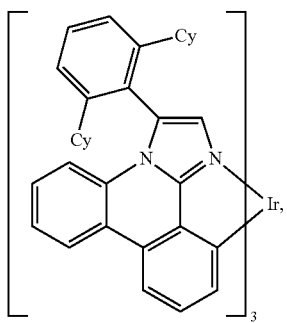
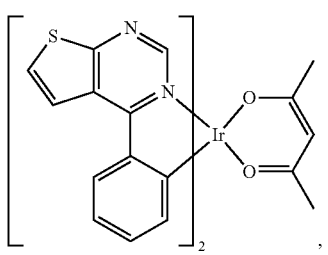
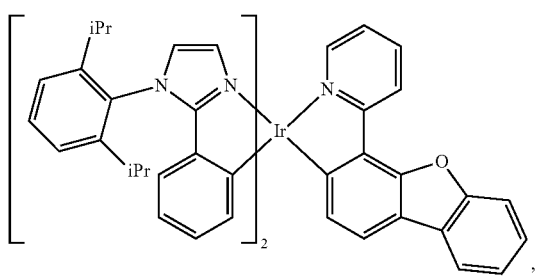
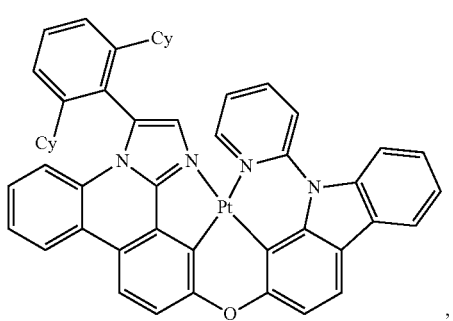
122
-continued
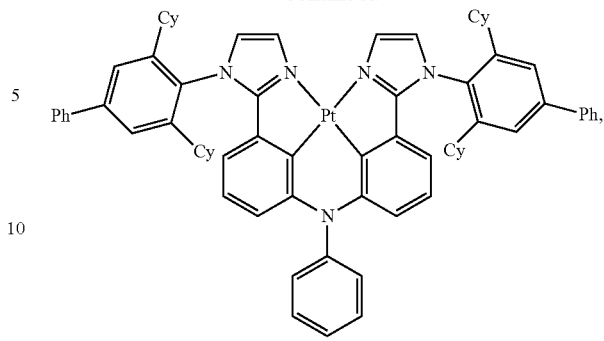
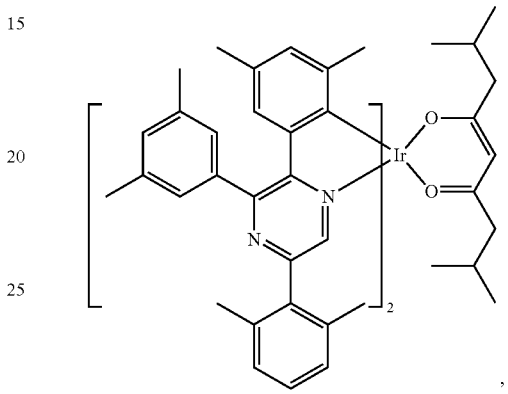
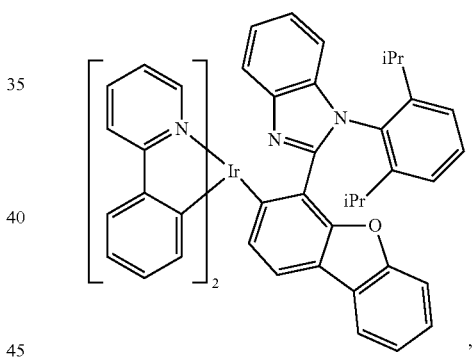
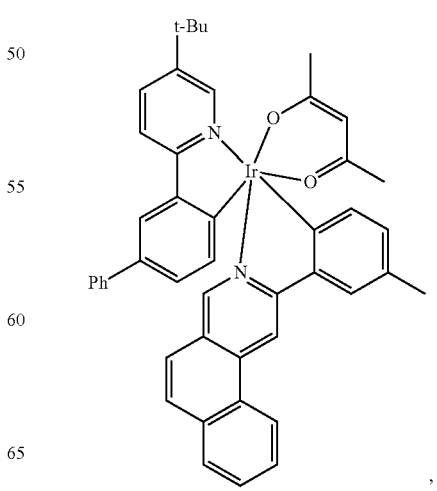

123
-continued
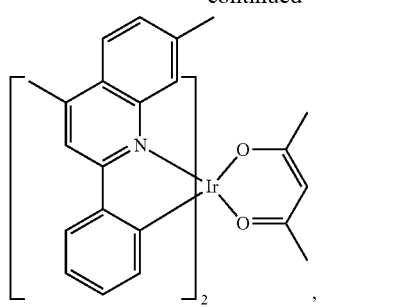,
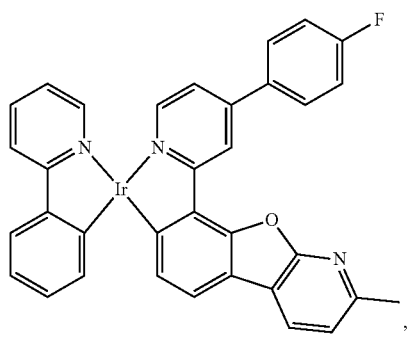,
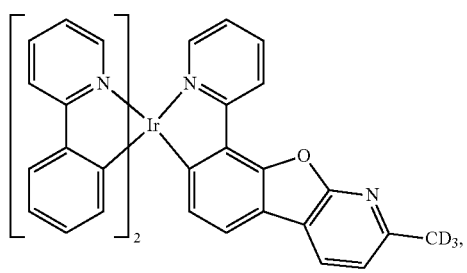,
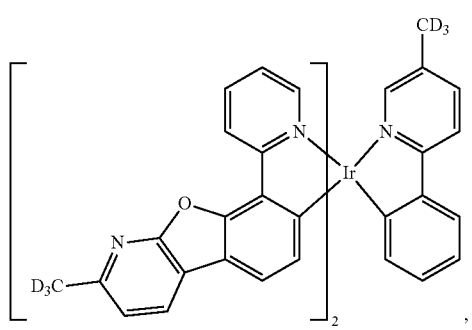,
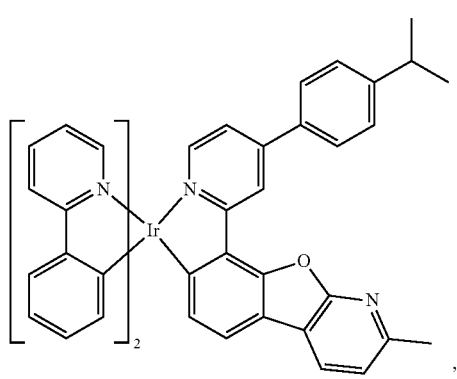,
124
-continued
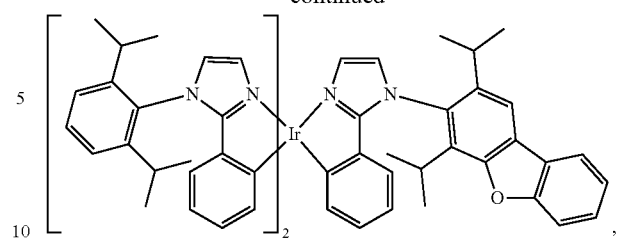,
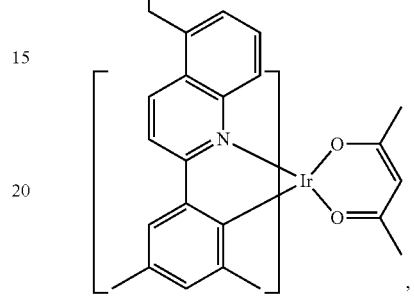,
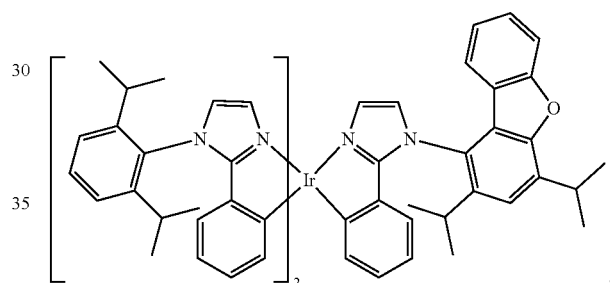,
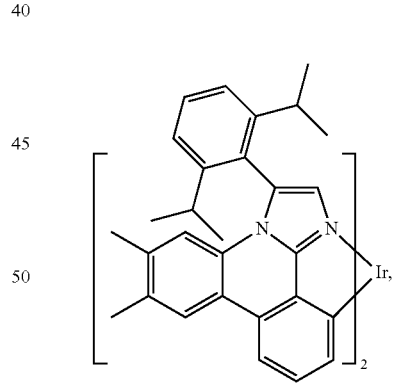,
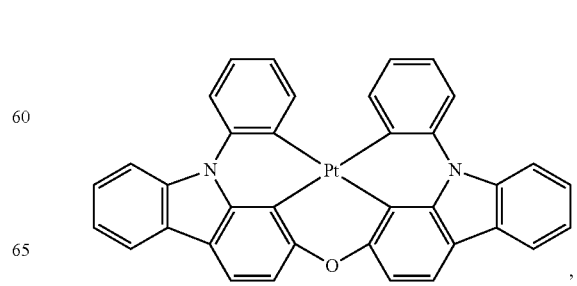, 125
-continued
126
-continued
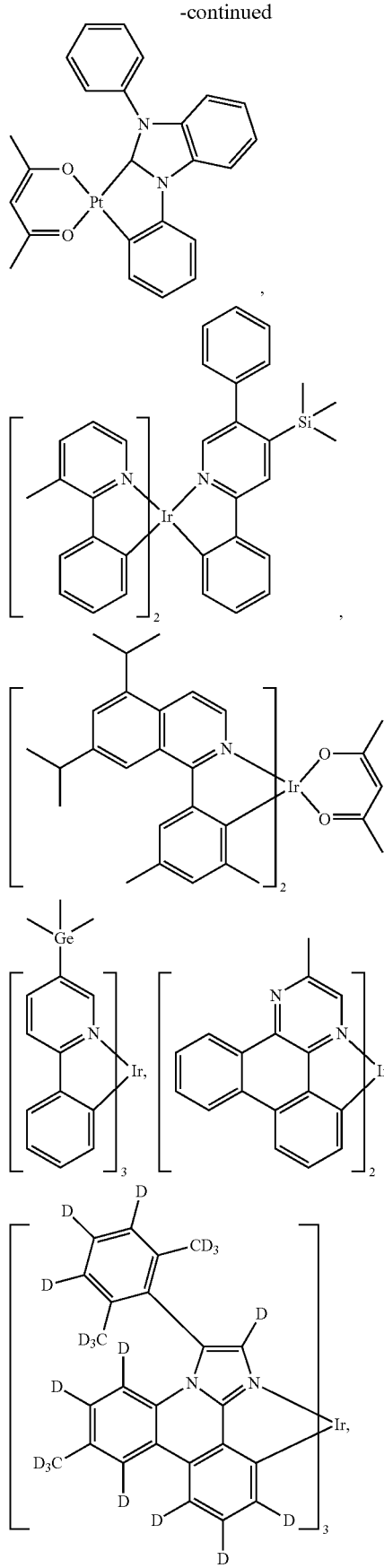
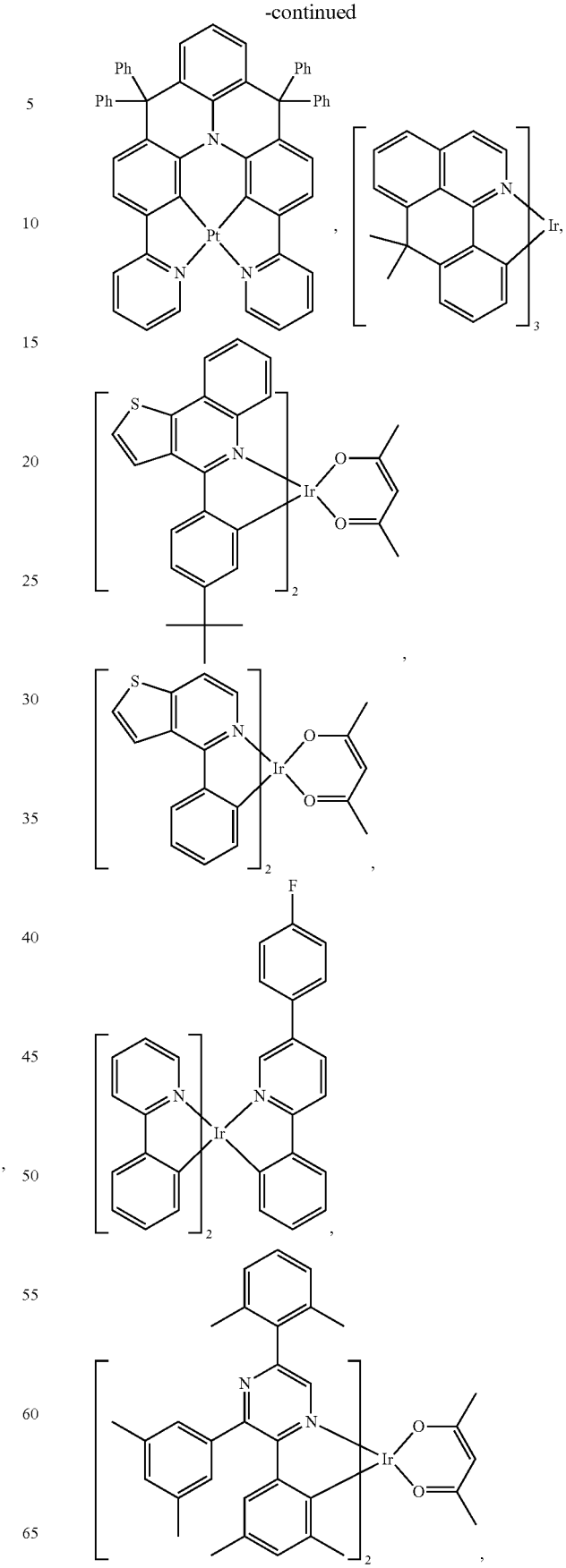

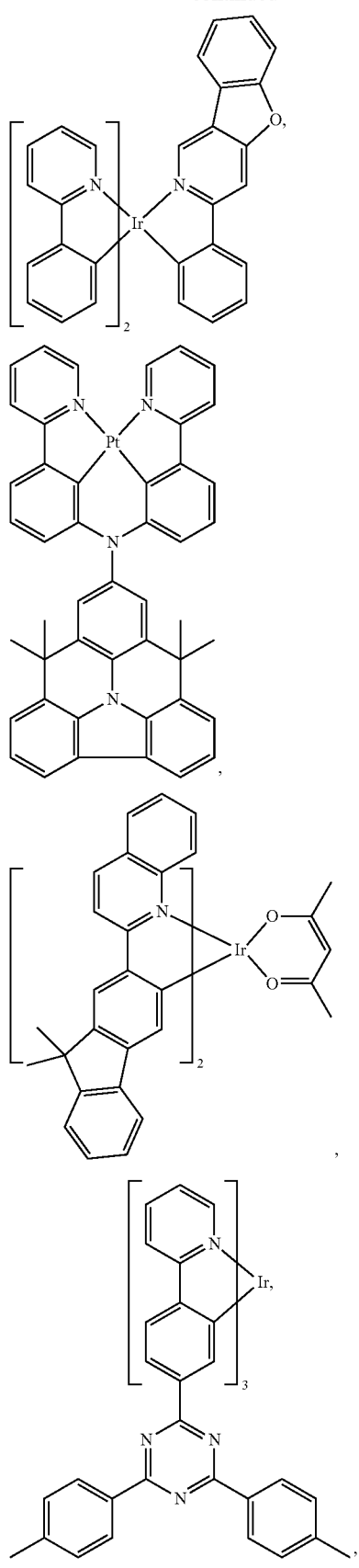

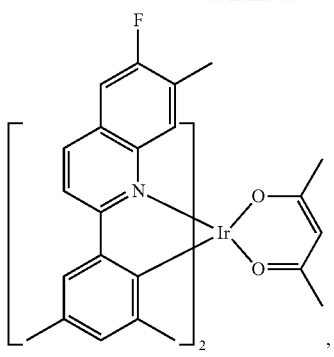
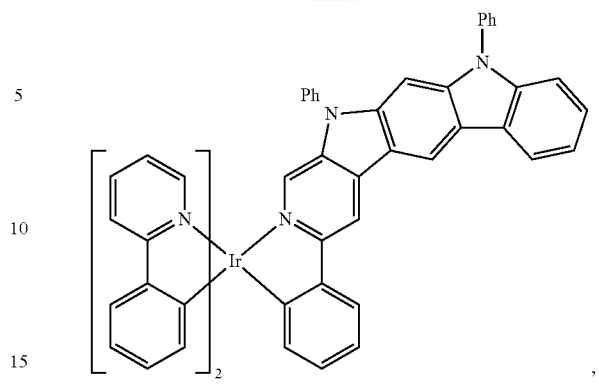
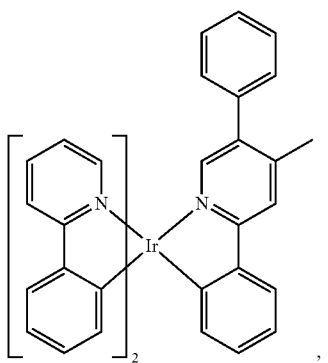
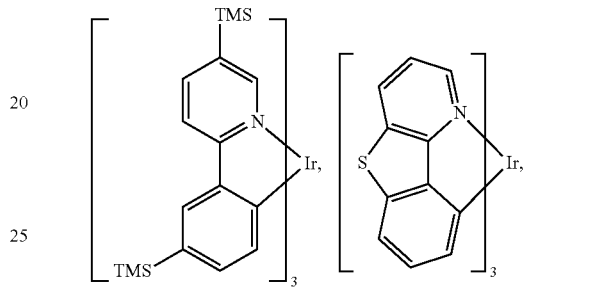
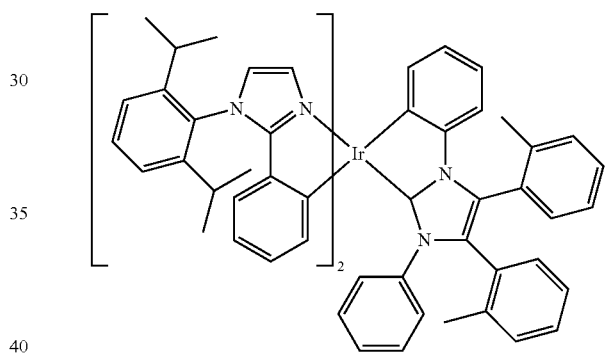
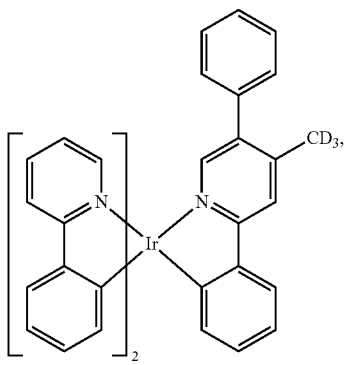
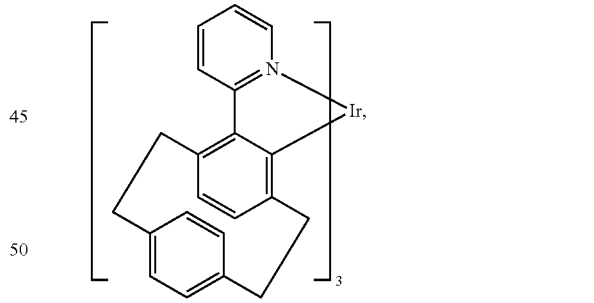
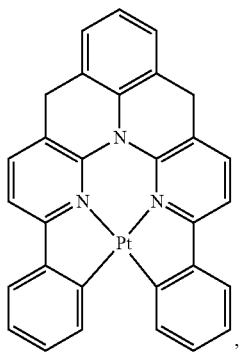
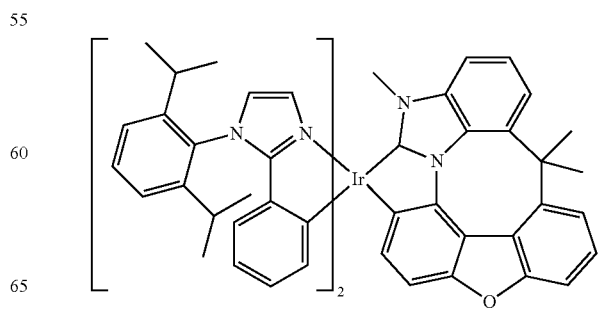

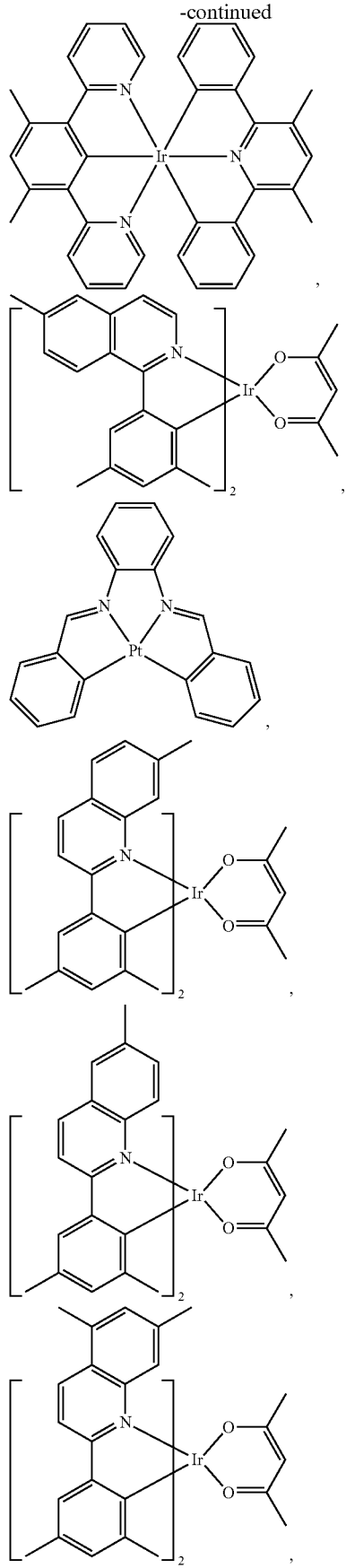
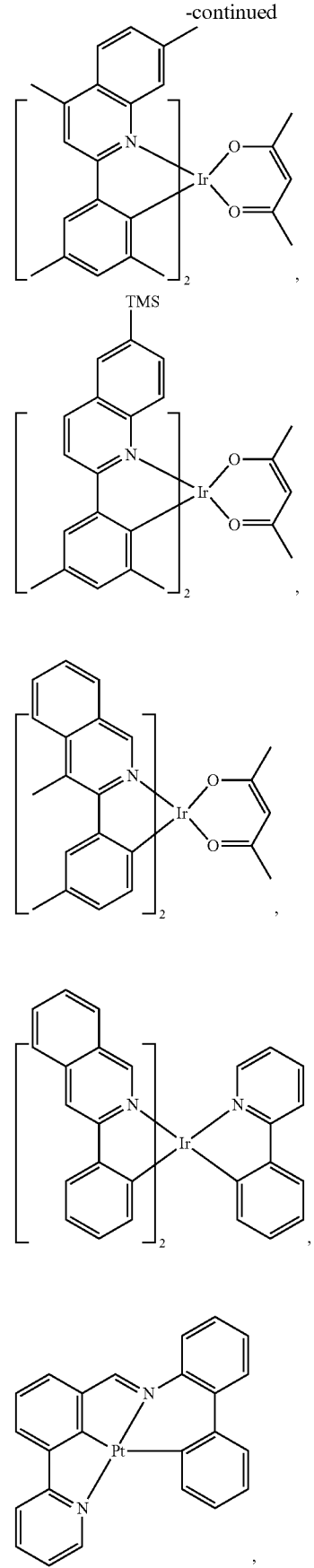

133
-continued
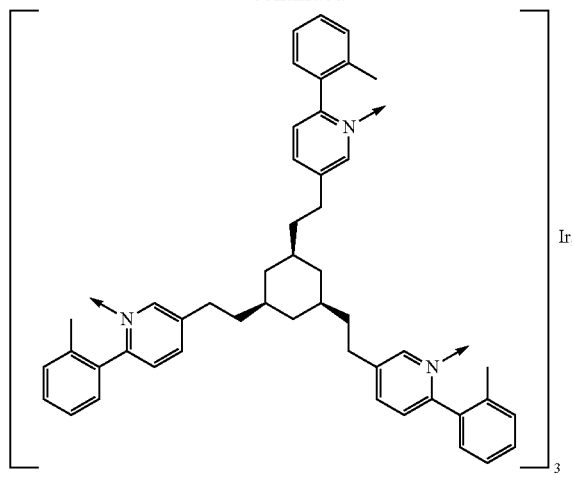
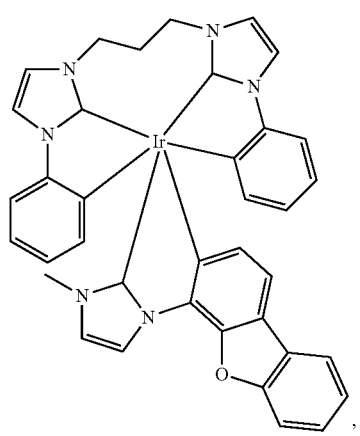
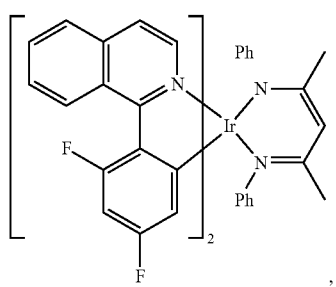
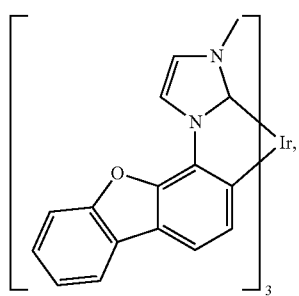
134
-continued
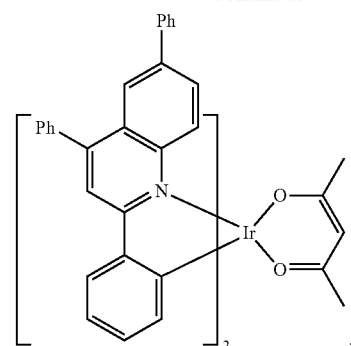
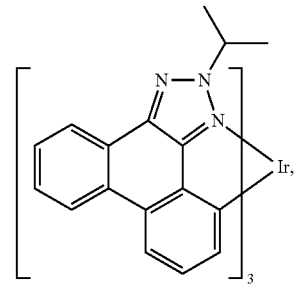
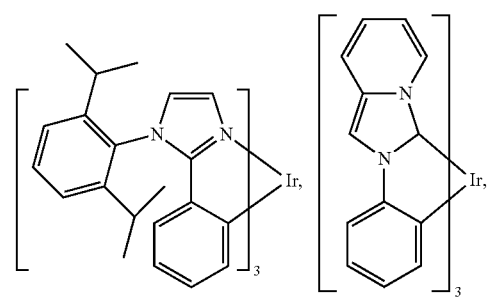
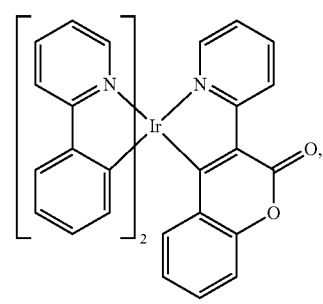
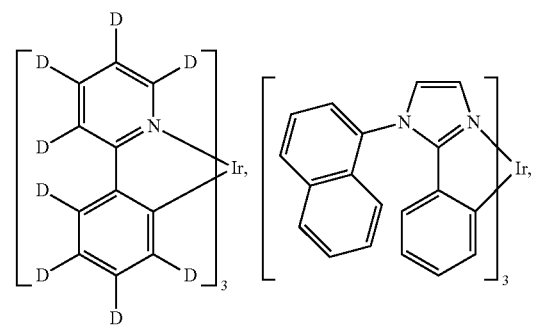

-continued

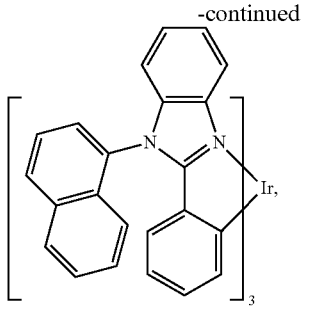

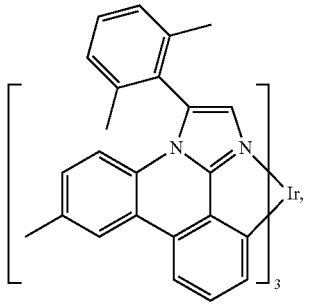

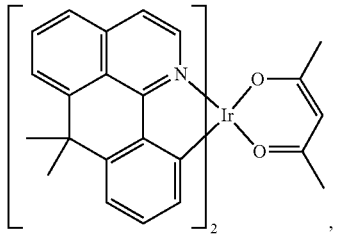

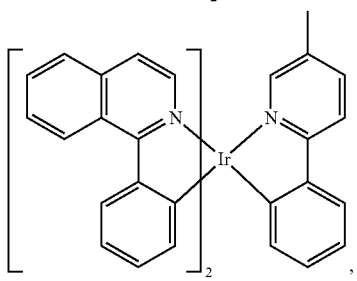

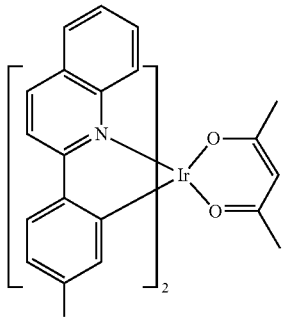

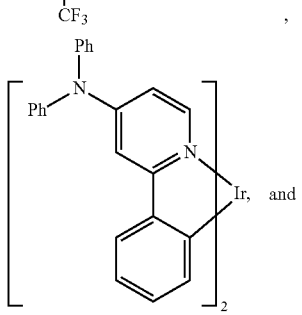

-continued

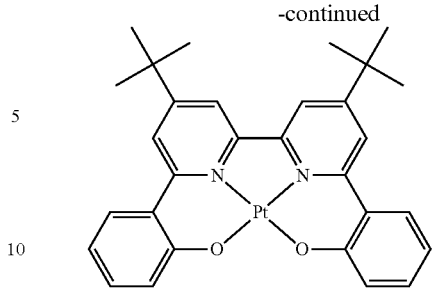

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

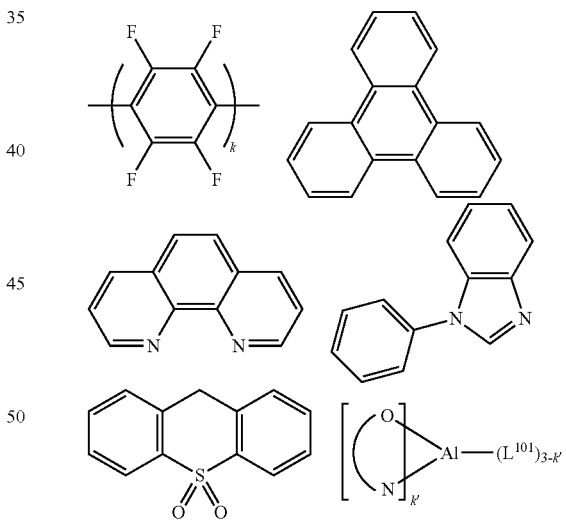

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the En material are not particularly limited, and any metal complexes or organic compounds may be used as long as they are typically used to transport electrons.

In one aspect, compound used in ETL contains at least one of the following groups in the molecule:

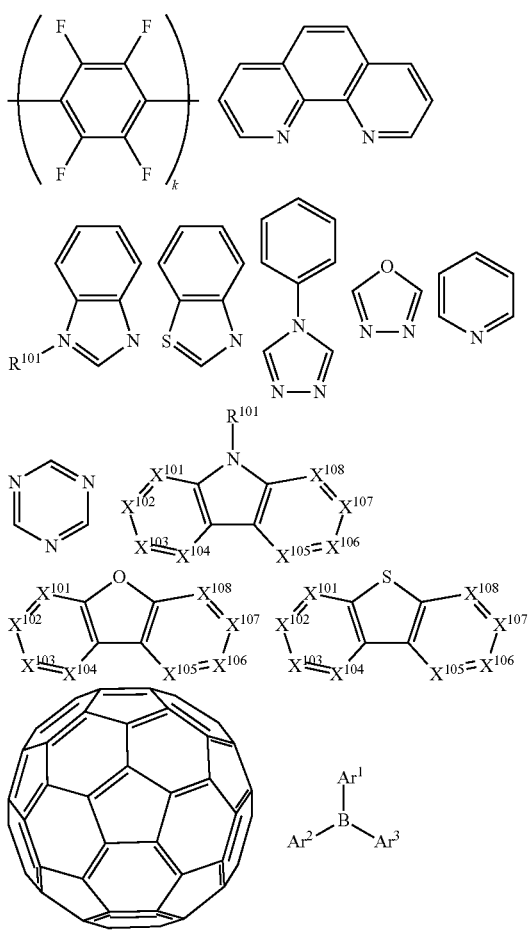

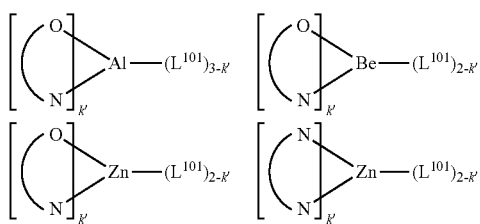

wherein R[101] is selected from the group consisting of hydrogen, deuterium, halide, alkyl, cycloalkyl, heteroalkyl, arylalkyl, alkoxy, myloxy, amino, silyl, alkenyl, cycloalkenyl, heteroalkenyl, alkynyl, aryl, heteromyl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $A^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

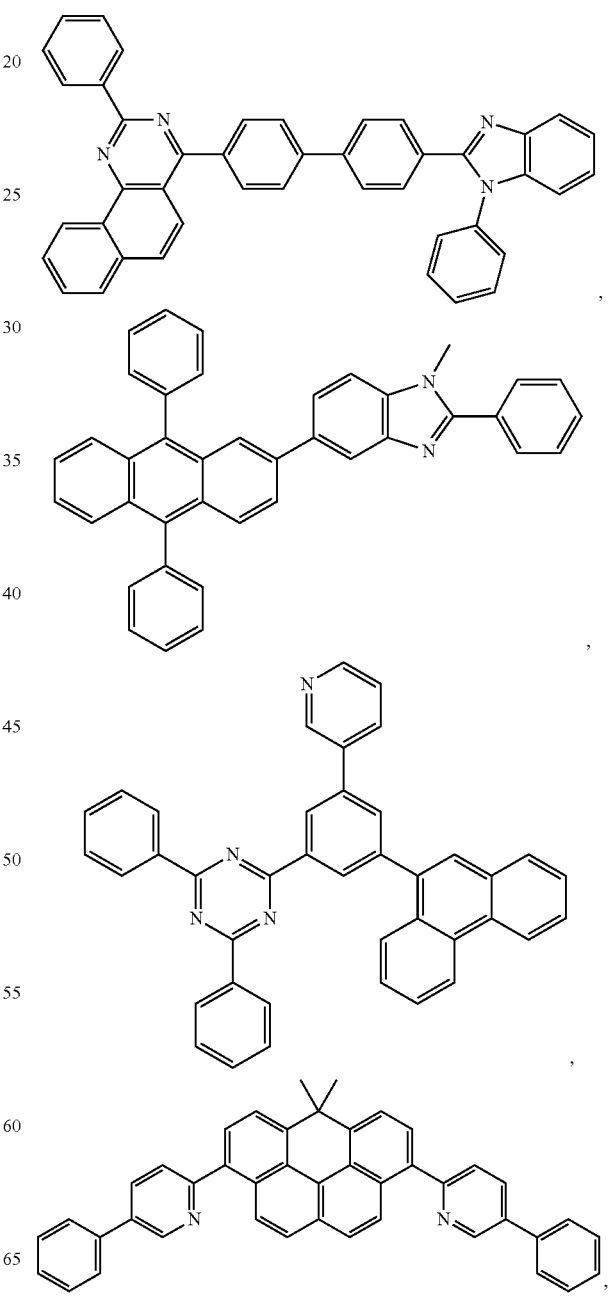

139
-continued
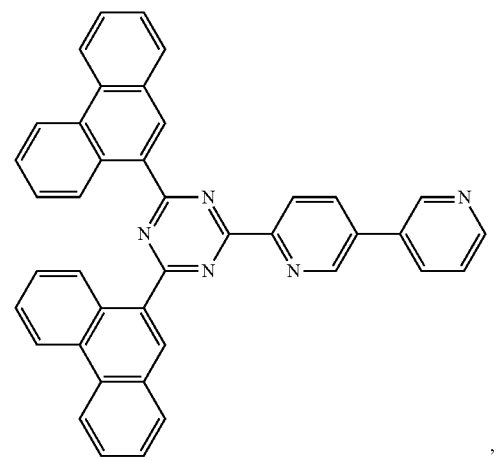
,
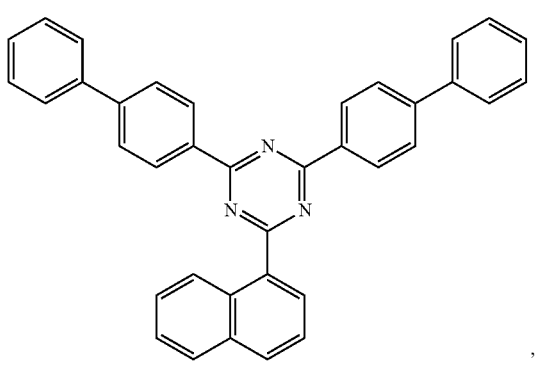
,
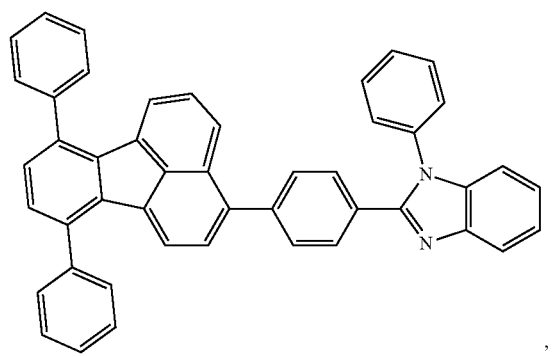
,
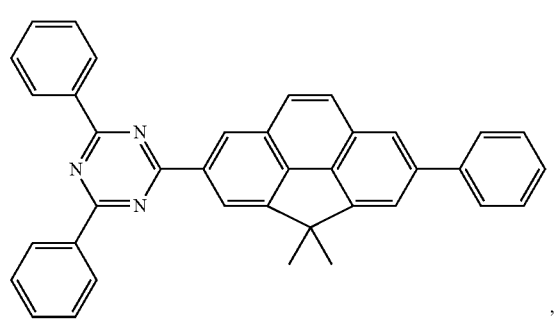
,
140
-continued
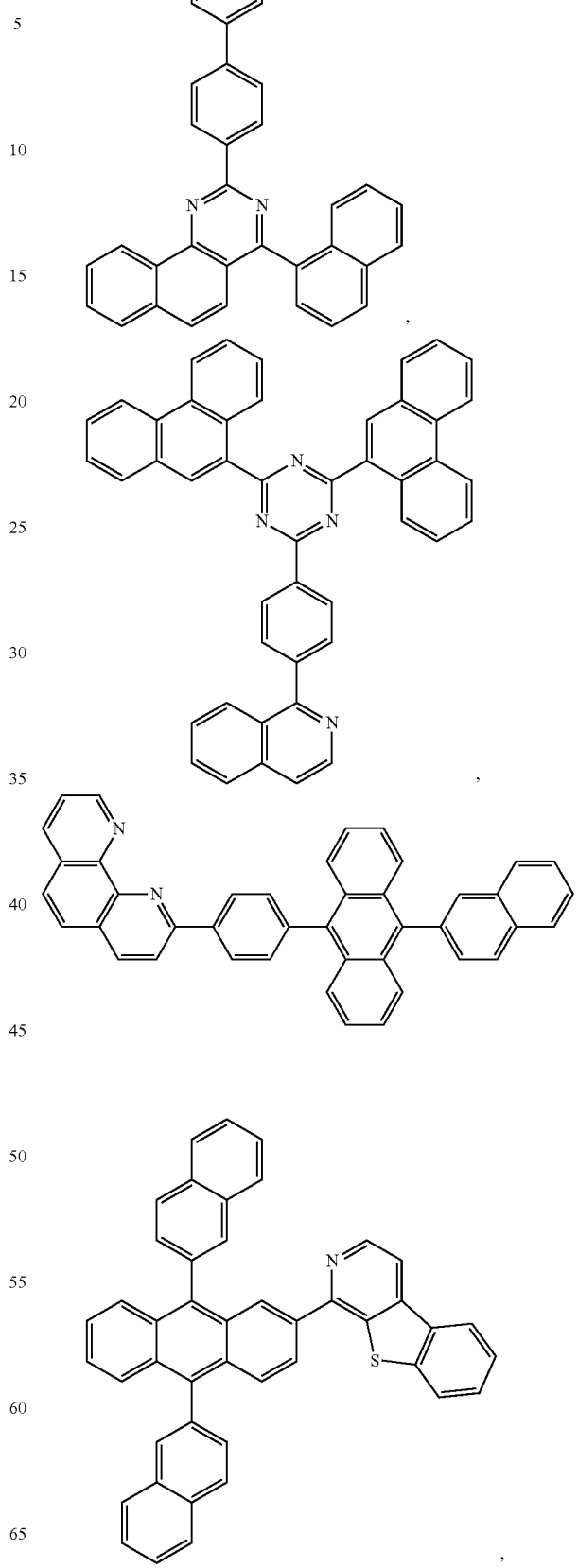

141
-continued
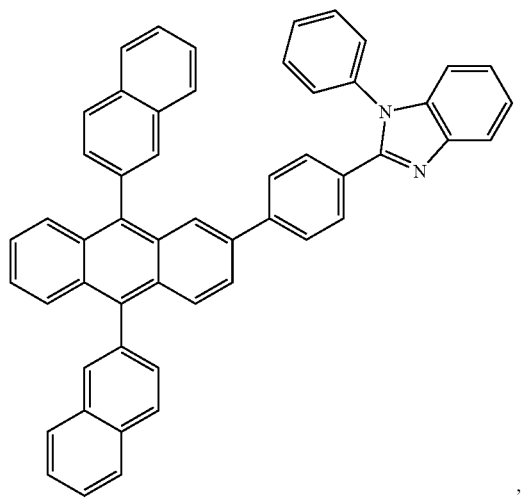
,
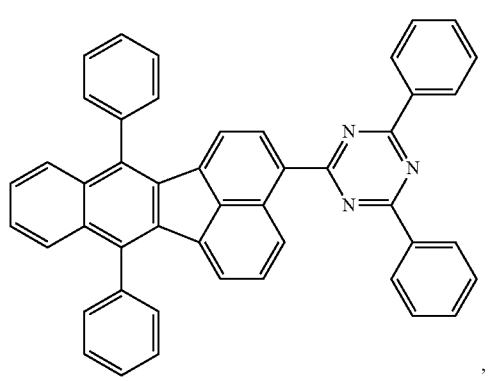
,
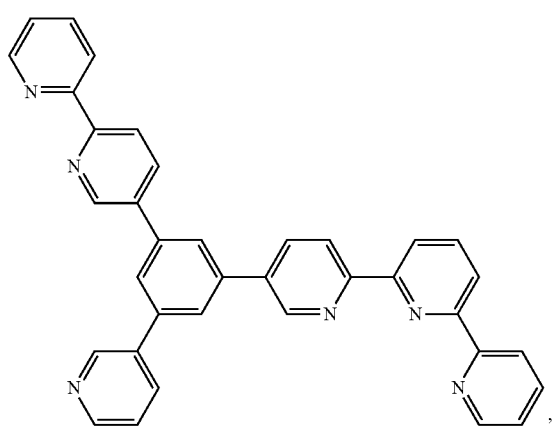
,
142
-continued
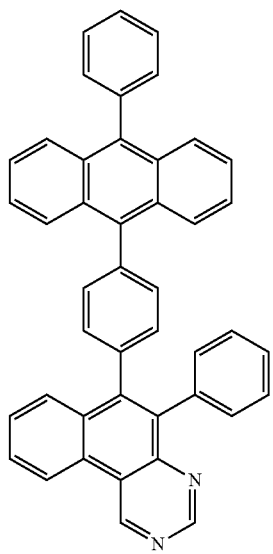
,
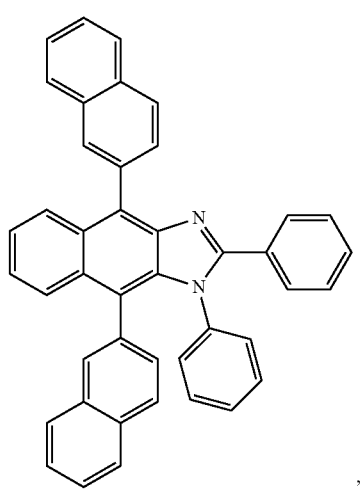
,
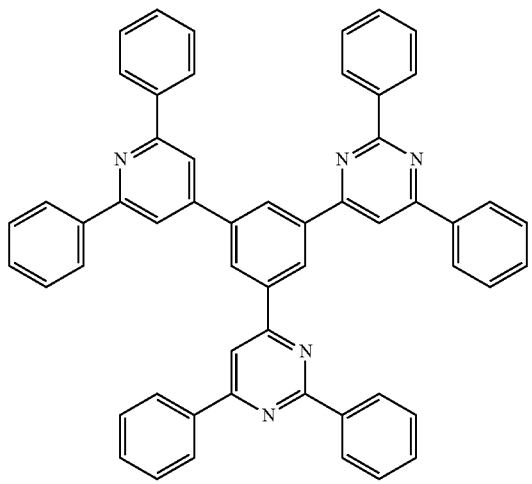
, 143
-continued
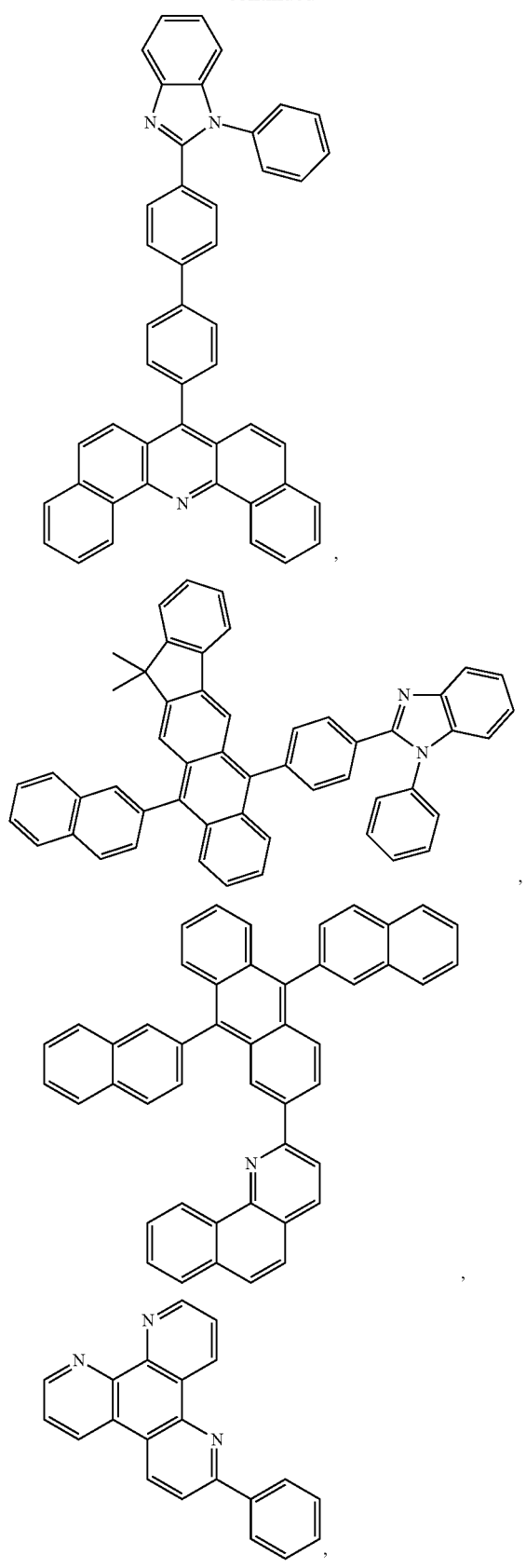
144
-continued
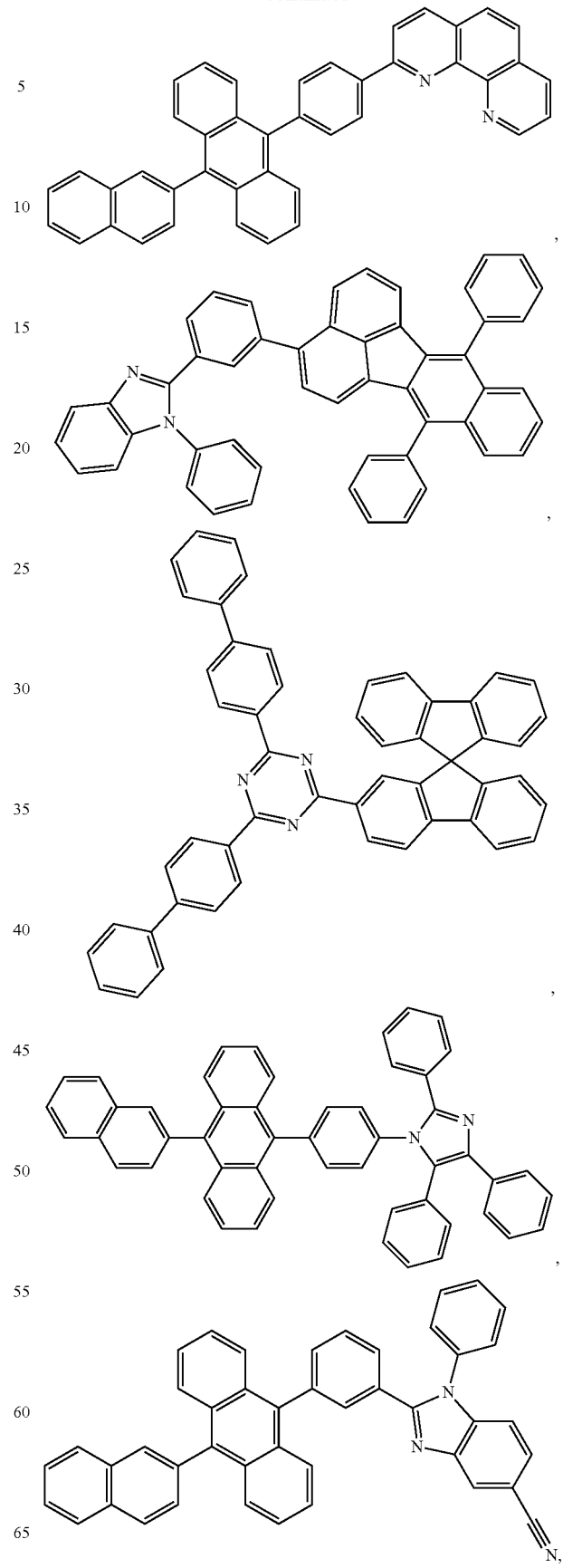

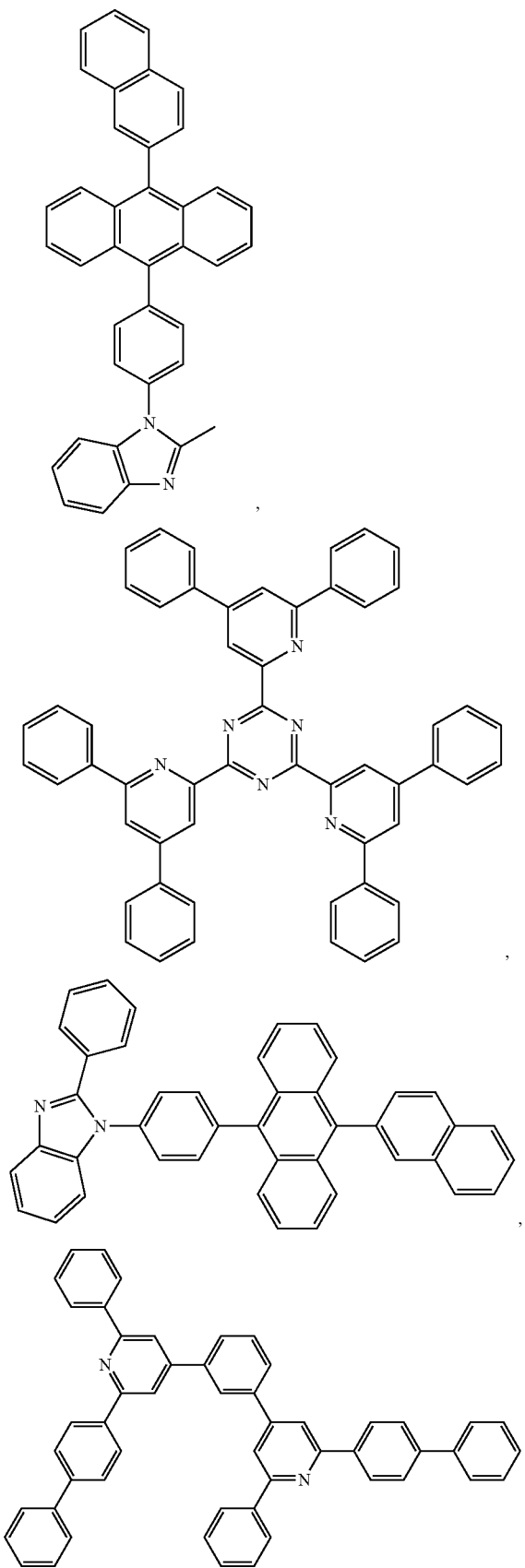

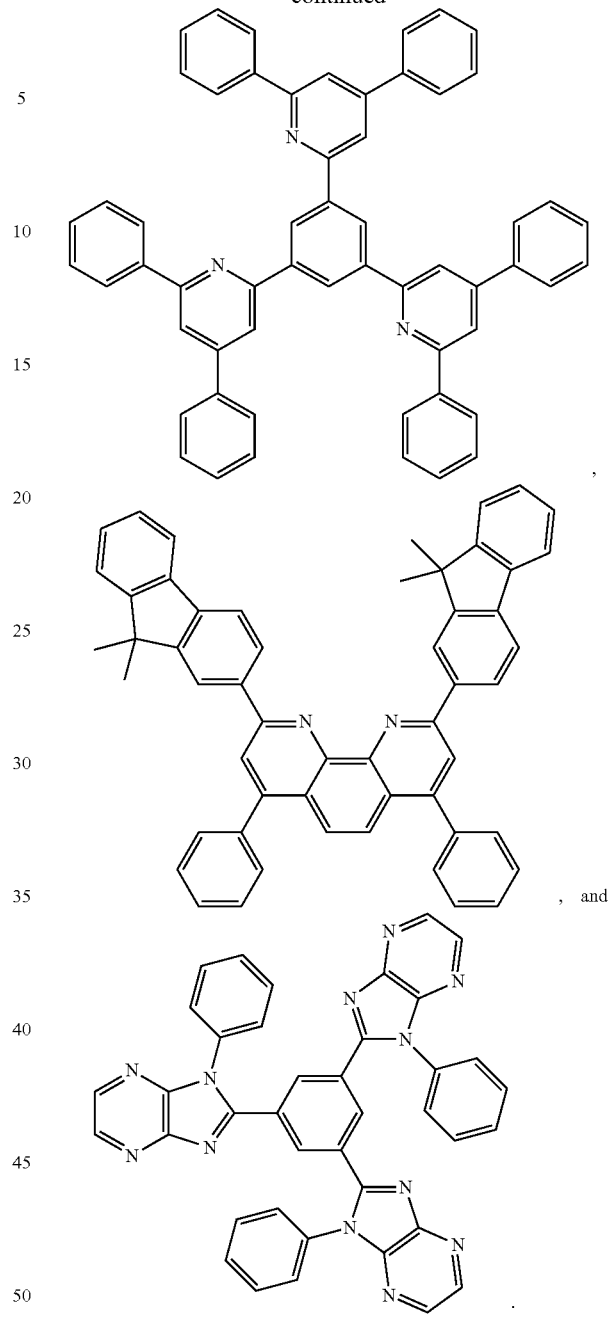

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

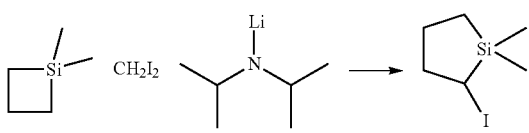

A 2-neck 500 Ml round bottom flask with an addition funnel was dried under vacuum and charged with THF (270 mL), 1,1-dimethylsiletane (13.6 g, 136 mmol), diiodomethane (14.6 mL, 181 mmol) and cooled to −78° C. Freshly prepared lithium diisopropylamide solution in THF (280 mL, 181 mmol) was added dropwise via addition funnel. Once the addition was complete, the yellow/brown suspension was allowed to stir at −78° C. for 30 minutes, then allowed to warm to room temperature overnight. The reaction solution was poured into ~200 mL sat. aq. NH$_4$Cl and extracted with EtOAc. The organic layer was washed with brine, dried over sodium sulfate, filtered and concentrated to a brown oil. The crude product was purified by column chromatography in 100% heptanes, providing 27 g (83% yield) of the desired product as a clear, colorless oil.

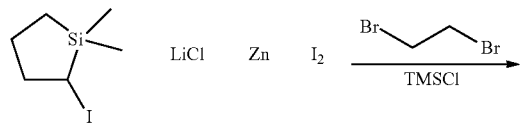

Zinc (3.81 g, 58.3 mmol) and lithium chloride (2.47 g, 58.3 mmol) were dried under vacuum and cooled to room temperature. The reagents were suspended in THF (120 mL) and treated with 1,2-dibromoethane (0.93 ml, 10.78 mmol). The mixture was heated to 75° C. for 30 minutes, then cooled to room temperature. A solution of diiodine (0.74 g, 2.91 mmol) and chlorotrimethylsilane (1.12 mL, 8.74 mmol) in THF (13.3 mL) was added and the reaction was heated to 60° C. for 30 minutes. Upon cooling to room temperature, 2-iodo-1,1-dimethylsilolane (7.00 g, 29.1 mmol) was added via syringe and the reaction was heated at 50° C. overnight. The hazy, gray solution was used without purification.

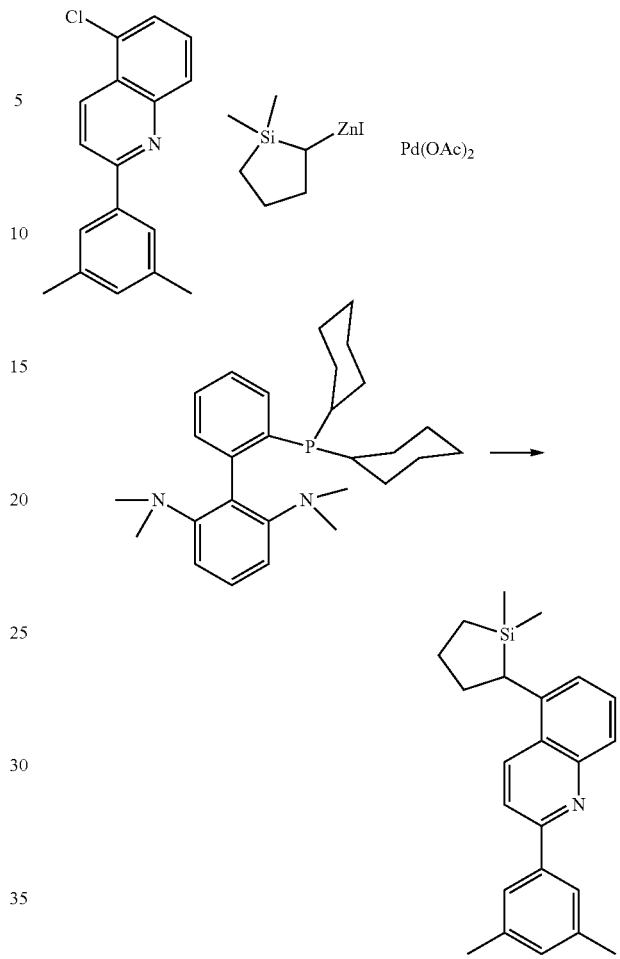

A 500 mL round bottom flask was charged with 5-chloro-2-(3,5-dimethylphenyl)quinoline (5.00 g, 18.7 mmol), diacetoxypalladium (0.168 g, 0.747 mmol), 2'-(dicyclohexylphosphanyl)-N$^2$,N$^2$,N$^6$,N$^6$-tetramethyl-[1,1'-biphenyl]-2,6-diamine (0.65 g, 1.49 mmol), and THF (190 mL) and degassed with nitrogen. (1,1-dimethylsilolan-2-yl)zinc(II) iodide (140 mL, 28.0 mmol) was added via syringe and the reaction was stirred at room temperature for 16 hours. The reaction was diluted with EtOAc, washed with sat. aq. NaHCO$_3$ and brine, dried over sodium sulfate filtered and concentrated. The product was purified by column chromatography in 50-75% DCM/heptanes. The pure fractions were combined and concentrated to 4.00 g of viscous oil. Further purification was achieved by reverse phase column chromatography in 90-100% CH$_3$CN/H$_2$O, followed by recrystallization from MeOH, providing 2.00 g (31% yield) of the title compound as a colorless, viscous oil.

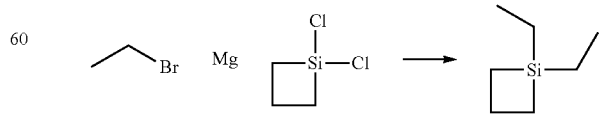

A 500 mL 2-neck round bottom flask was charged with magnesium (10.15 g, 418 mmol) and dried under vacuum. 10 mL of diethyl ether was added, followed by a dropwise addition of bromoethane (28.3 mL, 380 mmol) until initiation was observed. The remaining diethyl ether (190 ml) was added and the remaining bromoethane (28.3 mL, 380 mmol) was added dropwise at a rate to maintain reflux. Once the addition was complete, the reaction was allowed to stir at room temperature for ~30 minutes. The Grignard reagent was then added via cannula to a room temperature solution of 1,1-dichlorosiletane (15.0 mL, 127 mmol) in diethyl ether (127 mL) at a rate to maintain gentle reflux. The reaction solution was then allowed to stir at room temperature for 48 hours. The reaction solution was cooled in an ice bath and quenched cautiously with sat. aq. NH₄Cl. The organic layer was extracted with ether, washed with brine, and dried over MgSO₄. The organics were concentrated to a pale yellow oil. 10.6 g (65% yield) obtained as pale, yellow liquid and used without further purification.

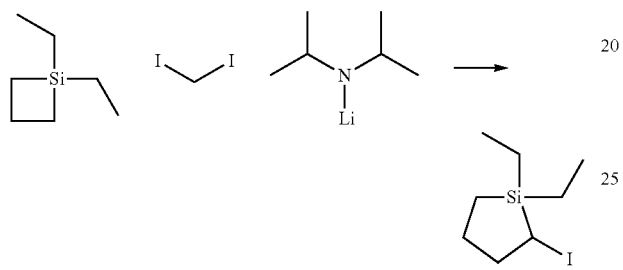

A dry 500 mL round bottom flask was charged with anhydrous THF (166 mL), 1,1-diethylsiletane (10.6 g, 83.0 mmol), diiodomethane (8.9 mL, 111 mmol) and cooled to −78° C. Lithium diisopropylamide (170 mL, 111 mmol) was then added dropwise. The reaction was gradually warmed to room temperature and quenched by pouring into sat. aq. NH₄Cl and extracted with ether. The organic layer was washed with brine, dried over MgSO₄, filtered and concentrated. The crude product was purified by column chromatography in 100% heptanes. Fractions containing product were combined and concentrated to 18.0 g (81% yield) to provide a clear, colorless oil. The product was stored over copper wire.

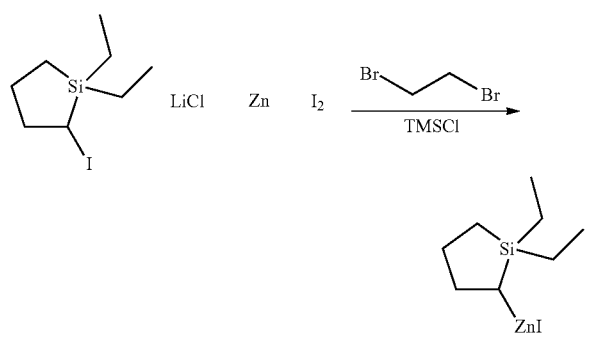

Zinc (2.93 g, 44.7 mmol) and lithium chloride (1.90 g, 44.7 mmol) were dried under vacuum and cooled to room temperature. The reagents were suspended in THF (90 mL) and treated with 1,2-dibromoethane (0.71 mL, 8.28 mmol). The mixture was heated to 75° C. for 30 minutes, and then cooled to room temperature. A solution of diiodine (0.57 g, 2.24 mmol) and chlorotrimethylsilane (0.86 mL, 6.71 mmol) in THF (10.2 mL) was added and the reaction was heated to 60° C. for 30 minutes. After cooling to room temperature 1,1-diethyl-2-iodosilolane (6.00 g, 22.4 mmol) was added via syringe and the reaction was heated at 50° C. for 16 hrs. The hazy, gray solution was used without further purification.

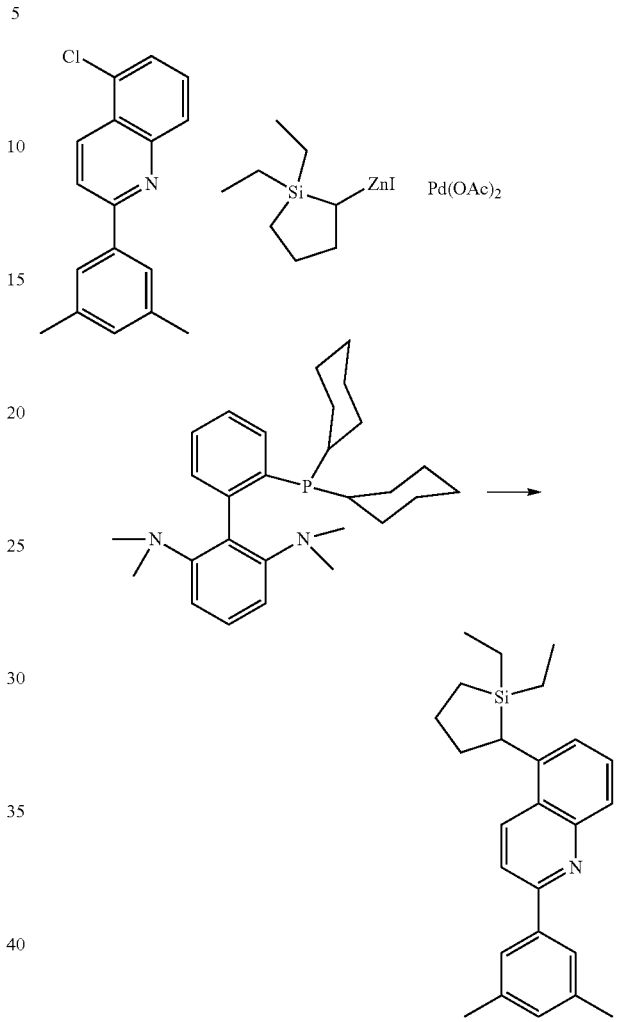

A 100 mL round bottom flask was charged with 5-chloro-2-(3,5-dimethylphenyl)quinoline (3.20 g, 11.9 mmol), diacetoxypalladium (0.11 g, 0.48 mmol), 2'-(dicyclohexylphosphanyfi-N²,N²,N⁶,N⁶-tetramethyl-[1,1'-biphenyl]-2,6-diamine (0.42 g, 0.96 mmol), and THF (120 mL) and degassed with nitrogen. (1,1-diethylsilolan-2-yl)zinc(II) iodide (96 mL, 19.1 mmol) was added via syringe and the reaction was stirred at room temperature for 4 days. The reaction solution was washed with sat. aq. NaHCO₃ and brine, dried over sodium sulfate, filtered and concentrated. The crude product was purified by column chromatography in 3-5% EtOAc/heptanes. Further purification was achieved by reverse phase column chromatography in 90-100% acetonitrile/water, yielding 4.00 g (90% yield) of the desired compound as a pale yellow, viscous oil.

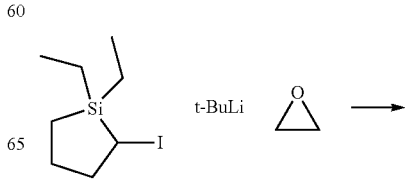

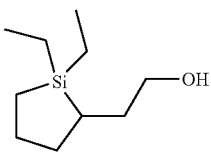

A dry 100 mL round bottom flask was charged with hexanes (35 mL) and diethyl ether (1.9 mL) and degassed with nitrogen. tert-butyllithium (6.6 mL, 11.2 mmol) was added and the reaction solution was cooled to −78° C. 1,1-diethyl-2-iodosilolane (1.00 g, 3.73 mmol) was added via syringe and the reaction was stirred for 10 minutes before quenching with a solution of oxirane in THF (2.5 mL, 7.5 mmol). The reaction was stirred for 10 minutes, then removed from the bath and allowed to warm gradually to room temperature before quenching with water. The reaction was extracted with EtOAc, washed with water, brine and dried over sodium sulfate. The organics were concentrated to an orange oil and purified by column chromatography in 5-20% EtOAc/heptanes, providing 0.50 g (72% yield) of the title compound as a clear, colorless oil.

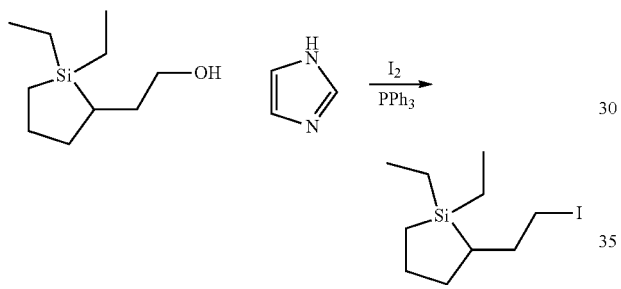

Triphenylphosphane (3.74 g, 14.37 mmol) was dissolved in DCM (30 mL) and treated sequentially with 1H-imidazole (0.97 g, 14.27 mmol) and diiodine (3.62 g, 14.27 mmol) at room temperature. The yellow solution was stirred for 15 minutes at room temperature, and then treated with a solution of 2-(1,1-diethylsilolan-2-yl)ethan-1-ol (1.90 g, 10.19 mmol) in DCM (4.0 mL) and stirred at room temperature for 16 hours. The solvent was removed in vacuo and the crude orange product thus obtained was purified by vacuum distillation using a Kugelrohr, providing 1.60 g (53% yield) of the title compound as a clear, colorless oil.

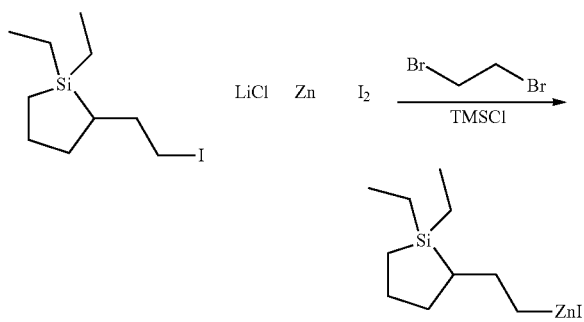

Zinc (0.71 g, 10.80 mmol) and lithium chloride (0.46 g, 10.80 mmol) were dried under vacuum and cooled to room temperature. The reagents were suspended in THF (22.1 mL) and treated with 1,2-dibromoethane (0.17 mL, 2.00 mmol). The mixture was heated to 75° C. for 30 minutes, then cooled to room temperature. A solution of diiodine (0.14 g, 0.54 mmol) and chlorotrimethylsilane (0.21 mL, 1.62 mmol) in THF (2.6 mL) was added and the reaction was heated to 60° C. for 30 minutes. Upon cooling to room temperature, 1,1-diethyl-2-(2-iodoethyl)silolane (1.60 g, 5.40 mmol) was added via syringe and the reaction was heated at 50° C. for 16 hours. The hazy, gray solution was used without further purification.

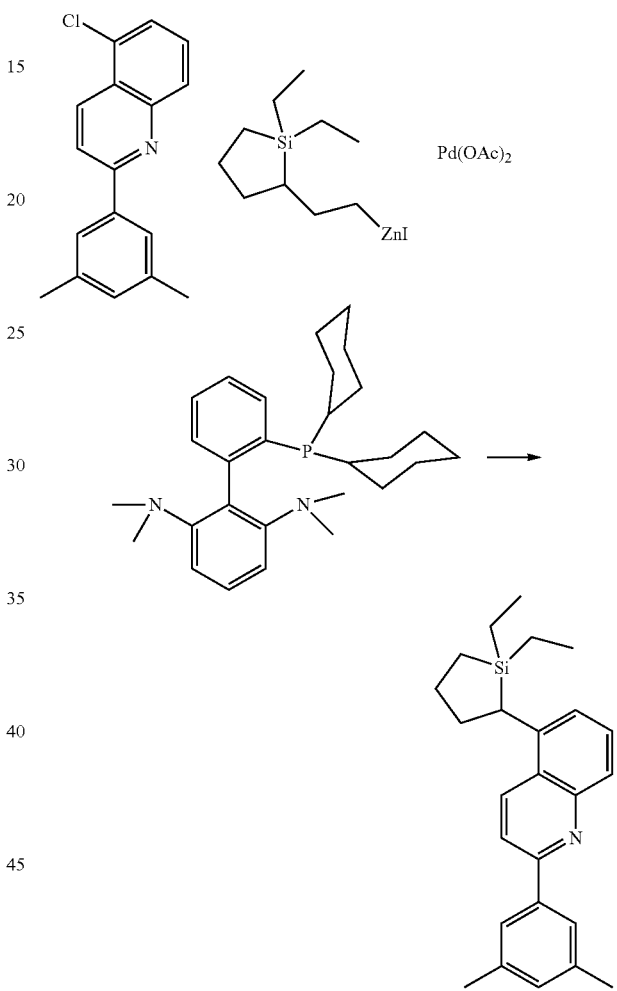

A 250 mL round bottom flask was charged with 5-chloro-2-(3,5-dimethylphenyl)quinoline (0.75 g, 2.80 mmol), diacetoxypalladium (0.025 g, 0.112 mmol), 2'-(dicyclohexylphosphanyl)-$N^2,N^2,N^6,N^6$-tetramethyl-[1,1'-biphenyl]-2,6-diamine (0.098 g, 0.224 mmol), and THF (28 mL) and degassed with nitrogen. (2-(1,1-diethylsilolan-2-yl)ethyl)zinc(II) iodide (25 mL, 5.0 mmol) was added via syringe and the reaction was stirred at room temperature for 16 hours. The organics were washed with sat. aq. NaHCO$_3$ and brine, dried over sodium sulfate, filtered and concentrated. The crude product was purified by column chromatography in 2% EtOAc/heptanes, providing 0.80 g (71% yield) of the title compound as a viscous oil.

All the above ligands may be complexated into Ir metal complexes following the standard procedure. A non-limiting example is shown below:

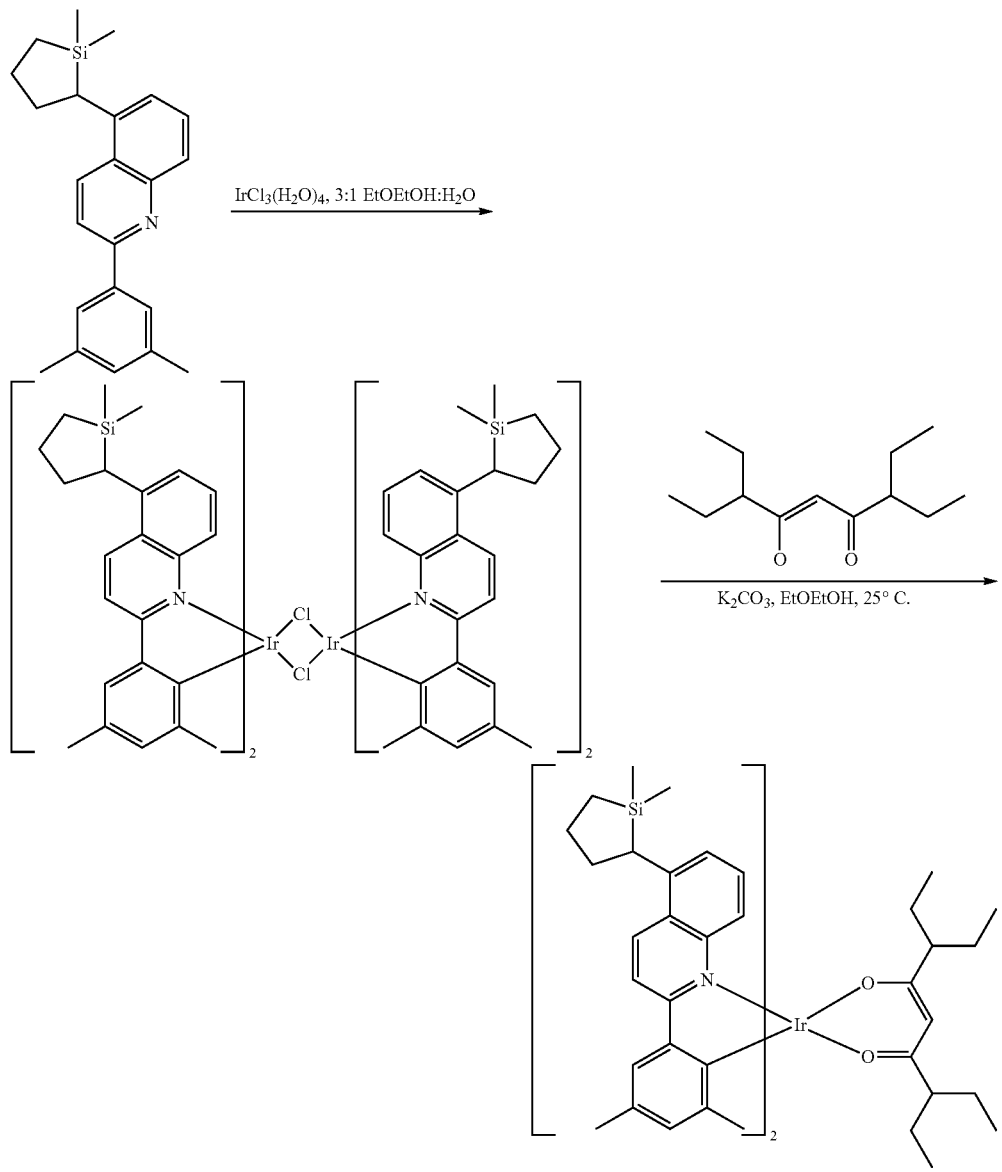

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A composition comprising a first compound;
wherein the first compound is capable of functioning as an emitter in an organic light emitting device at room temperature;
wherein the first compound has at least one aromatic ring and at least one substituent R;
wherein each of the at least one substituent R is directly bonded to one of the aromatic rings;
wherein each of the at least one substituent R has the formula

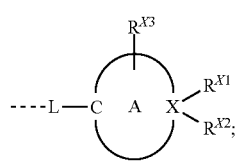

wherein L is a direct bond or an organic linker;
wherein ring A is a non-aromatic cyclic group containing X;
wherein L bonds to ring A at a carbon atom C;
wherein X is Si or Ge;
wherein $R^{X3}$ represents mono to the possible maximum number of substitution, or no substitution;

wherein $R^{X1}$, $R^{X2}$ and $R^{X3}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substituents $R^{X1}$, $R^{X2}$ and $R^{X3}$ are optionally joined or fused into a ring.

2. The composition of claim 1, wherein L is a direct bond.

3. The composition of claim 1, wherein L is an organic linker selected from the group consisting of: $NR^{X4}$, $SiR^{X4}R^{X5}$, $GeR^{X4}R^{X5}$, alkyl, cycloalkyl, and combinations thereof; and wherein $R^{X4}$ and $R^{X5}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any adjacent substituents $R^{X1}$, $R^{X2}$ and $R^{X3}$, $R^{X4}$ and $R^{X5}$ are optionally joined or fused into a ring.

4. The composition of claim 1, wherein $R^{X1}$ and $R^{X2}$ are joined or fused into a ring.

5. The composition of claim 1, wherein ring A consists of atoms selected from the group consisting of C, Si, Ge, N, O, and S.

6. The composition of claim 5, wherein ring A is selected from the group consisting of:

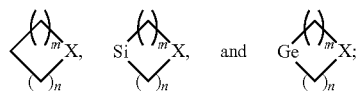

wherein m and n are each independently an integer of 1 to 5.

7. The composition of claim 1, wherein in each of the at least one substituent R, ring A is monocyclic or a bicyclic group.

8. The composition of claim 1, wherein the first compound is capable of functioning as a phosphorescent emitter, a fluorescent emitter, or a delayed fluorescent emitter in an organic light emitting device at room temperature.

9. The composition of claim 1, wherein the first compound is a metal coordination complex having a metal-carbon bond.

10. The composition of claim 1, wherein the first compound has the formula of $M(L^1)_x(L^2)_y(L^3)_z$;

wherein $L^1$, $L^2$ and $L^3$ can be the same or different;

wherein x is 1, 2, or 3;

wherein y is 0, 1, or 2;

wherein z is 0, 1, or 2;

wherein x+y+z is the oxidation state of the metal M;

wherein $L^1$, $L^2$ and $L^3$ are each independently selected from the group consisting of:

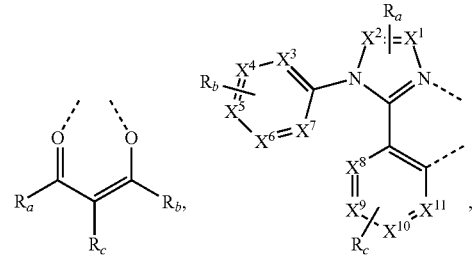

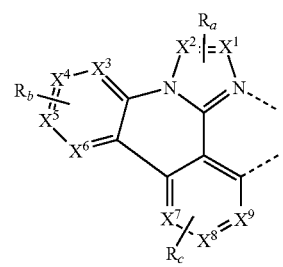

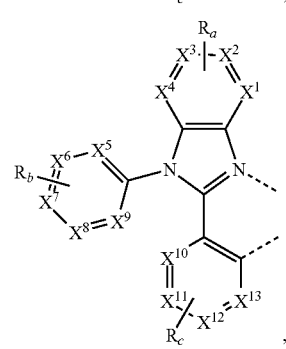

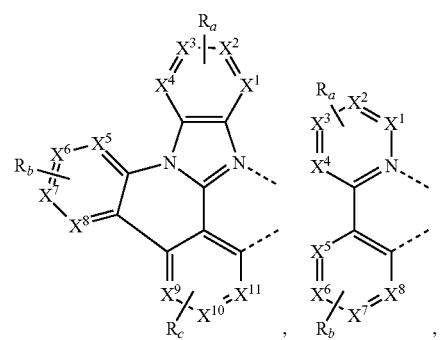

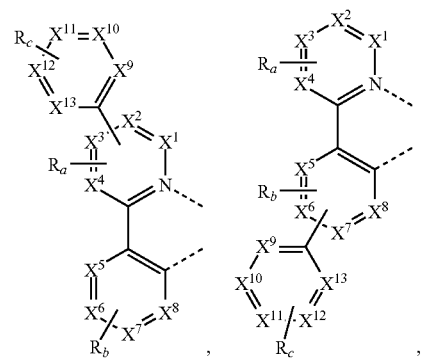

-continued

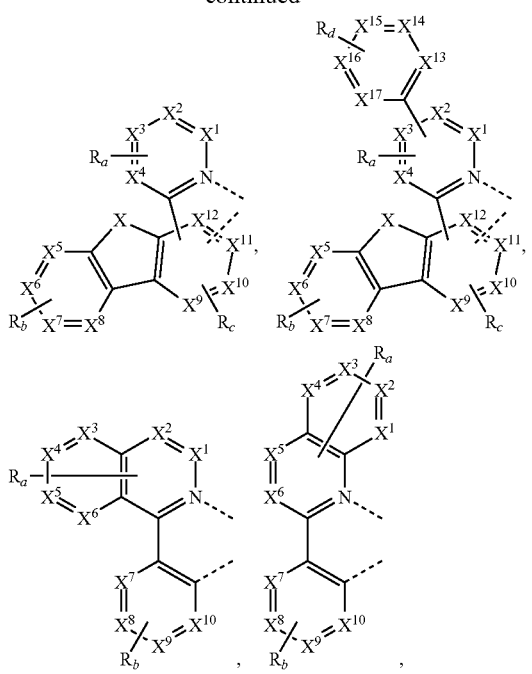

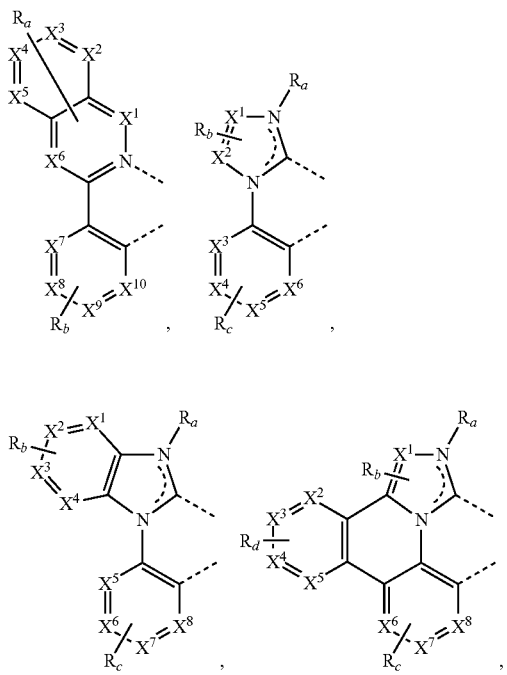

-continued

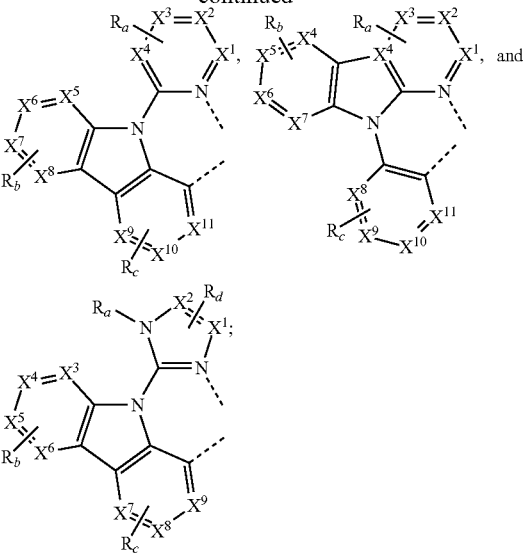

wherein each $X^1$ to $X^{17}$ are independently selected from the group consisting of carbon and nitrogen;

wherein X is selected from the group consisting of BR', NR', PR', O, S, Se, C=O, S=O, SO$_2$, CR'R'', SiR'R'', and GeR'R'';

wherein R' and R'' are optionally fused or joined to form a ring;

wherein each $R_a$, $R_b$, $R_c$, and $R_d$ may represent from mono substitution to the possible maximum number of substitution, or no substitution;

wherein R', R'', $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any two adjacent substituents of $R_a$, $R_b$, $R_c$, and $R_d$ are optionally fused or joined to form a ring or form a multidentate ligand; and wherein at least one of the $R_a$, $R_b$, $R_c$, and $R_d$ includes at least one substituent R.

11. The composition of claim 10, wherein the first compound has the formula selected from the group consisting of $Ir(L^1)_2(L^2)$, $Pt(L^1)_2$ and $Pt(L^1)(L^2)$.

12. The composition of claim 1, wherein each of the at least one substituent R is independently selected from the group consisting of:

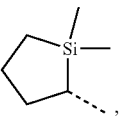

$R^{41}$

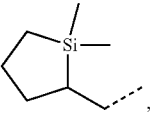

$R^{42}$

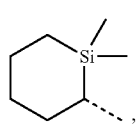,
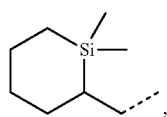,
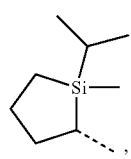,
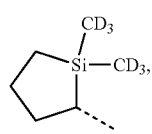,
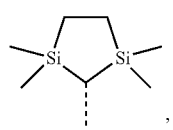,
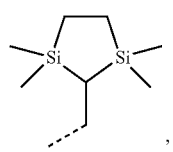,
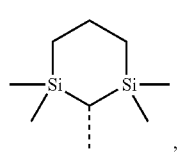,
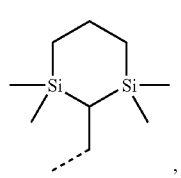,
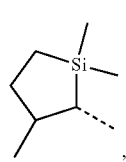,
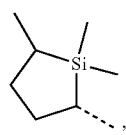,
$R^{A3}$
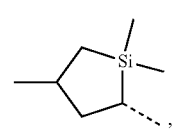,
$R^{A4}$
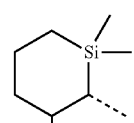,
$R^{A5}$
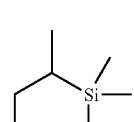,
$R^{A6}$
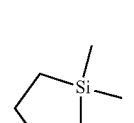,
$R^{A7}$
$R^{A8}$
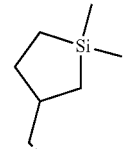,
$R^{A9}$
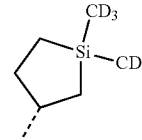,
$R^{A10}$
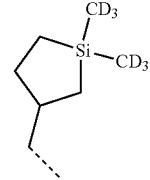,
$R^{A11}$
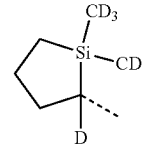,
$R^{A12}$
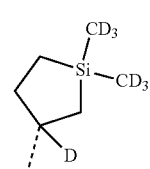,
$R^{A13}$
$R^{A14}$
$R^{A15}$
$R^{A16}$
$R^{A17}$
$R^{A18}$
$R^{A19}$
$R^{A20}$
$R^{A21}$

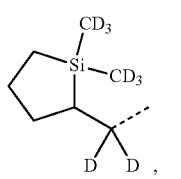,
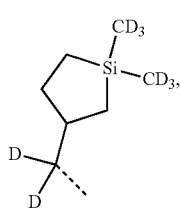,
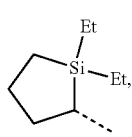,
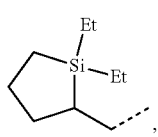,
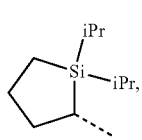,
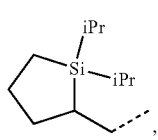,
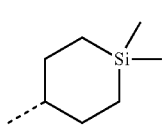,
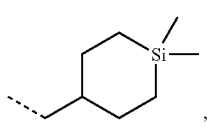,
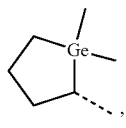,
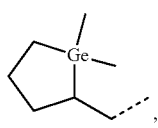,
| | |
|---|---|
| $R^{A22}$ | 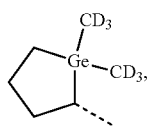, |
| $R^{A23}$ | 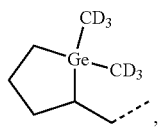, |
| | 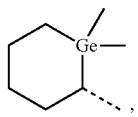, |
| $R^{A24}$ | 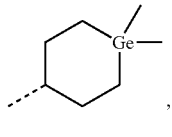, |
| $R^{A25}$ | |
| $R^{A26}$ | 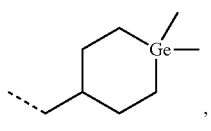, |
| $R^{A27}$ | 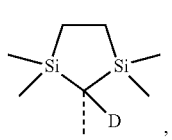, |
| $R^{A28}$ | 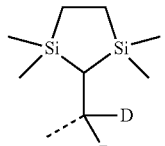, |
| $R^{A29}$ | |
| $R^{A30}$ | 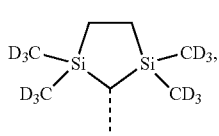, |
| $R^{A31}$ | 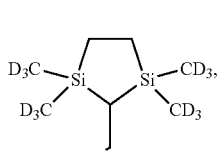, |
| | 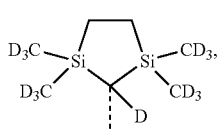, |
$R^{A32}$
$R^{A33}$
$R^{A34}$
$R^{A35}$
$R^{A36}$
$R^{A37}$
$R^{A38}$
$R^{A39}$
$R^{A40}$
$R^{A41}$
$R^{A42}$ -continued
R^A443 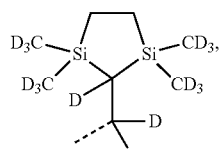
R^A444 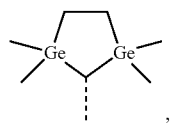
R^A445 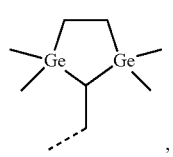
R^A446 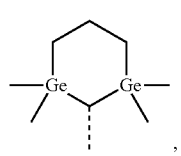
R^A447 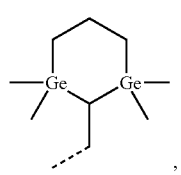
R^A448 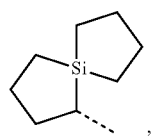
R^A449 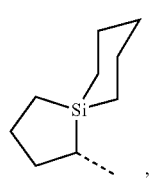
R^A450 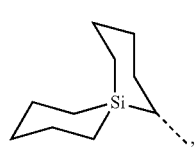
R^A451 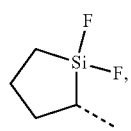
R^A452 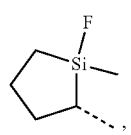
-continued
R^A453 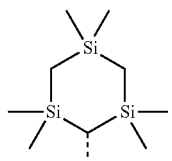
R^A454 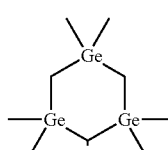
R^A455 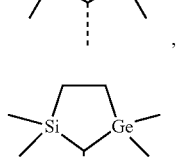
R^A456 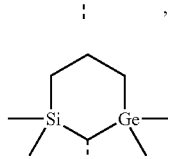
R^A457 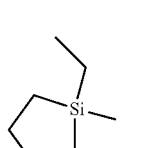
R^A458 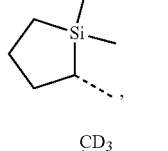
R^A459 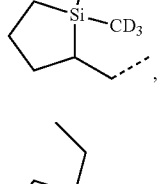, and
R^A460 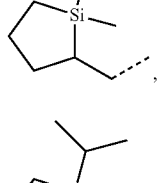.
13. The composition of claim 10, wherein at least one of $L^1$, $L^2$, and $L^3$ is selected from the group consisting of:
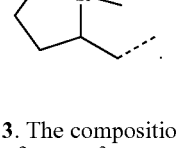

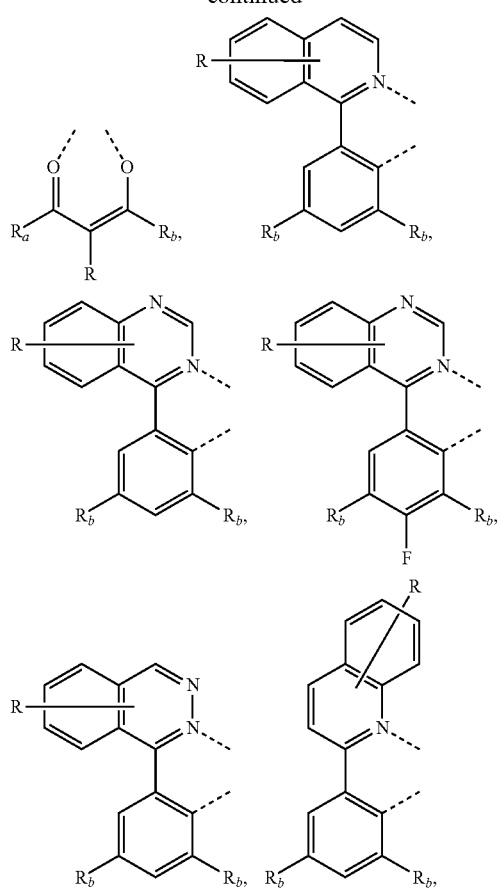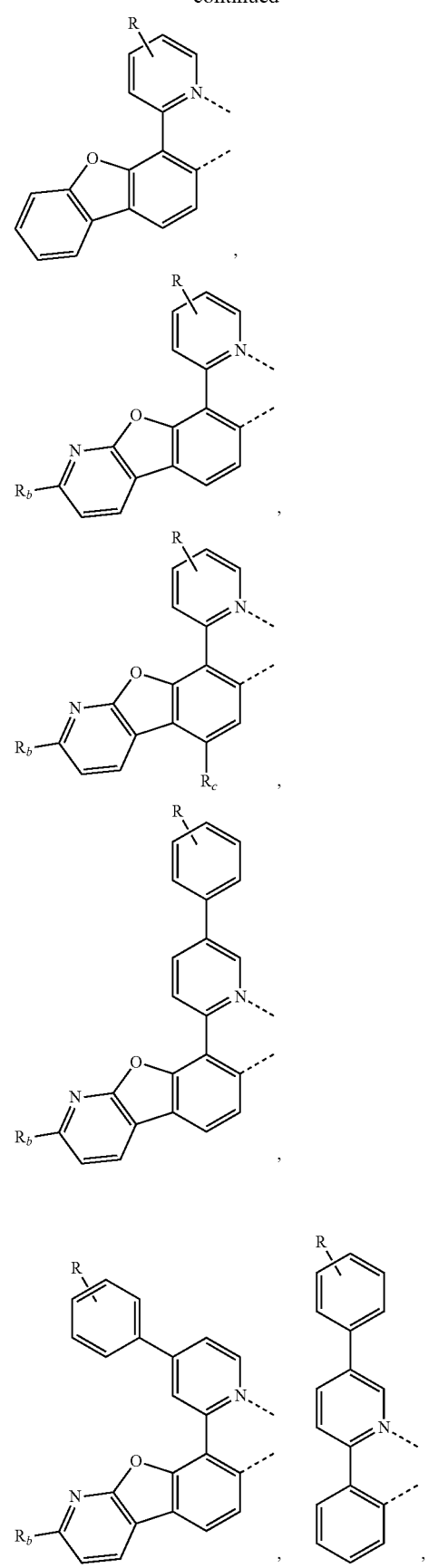

-continued
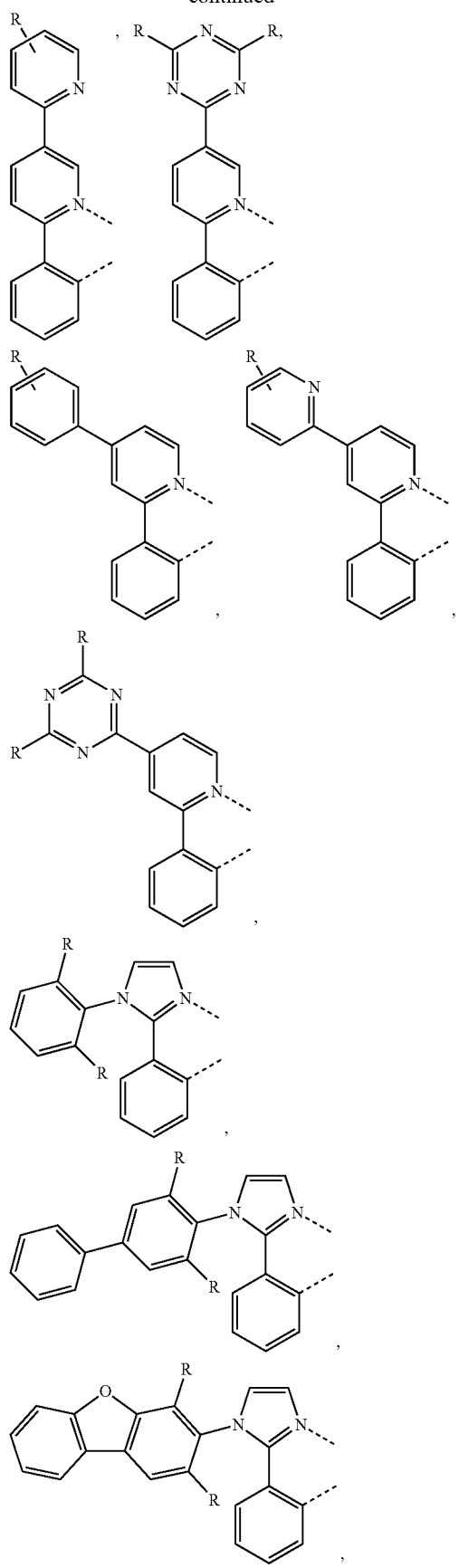
-continued
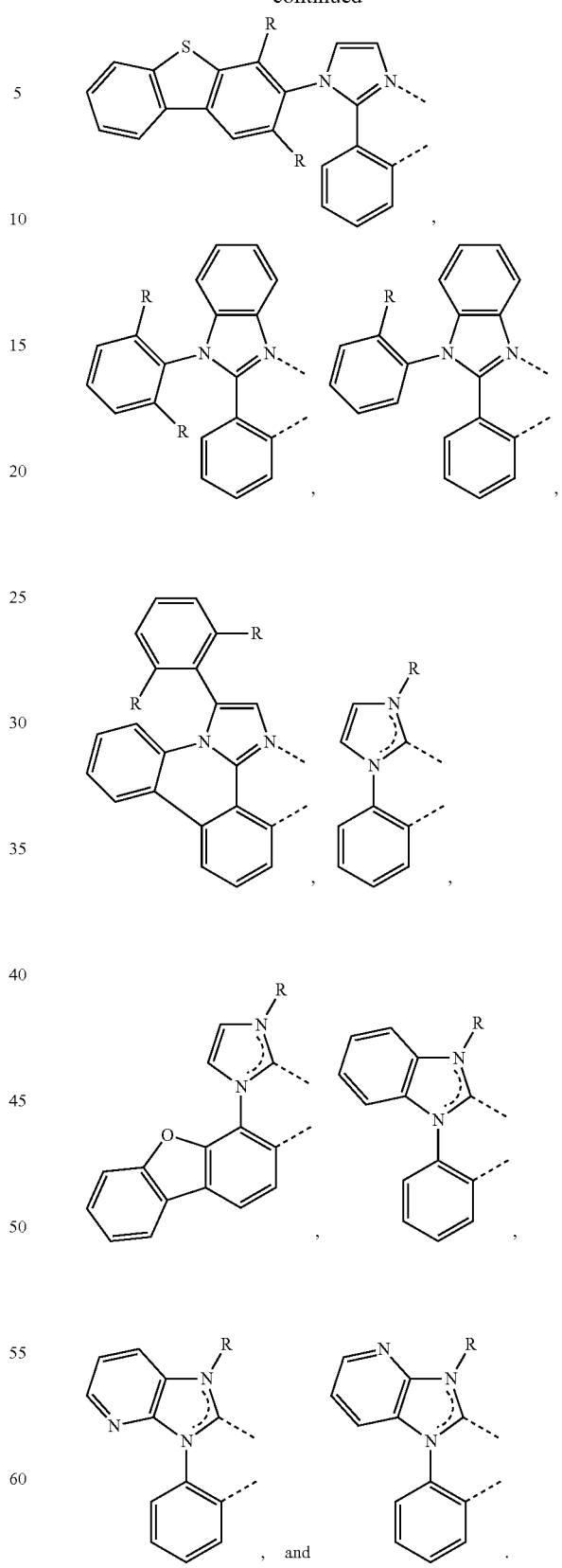
14. The composition of claim 10, wherein at least one of $L^1$, $L^2$, and $L^3$ is selected from the group consisting of:

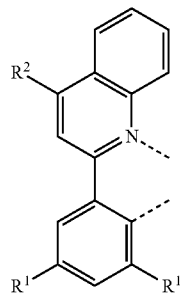

R² = R^A1, R¹ = R^B1, L_A1
R² = R^A2, R¹ = R^B1, L_A2
R² = R^A3, R¹ = R^B1, L_A3
R² = R^A4, R¹ = R^B1, L_A4
R² = R^A5, R¹ = R^B1, L_A5
R² = R^A1, R¹ = R^B2, L_A6
R² = R^A2, R¹ = R^B2, L_A7
R² = R^A3, R¹ = R^B2, L_A8
R² = R^A4, R¹ = R^B2, L_A9
R² = R^A5, R¹ = R^B2, L_A10

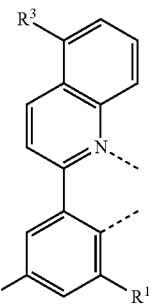

R³ = R^A1, R¹ = R^B1, L_A11
R³ = R^A2, R¹ = R^B1, L_A12
R³ = R^A3, R¹ = R^B1, L_A13
R³ = R^A4, R¹ = R^B1, L_A14
R³ = R^A5, R¹ = R^B1, L_A15
R³ = R^A1, R¹ = R^B2, L_A16
R³ = R^A2, R¹ = R^B2, L_A17
R³ = R^A3, R¹ = R^B2, L_A18
R³ = R^A4, R¹ = R^B2, L_A19
R³ = R^A5, R¹ = R^B2, L_A20

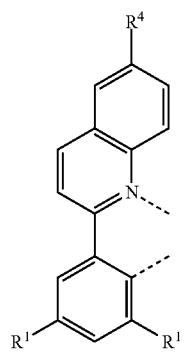

R⁴ = R^A1, R¹ = R^B1, L_A21
R⁴ = R^A2, R¹ = R^B1, L_A22
R⁴ = R^A3, R¹ = R^B1, L_A23
R⁴ = R^A4, R¹ = R^B1, L_A24
R⁴ = R^A5, R¹ = R^B1, L_A25
R⁴ = R^A1, R¹ = R^B2, L_A26
R⁴ = R^A2, R¹ = R^B2, L_A27
R⁴ = R^A3, R¹ = R^B2, L_A28
R⁴ = R^A4, R¹ = R^B2, L_A29
R⁴ = R^A5, R¹ = R^B2, L_A30

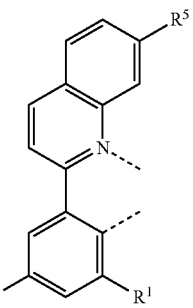

R⁵ = R^A1, R¹ = R^B1, L_A31
R⁵ = R^A2, R¹ = R^B1, L_A32
R⁵ = R^A3, R¹ = R^B1, L_A33
R⁵ = R^A4, R¹ = R^B1, L_A34
R⁵ = R^A5, R¹ = R^B1, L_A35
R⁵ = R^A1, R¹ = R^B2, L_A36
R⁵ = R^A2, R¹ = R^B2, L_A37
R⁵ = R^A3, R¹ = R^B2, L_A38
R⁵ = R^A4, R¹ = R^B2, L_A39
R⁵ = R^A5, R¹ = R^B2, L_A40

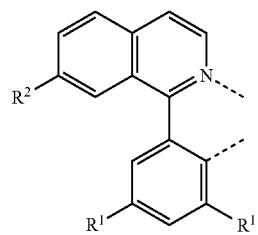

R² = R^A1, R¹ = R^B1, L_A41
R² = R^A2, R¹ = R^B1, L_A42
R² = R^A3, R¹ = R^B1, L_A43
R² = R^A4, R¹ = R^B1, L_A44
R² = R^A5, R¹ = R^B1, L_A45
R² = R^A1, R¹ = R^B2, L_A46
R² = R^A2, R¹ = R^B2, L_A47
R² = R^A3, R¹ = R^B2, L_A48
R² = R^A4, R¹ = R^B2, L_A49
R² = R^A5, R¹ = R^B2, L_A50

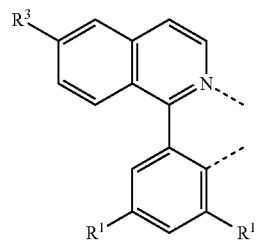

R³ = R^A1, R¹ = R^B1, L_A51
R³ = R^A2, R¹ = R^B1, L_A52
R³ = R^A3, R¹ = R^B1, L_A53
R³ = R^A4, R¹ = R^B1, L_A54
R³ = R^A5, R¹ = R^B1, L_A55
R³ = R^A1, R¹ = R^B2, L_A56
R³ = R^A2, R¹ = R^B2, L_A57
R³ = R^A3, R¹ = R^B2, L_A58
R³ = R^A4, R¹ = R^B2, L_A59
R³ = R^A5, R¹ = R^B2, L_A60

-continued

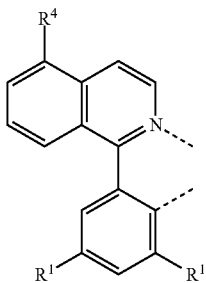

R⁴ = R^{A1}, R¹ = R^{B1}, L_{A61}
R⁴ = R^{A2}, R¹ = R^{B1}, L_{A62}
R⁴ = R^{A3}, R¹ = R^{B1}, L_{A63}
R⁴ = R^{A4}, R¹ = R^{B1}, L_{A64}
R⁴ = R^{A5}, R¹ = R^{B1}, L_{A65}
R⁴ = R^{A1}, R¹ = R^{B2}, L_{A66}
R⁴ = R^{A2}, R¹ = R^{B2}, L_{A67}
R⁴ = R^{A3}, R¹ = R^{B2}, L_{A68}
R⁴ = R^{A4}, R¹ = R^{B2}, L_{A69}
R⁴ = R^{A5}, R¹ = R^{B2}, L_{A70}

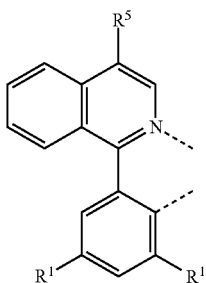

R⁵ = R^{A1}, R¹ = R^{B1}, L_{A71}
R⁵ = R^{A2}, R¹ = R^{B1}, L_{A72}
R⁵ = R^{A3}, R¹ = R^{B1}, L_{A73}
R⁵ = R^{A4}, R¹ = R^{B1}, L_{A74}
R⁵ = R^{A5}, R¹ = R^{B1}, L_{A75}
R⁵ = R^{A1}, R¹ = R^{B2}, L_{A76}
R⁵ = R^{A2}, R¹ = R^{B2}, L_{A77}
R⁵ = R^{A3}, R¹ = R^{B2}, L_{A78}
R⁵ = R^{A4}, R¹ = R^{B2}, L_{A79}
R⁵ = R^{A5}, R¹ = R^{B2}, L_{A80}

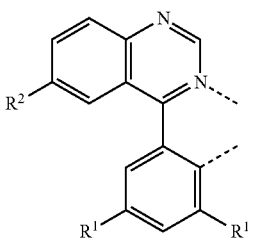

R² = R^{A1}, R¹ = R^{B1}, L_{A81}
R² = R^{A2}, R¹ = R^{B1}, L_{A82}
R² = R^{A3}, R¹ = R^{B1}, L_{A83}
R² = R^{A4}, R¹ = R^{B1}, L_{A84}
R² = R^{A5}, R¹ = R^{B1}, L_{A85}
R² = R^{A1}, R¹ = R^{B2}, L_{A86}
R² = R^{A2}, R¹ = R^{B2}, L_{A87}
R² = R^{A3}, R¹ = R^{B2}, L_{A88}
R² = R^{A4}, R¹ = R^{B2}, L_{A89}
R² = R^{A5}, R¹ = R^{B2}, L_{A90}

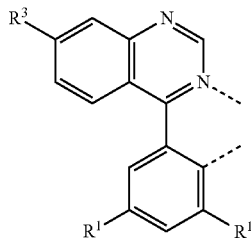

R³ = R^{A1}, R¹ = R^{B1}, L_{91}
R³ = R^{A2}, R¹ = R^{B1}, L_{92}
R³ = R^{A3}, R¹ = R^{B1}, L_{93}
R³ = R^{A4}, R¹ = R^{B1}, L_{94}
R³ = R^{A5}, R¹ = R^{B1}, L_{95}
R³ = R^{A1}, R¹ = R^{B2}, L_{96}
R³ = R^{A2}, R¹ = R^{B2}, L_{97}
R³ = R^{A3}, R¹ = R^{B2}, L_{98}
R³ = R^{A4}, R¹ = R^{B2}, L_{99}
R³ = R^{A5}, R¹ = R^{B2}, L_{A100}

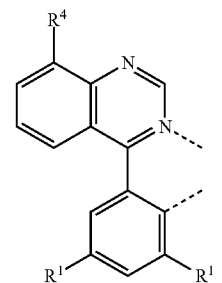

R⁴ = R^{A1}, R¹ = R^{B1}, L_{A101}
R⁴ = R^{A2}, R¹ = R^{B1}, L_{A102}
R⁴ = R^{A3}, R¹ = R^{B1}, L_{A103}
R⁴ = R^{A4}, R¹ = R^{B1}, L_{A104}
R⁴ = R^{A5}, R¹ = R^{B1}, L_{A105}
R⁴ = R^{A1}, R¹ = R^{B2}, L_{A106}
R⁴ = R^{A2}, R¹ = R^{B2}, L_{A107}
R⁴ = R^{A3}, R¹ = R^{B2}, L_{A108}
R⁴ = R^{A4}, R¹ = R^{B2}, L_{A109}
R⁴ = R^{A5}, R¹ = R^{B2}, L_{A110}

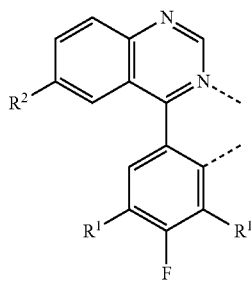

R² = R^{A1}, R¹ = R^{B1}, L_{A111}
R² = R^{A2}, R¹ = R^{B1}, L_{A112}
R² = R^{A3}, R¹ = R^{B1}, L_{A113}
R² = R^{A4}, R¹ = R^{B1}, L_{A114}
R² = R^{A5}, R¹ = R^{B1}, L_{A115}
R² = R^{A1}, R¹ = R^{B2}, L_{A116}
R² = R^{A2}, R¹ = R^{B2}, L_{A117}
R² = R^{A3}, R¹ = R^{B2}, L_{A118}
R² = R^{A4}, R¹ = R^{B2}, L_{A119}
R² = R^{A5}, R¹ = R^{B2}, L_{A120}

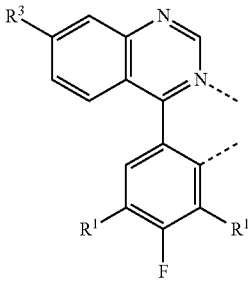

R³ = R^{A1}, R¹ = R^{B1}, L_{A121}
R³ = R^{A2}, R¹ = R^{B1}, L_{A122}
R³ = R^{A3}, R¹ = R^{B1}, L_{A123}
R³ = R^{A4}, R¹ = R^{B1}, L_{A124}
R³ = R^{A5}, R¹ = R^{B1}, L_{A125}
R³ = R^{A1}, R¹ = R^{B2}, L_{A126}
R³ = R^{A2}, R¹ = R^{B2}, L_{A127}
R³ = R^{A3}, R¹ = R^{B2}, L_{A128}
R³ = R^{A4}, R¹ = R^{B2}, L_{A129}
R³ = R^{A5}, R¹ = R^{B2}, L_{A130}

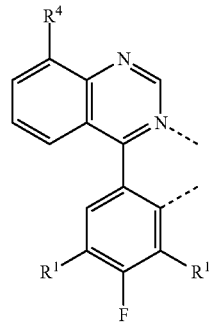

R⁴ = R^{A1}, R¹ = R^{B1}, L_{A131}
R⁴ = R^{A2}, R¹ = R^{B1}, L_{A132}
R⁴ = R^{A3}, R¹ = R^{B1}, L_{A133}
R⁴ = R^{A4}, R¹ = R^{B1}, L_{A134}
R⁴ = R^{A5}, R¹ = R^{B1}, L_{A135}
R⁴ = R^{A1}, R¹ = R^{B2}, L_{A136}
R⁴ = R^{A2}, R¹ = R^{B2}, L_{A137}
R⁴ = R^{A3}, R¹ = R^{B2}, L_{A138}
R⁴ = R^{A4}, R¹ = R^{B2}, L_{A139}
R⁴ = R^{A5}, R¹ = R^{B2}, L_{A140}

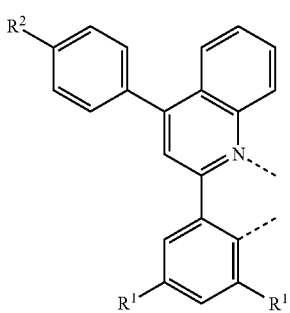

R² = R^{A1}, R¹ = R^{B1}, L_{A141}
R² = R^{A2}, R¹ = R^{B1}, L_{A142}
R² = R^{A3}, R¹ = R^{B1}, L_{A143}
R² = R^{A4}, R¹ = R^{B1}, L_{A144}
R² = R^{A5}, R¹ = R^{B1}, L_{A145}
R² = R^{A1}, R¹ = R^{B2}, L_{A146}
R² = R^{A2}, R¹ = R^{B2}, L_{A147}
R² = R^{A3}, R¹ = R^{B2}, L_{A148}
R² = R^{A4}, R¹ = R^{B2}, L_{A149}
R² = R^{A5}, R¹ = R^{B2}, L_{A150}

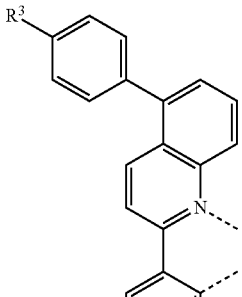

R³ = R^{A1}, R¹ = R^{B1}, L_{A151}
R³ = R^{A2}, R¹ = R^{B1}, L_{A152}
R³ = R^{A3}, R¹ = R^{B1}, L_{A153}
R³ = R^{A4}, R¹ = R^{B1}, L_{A154}
R³ = R^{A5}, R¹ = R^{B1}, L_{A155}
R³ = R^{A1}, R¹ = R^{B2}, L_{A156}
R³ = R^{A2}, R¹ = R^{B2}, L_{A157}
R³ = R^{A3}, R¹ = R^{B2}, L_{A158}
R³ = R^{A4}, R¹ = R^{B2}, L_{A159}
R³ = R^{A5}, R¹ = R^{B2}, L_{A160}

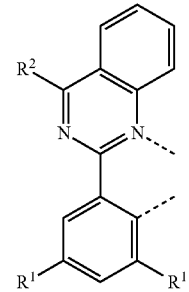

R² = R^{A1}, R¹ = R^{B1}, L_{A161}
R² = R^{A2}, R¹ = R^{B1}, L_{A162}
R² = R^{A3}, R¹ = R^{B1}, L_{A163}
R² = R^{A4}, R¹ = R^{B1}, L_{A164}
R² = R^{A5}, R¹ = R^{B1}, L_{A165}
R² = R^{A1}, R¹ = R^{B2}, L_{A166}
R² = R^{A2}, R¹ = R^{B2}, L_{A167}
R² = R^{A3}, R¹ = R^{B2}, L_{A168}
R² = R^{A4}, R¹ = R^{B2}, L_{A169}
R² = R^{A5}, R¹ = R^{B2}, L_{A170}

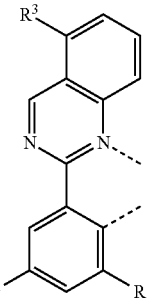

R³ = R^{A1}, R¹ = R^{B1}, L_{A171}
R³ = R^{A2}, R¹ = R^{B1}, L_{A172}
R³ = R^{A3}, R¹ = R^{B1}, L_{A173}
R³ = R^{A4}, R¹ = R^{B1}, L_{A174}
R³ = R^{A5}, R¹ = R^{B1}, L_{A175}
R³ = R^{A1}, R¹ = R^{B2}, L_{A176}
R³ = R^{A2}, R¹ = R^{B2}, L_{A177}
R³ = R^{A3}, R¹ = R^{B2}, L_{A178}
R³ = R^{A4}, R¹ = R^{B2}, L_{A179}
R³ = R^{A5}, R¹ = R^{B2}, L_{A180}

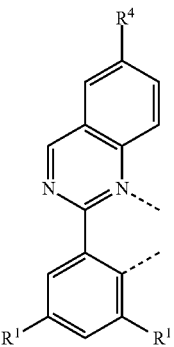

R⁴ = R^A1, R¹ = R^B1, L_A181
R⁴ = R^A2, R¹ = R^B1, L_A182
R⁴ = R^A3, R¹ = R^B1, L_A183
R⁴ = R^A4, R¹ = R^B1, L_A184
R⁴ = R^A5, R¹ = R^B1, L_A185
R⁴ = R^A1, R¹ = R^B2, L_A186
R⁴ = R^A2, R¹ = R^B2, L_A187
R⁴ = R^A3, R¹ = R^B2, L_A188
R⁴ = R^A4, R¹ = R^B2, L_A189
R⁴ = R^A5, R¹ = R^B2, L_A190

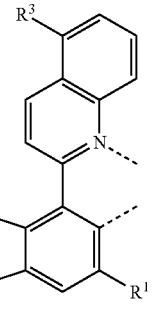

R⁵ = R^A1, R¹ = R^B1, L_A191
R⁵ = R^A2, R¹ = R^B1, L_A192
R⁵ = R^A3, R¹ = R^B1, L_A193
R⁵ = R^A4, R¹ = R^B1, L_A194
R⁵ = R^A5, R¹ = R^B1, L_A195
R⁵ = R^A1, R¹ = R^B2, L_A196
R⁵ = R^A2, R¹ = R^B2, L_A197
R⁵ = R^A3, R¹ = R^B2, L_A198
R⁵ = R^A4, R¹ = R^B2, L_A199
R⁵ = R^A5, R¹ = R^B2, L_A200

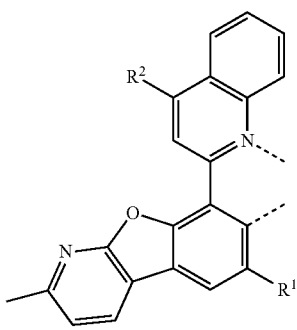

R² = R^A1, R¹ = R^B1, L_A201
R² = R^A2, R¹ = R^B1, L_A202
R² = R^A3, R¹ = R^B1, L_A203
R² = R^A4, R¹ = R^B1, L_A204
R² = R^A5, R¹ = R^B1, L_A205
R² = R^A1, R¹ = R^B2, L_A206
R² = R^A2, R¹ = R^B2, L_A207
R² = R^A3, R¹ = R^B2, L_A208
R² = R^A4, R¹ = R^B2, L_A209
R² = R^A5, R¹ = R^B2, L_A210

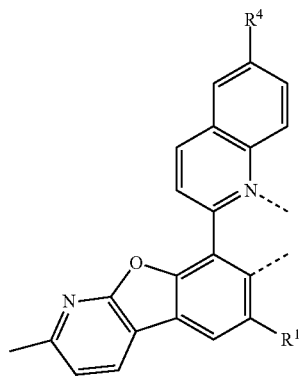

R³ = R^A1, R¹ = R^B1, L_A211
R³ = R^A2, R¹ = R^B1, L_A212
R³ = R^A3, R¹ = R^B1, L_A213
R³ = R^A4, R¹ = R^B1, L_A214
R³ = R^A5, R¹ = R^B1, L_A215
R³ = R^A1, R¹ = R^B2, L_A216
R³ = R^A2, R¹ = R^B2, L_A217
R³ = R^A3, R¹ = R^B2, L_A218
R³ = R^A4, R¹ = R^B2, L_A219
R³ = R^A5, R¹ = R^B2, L_A220

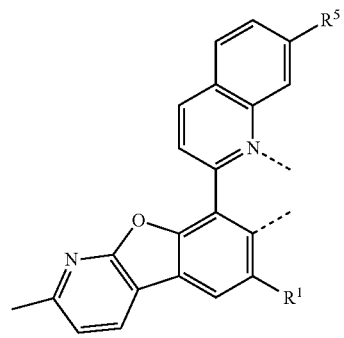

R⁴ = R^A1, R¹ = R^B1, L_A221
R⁴ = R^A2, R¹ = R^B1, L_A222
R⁴ = R^A3, R¹ = R^B1, L_A223
R⁴ = R^A4, R¹ = R^B1, L_A224
R⁴ = R^A5, R¹ = R^B1, L_A225
R⁴ = R^A1, R¹ = R^B2, L_A226
R⁴ = R^A2, R¹ = R^B2, L_A227
R⁴ = R^A3, R¹ = R^B2, L_A228
R⁴ = R^A4, R¹ = R^B2, L_A229
R⁴ = R^A5, R¹ = R^B2, L_A230

R⁵ = R^A1, R¹ = R^B1, L_A231
R⁵ = R^A2, R¹ = R^B1, L_A232
R⁵ = R^A3, R¹ = R^B1, L_A233

R⁵ = R⁴⁴, R¹ = R^B1, L_{A234}
R⁵ = R⁴⁵, R¹ = R^B1, L_{A235}
R⁵ = R⁴¹, R¹ = R^B2, L_{A236}
R⁵ = R⁴², R¹ = R^B2, L_{A237}
R⁵ = R⁴³, R¹ = R^B2, L_{A238}
R⁵ = R⁴⁴, R¹ = R^B2, L_{A239}
R² = R⁴⁵, R¹ = R^B2, L_{A240}

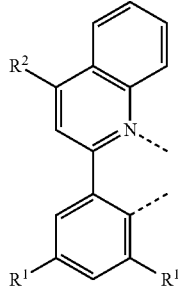

R² = R⁴¹, R¹ = R^B3, L_{A241}
R² = R⁴², R¹ = R^B3, L_{A242}
R² = R⁴³, R¹ = R^B3, L_{A243}
R² = R⁴⁴, R¹ = R^B3, L_{A244}
R² = R⁴⁵, R¹ = R^B3, L_{A245}
R² = R⁴¹, R¹ = R^B4, L_{A246}
R² = R⁴², R¹ = R^B4, L_{A247}
R² = R⁴³, R¹ = R^B4, L_{A248}
R² = R⁴⁴, R¹ = R^B4, L_{A249}
R² = R⁴⁵, R¹ = R^B4, L_{A250}

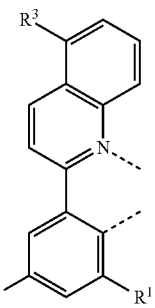

R³ = R⁴¹, R¹ = R^B3, L_{A251}
R³ = R⁴², R¹ = R^B3, L_{A252}
R³ = R⁴³, R¹ = R^B3, L_{A253}
R³ = R⁴⁴, R¹ = R^B3, L_{A254}
R³ = R⁴⁵, R¹ = R^B3, L_{A255}
R³ = R⁴¹, R¹ = R^B4, L_{A256}
R³ = R⁴², R¹ = R^B4, L_{A257}
R³ = R⁴³, R¹ = R^B4, L_{A258}
R³ = R⁴⁴, R¹ = R^B4, L_{A259}
R³ = R⁴⁵, R¹ = R^B4, L_{A260}

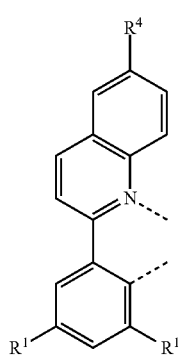

R⁴ = R⁴¹, R¹ = R^B3, L_{A261}
R⁴ = R⁴², R¹ = R^B3, L_{A262}
R⁴ = R⁴³, R¹ = R^B3, L_{A263}
R⁴ = R⁴⁴, R¹ = R^B3, L_{A264}
R⁴ = R⁴⁵, R¹ = R^B3, L_{A265}
R⁴ = R⁴¹, R¹ = R^B4, L_{A266}
R⁴ = R⁴², R¹ = R^B4, L_{A267}
R⁴ = R⁴³, R¹ = R^B4, L_{A268}
R⁴ = R⁴⁴, R¹ = R^B4, L_{A269}
R⁴ = R⁴⁵, R¹ = R^B4, L_{A270}

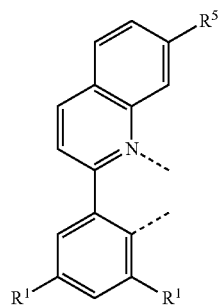

R⁵ = R⁴¹, R¹ = R^B3, L_{A271}
R⁵ = R⁴², R¹ = R^B3, L_{A272}
R⁵ = R⁴³, R¹ = R^B3, L_{A273}
R⁵ = R⁴⁴, R¹ = R^B3, L_{A274}
R⁵ = R⁴⁵, R¹ = R^B3, L_{A275}
R⁵ = R⁴¹, R¹ = R^B4, L_{A276}
R⁵ = R⁴², R¹ = R^B4, L_{A277}
R⁵ = R⁴³, R¹ = R^B4, L_{A278}
R⁵ = R⁴⁴, R¹ = R^B4, L_{A279}
R⁵ = R⁴⁵, R¹ = R^B4, L_{A280}

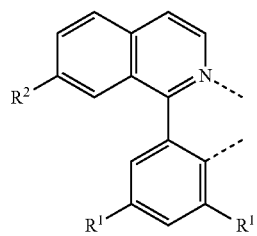

R² = R⁴¹, R¹ = R^B3, L_{A281}
R² = R⁴², R¹ = R^B3, L_{A282}
R² = R⁴³, R¹ = R^B3, L_{A283}
R² = R⁴⁴, R¹ = R^B3, L_{A284}
R² = R⁴⁵, R¹ = R^B3, L_{A285}
R² = R⁴¹, R¹ = R^B4, L_{A286}
R² = R⁴², R¹ = R^B4, L_{A287}
R² = R⁴³, R¹ = R^B4, L_{A288}
R² = R⁴⁴, R¹ = R^B4, L_{A289}
R² = R⁴⁵, R¹ = R^B4, L_{A290}

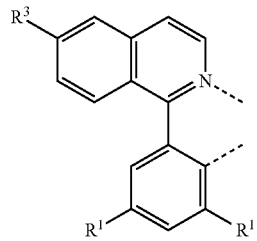

R³ = R⁴¹, R¹ = R^B3, L_{A291}
R³ = R⁴², R¹ = R^B3, L_{A292}
R³ = R⁴³, R¹ = R^B3, L_{A293}
R³ = R⁴⁴, R¹ = R^B3, L_{A294}
R³ = R⁴⁵, R¹ = R^B3, L_{A295}
R³ = R⁴¹, R¹ = R^B4, L_{A296}
R³ = R⁴², R¹ = R^B4, L_{A297}
R³ = R⁴³, R¹ = R^B4, L_{A298}
R³ = R⁴⁴, R¹ = R^B4, L_{A299}
R³ = R⁴⁵, R¹ = R^B4, L_{A300}

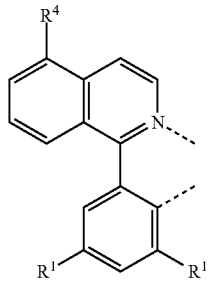

R⁴ = R^{A1}, R¹ = R^{B3}, L_{A301}
R⁴ = R^{A2}, R¹ = R^{B3}, L_{A302}
R⁴ = R^{A3}, R¹ = R^{B3}, L_{A303}
R⁴ = R^{A4}, R¹ = R^{B3}, L_{A304}
R⁴ = R^{A5}, R¹ = R^{B3}, L_{A305}
R⁴ = R^{A1}, R¹ = R^{B4}, L_{A306}
R⁴ = R^{A2}, R¹ = R^{B4}, L_{A307}
R⁴ = R^{A3}, R¹ = R^{B4}, L_{A308}
R⁴ = R^{A4}, R¹ = R^{B4}, L_{A309}
R⁴ = R^{A5}, R¹ = R^{B4}, L_{A310}

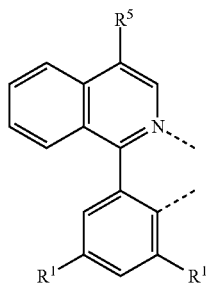

R⁵ = R^{A1}, R¹ = R^{B3}, L_{A311}
R⁵ = R^{A2}, R¹ = R^{B3}, L_{A312}
R⁵ = R^{A3}, R¹ = R^{B3}, L_{A313}
R⁵ = R^{A4}, R¹ = R^{B3}, L_{A314}
R⁵ = R^{A5}, R¹ = R^{B3}, L_{A315}
R⁵ = R^{A1}, R¹ = R^{B4}, L_{A316}
R⁵ = R^{A2}, R¹ = R^{B4}, L_{A317}
R⁵ = R^{A3}, R¹ = R^{B4}, L_{A318}
R⁵ = R^{A4}, R¹ = R^{B4}, L_{A319}
R⁵ = R^{A5}, R¹ = R^{B4}, L_{A320}

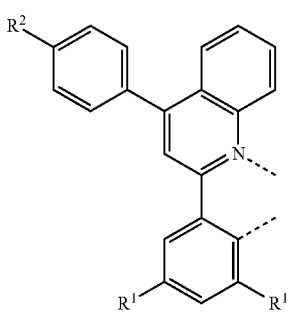

R² = R^{A1}, R¹ = R^{B3}, L_{A321}
R² = R^{A2}, R¹ = R^{B3}, L_{A322}
R² = R^{A3}, R¹ = R^{B3}, L_{A323}
R² = R^{A4}, R¹ = R^{B3}, L_{A324}
R² = R^{A5}, R¹ = R^{B3}, L_{A325}
R² = R^{A1}, R¹ = R^{B4}, L_{A326}
R² = R^{A2}, R¹ = R^{B4}, L_{A327}
R² = R^{A3}, R¹ = R^{B4}, L_{A328}
R² = R^{A4}, R¹ = R^{B4}, L_{A329}
R² = R^{A5}, R¹ = R^{B4}, L_{A330}

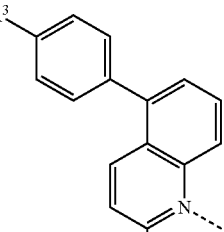

R³ = R^{A1}, R¹ = R^{B3}, L_{A331}
R³ = R^{A2}, R¹ = R^{B3}, L_{A332}
R³ = R^{A3}, R¹ = R^{B3}, L_{A333}
R³ = R^{A4}, R¹ = R^{B3}, L_{A334}
R³ = R^{A5}, R¹ = R^{B3}, L_{A335}
R³ = R^{A1}, R¹ = R^{B4}, L_{A336}
R³ = R^{A2}, R¹ = R^{B4}, L_{A337}
R³ = R^{A3}, R¹ = R^{B4}, L_{A338}
R³ = R^{A4}, R¹ = R^{B4}, L_{A339}
R³ = R^{A5}, R¹ = R^{B4}, L_{A340}

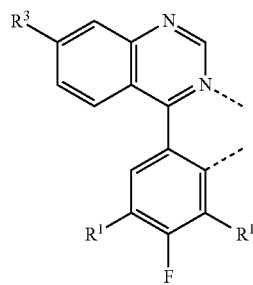

R⁴ = R^{A1}, R¹ = R^{B3}, L_{A341}
R⁴ = R^{A2}, R¹ = R^{B3}, L_{A342}
R⁴ = R^{A3}, R¹ = R^{B3}, L_{A343}
R⁴ = R^{A4}, R¹ = R^{B3}, L_{A344}
R⁴ = R^{A5}, R¹ = R^{B3}, L_{A345}
R⁴ = R^{A1}, R¹ = R^{B4}, L_{A346}
R⁴ = R^{A2}, R¹ = R^{B4}, L_{A347}
R⁴ = R^{A3}, R¹ = R^{B4}, L_{A348}
R⁴ = R^{A4}, R¹ = R^{B4}, L_{A349}
R⁴ = R^{A5}, R¹ = R^{B4}, L_{A350}

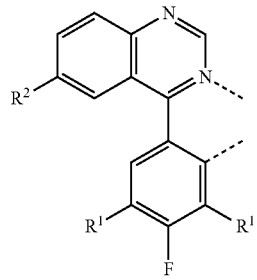

R⁵ = R^{A1}, R¹ = R^{B3}, L_{A351}
R⁵ = R^{A2}, R¹ = R^{B3}, L_{A352}
R⁵ = R^{A3}, R¹ = R^{B3}, L_{A353}
R⁵ = R^{A4}, R¹ = R^{B3}, L_{A354}
R⁵ = R^{A5}, R¹ = R^{B3}, L_{A355}
R⁵ = R^{A1}, R¹ = R^{B4}, L_{A356}
R⁵ = R^{A2}, R¹ = R^{B4}, L_{A357}
R⁵ = R^{A3}, R¹ = R^{B4}, L_{A358}
R⁵ = R^{A4}, R¹ = R^{B4}, L_{A359}
R⁵ = R^{A5}, R¹ = R^{B4}, L_{A360}

-continued

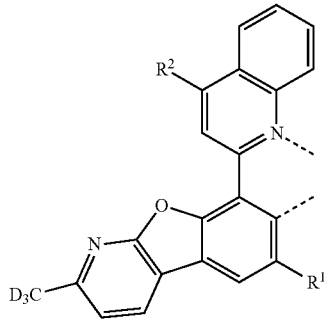

R² = R⁴¹, R¹ = R^B³, L_{A361}
R² = R⁴², R¹ = R^B³, L_{A362}
R² = R⁴³, R¹ = R^B³, L_{A363}
R² = R⁴⁴, R¹ = R^B³, L_{A364}
R² = R⁴⁵, R¹ = R^B³, L_{A365}
R² = R⁴¹, R¹ = R^B⁴, L_{A366}
R² = R⁴², R¹ = R^B⁴, L_{A367}
R² = R⁴³, R¹ = R^B⁴, L_{A368}
R² = R⁴⁴, R¹ = R^B⁴, L_{A369}
R² = R⁴⁵, R¹ = R^B⁴, L_{A370}

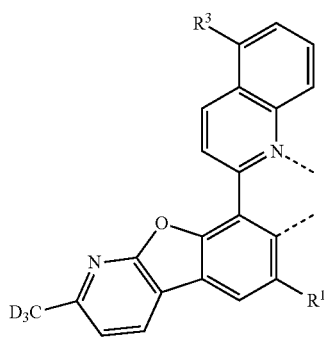

R³ = R⁴¹, R¹ = R^B³, L_{A371}
R³ = R⁴², R¹ = R^B³, L_{A372}
R³ = R⁴³, R¹ = R^B³, L_{A373}
R³ = R⁴⁴, R¹ = R^B³, L_{A374}
R³ = R⁴⁵, R¹ = R^B³, L_{A375}
R³ = R⁴¹, R¹ = R^B⁴, L_{A376}
R³ = R⁴², R¹ = R^B⁴, L_{A377}
R³ = R⁴³, R¹ = R^B⁴, L_{A378}
R³ = R⁴⁴, R¹ = R^B⁴, L_{A379}
R³ = R⁴⁵, R¹ = R^B⁴, L_{A380};

wherein $R^{A1}$ to $R^{A5}$, and $R^{B1}$ to $R^{B4}$ have the following structures:

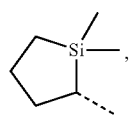 $R^{A1}$

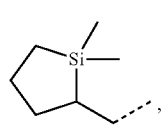 $R^{A2}$

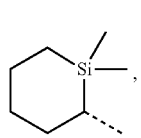 $R^{A3}$

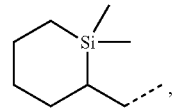 $R^{A4}$

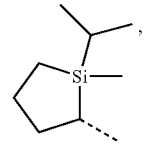 $R^{A5}$

--- H, $R^{B1}$

--- CH₃, $R^{B2}$

--- CD₃, $R^{B3}$

 $R^{B4}$

15. The composition of claim 14, wherein the compound is selected from the group consisting of Compound 1 through Compound 4940; wherein Compound x has the formula $M(L_{Ai})_2(L_{Cj})$;

wherein x=380j+i−380, i is an integer from 1 to 380, and j is an integer from 1 to 13; and wherein $L_{Cj}$ has the following formula:

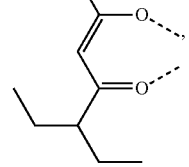 $L_{C1}$

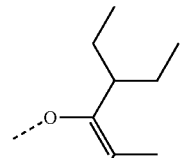 $L_{C2}$

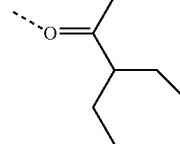 $L_{C3}$

-continued

L_C4 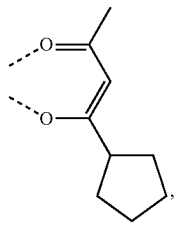

L_C5 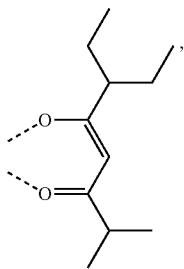

L_C6 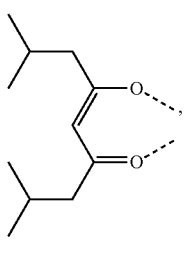

L_C7 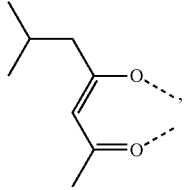

L_C8 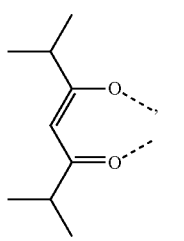

L_C9 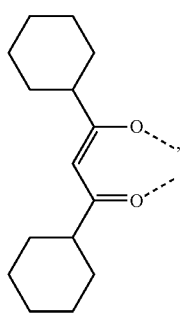

L_C10 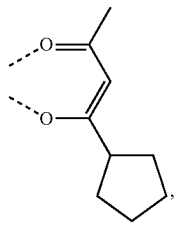

L_C11 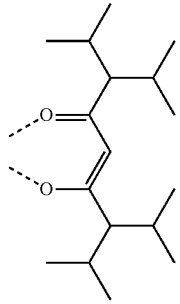

L_C12 or 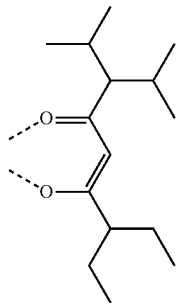

L_C13 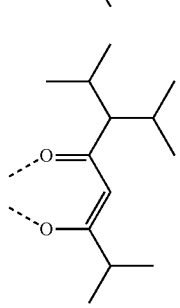

16. An organic light-emitting device (OLED) comprising:
an anode;
a cathode; and
an organic layer, disposed between the anode and the cathode, comprising a first compound;
wherein the first compound is capable of functioning as an emitter in an organic light emitting device at room temperature;
wherein the first compound has at least one aromatic ring and at least one substituent R;
wherein each of the at least one substituent R is directly bonded to one of the aromatic rings;
wherein each of the at least one substituent R has the formula

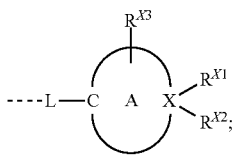

wherein L is a direct bond or an organic linker;
wherein ring A is a non-aromatic cyclic group containing X;
wherein L bonds to ring A at a carbon atom C;
wherein X is Si or Ge;
wherein $R^{X3}$ represents mono to the possible maximum number of substitution, or no substitution;
wherein $R^{X1}$, $R^{X2}$ and $R^{X3}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substituents $R^{X1}$, $R^{X2}$ and $R^{X3}$ are optionally joined or fused into a ring.

17. The OLED of claim 16, wherein the organic layer is an emissive layer and the compound is an emissive dopant or a non-emissive dopant.

18. The OLED of claim 16, wherein the organic layer further comprises a host, wherein said host comprises at least one chemical group selected from the group consisting of triphenylene, carbazole, dibenzothiphene, dibenzofuran, dibenzoselenophene, aza-triphenylene, azacarbazole, aza-dibenzothiophene, aza-dibenzofuran, and aza-dibenzoselenophene.

19. A consumer product comprising an organic light-emitting device (OLED) comprising:
an anode;
a cathode; and
an organic layer, disposed between the anode and the cathode, comprising a first compound;
wherein the first compound is capable of functioning as an emitter in an organic light emitting device at room temperature;
wherein the first compound has at least one aromatic ring and at least one substituent R;
wherein each of the at least one substituent R is directly bonded to one of the aromatic rings;
wherein each of the at least one substituent R has the formula

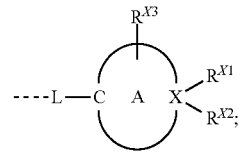

wherein L is a direct bond or an organic linker;
wherein ring A is a non-aromatic cyclic group containing X;
wherein L bonds to ring A at a carbon atom C;
wherein X is Si or Ge;
wherein $R^{X3}$ represents mono to the possible maximum number of substitution, or no substitution;
wherein $R^{X1}$, $R^{X2}$ and $R^{X3}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any adjacent substituents $R^{X1}$, $R^{X2}$ and $R^{X3}$ are optionally joined or fused into a ring.

20. The consumer product of claim 19, wherein the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and a sign.

* * * * *